(12) United States Patent
Wenchell, Jr. et al.

(10) Patent No.: US 11,617,580 B2
(45) Date of Patent: Apr. 4, 2023

(54) SURGICAL STAPLER WITH REMOVABLE POWER PACK AND INTERCHANGEABLE BATTERY PACK

(71) Applicant: RevMedica, Inc., Durham, CT (US)

(72) Inventors: Thomas G. Wenchell, Jr., Durham, CT (US); C. Robert Satti, III, Westbrook, CT (US); Peter Nielsen, Ridgefield, CT (US); Jeffrey M. Ott, New Haven, CT (US)

(73) Assignee: RevMedica, Inc., Durham, CT (US)

( * ) Notice: Subject to any disclaimer, the term of this patent is extended or adjusted under 35 U.S.C. 154(b) by 0 days.

(21) Appl. No.: 17/738,129

(22) Filed: May 6, 2022

(65) Prior Publication Data
US 2022/0257245 A1    Aug. 18, 2022

Related U.S. Application Data

(63) Continuation of application No. 16/792,110, filed on Feb. 14, 2020, now Pat. No. 11,331,099, which is a
(Continued)

(51) Int. Cl.
*A61B 17/072*    (2006.01)
*A61B 17/00*    (2006.01)
*A61B 17/29*    (2006.01)

(52) U.S. Cl.
CPC ........ *A61B 17/072* (2013.01); *A61B 17/2909* (2013.01); *A61B 2017/00398* (2013.01);
(Continued)

(58) Field of Classification Search
CPC .............. A61B 17/072; A61B 17/2909; A61B 2017/0046; A61B 2017/00734;
(Continued)

(56) References Cited

U.S. PATENT DOCUMENTS 2,636,136 A    4/1953    Henry
2,942,603 A    6/1960    Geyer
(Continued)

FOREIGN PATENT DOCUMENTS

CN    106456172    9/2019
EP    0685203    12/1995
(Continued)

OTHER PUBLICATIONS

European Search Report (dated Mar. 3, 2022) from European Application No. EP 20766786.
(Continued)

*Primary Examiner* — Anna K Kinsaul
*Assistant Examiner* — Veronica Martin
(74) *Attorney, Agent, or Firm* — Neil D. Gershon

(57) ABSTRACT

A surgical fastener applier including a housing containing a compartment, an elongated member extending distally from the housing, first and second jaws and a firing mechanism. The firing mechanism is movable between a first position and a second position to effect firing of fasteners into the tissue clamped between the first and second jaws. A power pack is removably loadable into the compartment, the power pack having a motor and an engagement member removably engageable with the firing mechanism within the compartment when the power pack is loaded into the compartment to effect movement of the firing mechanism. An interchangeable battery pack is removably loadable into the power pack for powering the motor. Bearings restrict axial and radial movement of the firing and articulation assembly in the power pack.

18 Claims, 56 Drawing Sheets

Related U.S. Application Data continuation-in-part of application No. 15/965,737, filed on Apr. 27, 2018, now Pat. No. 10,966,720.

(60) Provisional application No. 62/900,146, filed on Sep. 13, 2019, provisional application No. 62/812,934, filed on Mar. 1, 2019, provisional application No. 62/616,045, filed on Jan. 11, 2018, provisional application No. 62/553,297, filed on Sep. 1, 2017.

(52) U.S. Cl.
CPC ......... *A61B 2017/00424* (2013.01); *A61B 2017/00477* (2013.01); *A61B 2017/00734* (2013.01); *A61B 2017/2948* (2013.01)

(58) Field of Classification Search
CPC ........... A61B 2017/00743; A61B 2017/00464; A61B 2017/00017; A61B 2017/00115; A61B 2017/00398; A61B 2017/00477; A61B 2017/07257; A61B 2017/07271; A61B 2017/2905; A61B 2017/2927; A61B 2017/2929; A61B 2017/2948
See application file for complete search history.

(56) References Cited

U.S. PATENT DOCUMENTS

| | | | |
|---|---|---|---|
| 3,442,240 | A | 5/1969 | Loughman et al. |
| 3,494,799 | A | 2/1970 | Pedone, Jr. |
| 3,734,207 | A | 5/1973 | Fishbein |
| 4,250,613 | A | 2/1981 | Sauerwein |
| 4,705,038 | A | 11/1987 | Sjostrom et al. |
| 4,867,158 | A | 9/1989 | Sugg |
| 4,962,681 | A | 10/1990 | Yang |
| 5,207,697 | A | 5/1993 | Carusillo et al. |
| 5,261,877 | A | 11/1993 | Fine |
| 5,387,217 | A | 2/1995 | Sefcik |
| 5,467,911 | A | 11/1995 | Tsuruta et al. |
| 5,478,351 | A | 12/1995 | Meade |
| 5,518,163 | A | 5/1996 | Hooven |
| 5,551,622 | A | 9/1996 | Yoon |
| 5,553,675 | A | 9/1996 | Pitzen et al. |
| 5,651,491 | A | 7/1997 | Heaton et al. |
| 5,680,981 | A | 10/1997 | Milii et al. |
| 5,814,058 | A | 9/1998 | Carlson et al. |
| 5,954,259 | A | 9/1999 | Viola et al. |
| 6,054,777 | A | 4/2000 | Soh |
| 6,331,181 | B1 | 12/2001 | Tierney |
| 6,331,761 | B1 | 12/2001 | Kumar et al. |
| 6,512,348 | B1 | 1/2003 | Wellisz et al. |
| 6,530,931 | B1 | 3/2003 | Rosenberg |
| 6,533,157 | B1 | 3/2003 | Whitman |
| 6,716,233 | B1 | 4/2004 | Whitman |
| 6,843,303 | B2 | 1/2005 | Siak et al. |
| 6,846,307 | B2 | 1/2005 | Whitman et al. |
| 6,981,141 | B1 | 12/2005 | Mahne et al. |
| 7,160,311 | B2 | 1/2007 | Blatter |
| 7,416,101 | B2 | 8/2008 | Shelton, IV et al. |
| 7,422,136 | B1 | 9/2008 | Marczyk |
| 7,422,139 | B2 | 9/2008 | Shelton, IV et al. |
| 7,461,767 | B2 | 12/2008 | Viola et al. |
| 7,464,847 | B2 | 12/2008 | Viola et al. |
| 7,537,602 | B2 | 5/2009 | Whitman |
| 7,568,603 | B2 | 8/2009 | Shelton, IV et al. |
| 7,699,855 | B2 | 4/2010 | Anderson |
| 7,717,312 | B2 | 5/2010 | Beetel |
| 7,766,210 | B2 | 8/2010 | Shelton, IV et al. |
| 7,793,812 | B2 | 9/2010 | Moore et al. |
| 7,815,092 | B2 | 10/2010 | Whitman et al. |
| 7,845,538 | B2 | 12/2010 | Whitman |
| 7,922,063 | B2 | 4/2011 | Zemlok et al. |
| 7,947,034 | B2 | 5/2011 | Whitman |
| 7,950,560 | B2 | 5/2011 | Zemlok et al. |
| 7,959,050 | B2 | 6/2011 | Smith et al. |
| 7,963,433 | B2 | 6/2011 | Whitman et al. |
| 8,006,885 | B2 | 8/2011 | Marczyk |
| 8,011,551 | B2 | 9/2011 | Marczyk et al. |
| 8,012,170 | B2 | 9/2011 | Whitman et al. |
| 8,016,855 | B2 | 9/2011 | Whitman et al. |
| 8,016,858 | B2 | 9/2011 | Whitman |
| 8,021,373 | B2 | 9/2011 | Whitman et al. |
| 8,056,786 | B2 | 11/2011 | Whitman et al. |
| 8,056,791 | B2 | 11/2011 | Whitman |
| 8,062,311 | B2 | 11/2011 | Litscher et al. |
| 8,074,858 | B2 | 12/2011 | Marczyk |
| 8,142,447 | B2 | 3/2012 | Cooper |
| 8,142,473 | B2 | 3/2012 | Cunningham |
| 8,157,150 | B2 | 4/2012 | Viola et al. |
| 8,181,839 | B2 | 5/2012 | Beetel |
| 8,186,555 | B2 | 5/2012 | Shelton, IV et al. |
| 8,205,779 | B2 | 6/2012 | Ma et al. |
| 8,240,536 | B2 | 8/2012 | Marczyk |
| 8,240,537 | B2 | 8/2012 | Marczyk |
| 8,241,322 | B2 | 8/2012 | Whitman et al. |
| 8,245,899 | B2 | 8/2012 | Swensgard et al. |
| 8,251,994 | B2 | 8/2012 | McKenna et al. |
| 8,257,387 | B2 | 9/2012 | Cunningham |
| 8,276,801 | B2 | 10/2012 | Zemlok et al. |
| 8,342,377 | B2 | 1/2013 | Milliman et al. |
| 8,342,378 | B2 | 1/2013 | Marczyk et al. |
| 8,353,440 | B2 | 1/2013 | Whitman et al. |
| 8,409,175 | B2 | 4/2013 | Lee et al. |
| 8,409,222 | B2 | 4/2013 | Whitfield et al. |
| 8,444,036 | B2 | 5/2013 | Shelton, IV |
| 8,453,907 | B2 | 6/2013 | Laurent et al. |
| 8,453,914 | B2 | 6/2013 | Laurent et al. |
| 8,459,521 | B2 | 6/2013 | Zemlok et al. |
| 8,459,525 | B2 | 6/2013 | Yates et al. |
| 8,479,969 | B2 | 7/2013 | Shelton, IV |
| 8,499,992 | B2 | 8/2013 | Whitman et al. |
| 8,517,241 | B2 | 8/2013 | Nicholas et al. |
| 8,551,025 | B2 | 10/2013 | Soltz |
| 8,556,151 | B2 | 10/2013 | Viola |
| 8,573,462 | B2 | 11/2013 | Smith et al. |
| 8,573,463 | B2 | 11/2013 | Scirica et al. |
| 8,602,287 | B2 | 12/2013 | Yates et al. |
| 8,602,288 | B2 | 12/2013 | Shelton, IV et al. |
| 8,608,045 | B2 | 12/2013 | Smith et al. |
| 8,622,274 | B2 | 1/2014 | Yates et al. |
| 8,631,998 | B1 | 1/2014 | Viola |
| 8,636,736 | B2 | 1/2014 | Yates et al. |
| 8,636,766 | B2 | 1/2014 | Milliman et al. |
| 8,657,174 | B2 | 2/2014 | Yates et al. |
| 8,657,177 | B2 | 2/2014 | Scirica et al. |
| 8,662,371 | B2 | 3/2014 | Viola |
| 8,672,206 | B2 | 3/2014 | Aranyi et al. |
| 8,690,913 | B2 | 4/2014 | Whitman |
| 8,708,213 | B2 | 4/2014 | Shelton, IV et al. |
| 8,733,614 | B2 | 5/2014 | Ross et al. |
| 8,752,748 | B2 | 6/2014 | Whitman et al. |
| 8,764,749 | B2 | 7/2014 | Mckenna et al. |
| 8,777,945 | B2 | 7/2014 | Floume et al. |
| 8,795,313 | B2 | 8/2014 | Liang et al. |
| 8,800,837 | B2 | 8/2014 | Zemlok |
| 8,820,603 | B2 | 9/2014 | Shelton, IV et al. |
| 8,821,514 | B2 | 9/2014 | Aranyi |
| 8,827,134 | B2 | 9/2014 | Viola et al. |
| 8,834,466 | B2 | 9/2014 | Cummings et al. |
| 8,851,355 | B2 | 10/2014 | Aranyi et al. |
| 8,864,753 | B2 | 10/2014 | Nau, Jr. et al. |
| 8,875,973 | B2 | 11/2014 | Whitman |
| 8,899,462 | B2 | 12/2014 | Kostrzewski et al. |
| 8,911,471 | B2 | 12/2014 | Spivey et al. |
| 8,955,732 | B2 | 2/2015 | Zemlok et al. |
| 8,960,520 | B2 | 2/2015 | McCuen |
| 8,967,443 | B2 | 3/2015 | McCuen |
| 8,968,276 | B2 | 3/2015 | Zemlok et al. |
| 8,968,285 | B2 | 3/2015 | Twomey et al. |
| 8,991,677 | B2 | 3/2015 | Moore et al. |
| 8,998,058 | B2 | 4/2015 | Moore et al. |
| 9,017,355 | B2 | 4/2015 | Smith et al. |
| 9,028,478 | B2 | 5/2015 | Mueller |
| 9,072,523 | B2 | 7/2015 | Houser et al. |

(56) References Cited

U.S. PATENT DOCUMENTS

| | | | |
|---|---|---|---|
| 9,084,601 | B2 | 7/2015 | Moore et al. |
| 9,095,339 | B2 | 8/2015 | Moore et al. |
| 9,101,358 | B2 | 8/2015 | Kerr et al. |
| 9,113,874 | B2 | 8/2015 | Shelton, IV et al. |
| 9,113,880 | B2 | 8/2015 | Zemlok et al. |
| 9,113,901 | B2 | 8/2015 | Allen, IV et al. |
| 9,186,143 | B2 | 11/2015 | Timm et al. |
| 9,192,381 | B2 | 11/2015 | Marczyk |
| 9,241,716 | B2 | 1/2016 | Whitman |
| 9,265,585 | B2 | 2/2016 | Wingardner et al. |
| 9,301,772 | B2 | 4/2016 | Kimball et al. |
| 9,320,520 | B2 | 4/2016 | Shelton, IV et al. |
| 9,326,770 | B2 | 5/2016 | Shelton, IV et al. |
| 9,326,812 | B2 | 5/2016 | Waaler et al. |
| 9,351,727 | B2 | 5/2016 | Leimbach et al. |
| 9,364,220 | B2 | 6/2016 | Williams |
| 9,364,224 | B2 | 6/2016 | Nicholas et al. |
| 9,370,360 | B2 | 6/2016 | Marczyk |
| 9,370,364 | B2 | 6/2016 | Smith et al. |
| 9,393,015 | B2 | 7/2016 | Laurent et al. |
| 9,398,911 | B2 | 7/2016 | Auld |
| 9,402,604 | B2 | 8/2016 | Williams et al. |
| 9,414,818 | B2 | 8/2016 | Azarbarzin et al. |
| 9,421,003 | B2 | 8/2016 | Williams et al. |
| 9,421,014 | B2 | 8/2016 | Ingmanson et al. |
| 9,433,415 | B2 | 9/2016 | Marczyk et al. |
| 9,451,958 | B2 | 9/2016 | Shelton, IV et al. |
| 9,468,454 | B2 | 10/2016 | Johnson et al. |
| 9,474,513 | B2 | 10/2016 | Ishida |
| 9,474,528 | B2 | 10/2016 | Marczyk |
| 9,484,657 | B2 | 11/2016 | Martin et al. |
| 9,486,214 | B2 | 11/2016 | Shelton, IV |
| 9,492,167 | B2 | 11/2016 | Shelton, IV et al. |
| 9,504,520 | B2 | 11/2016 | Worell et al. |
| 9,517,068 | B2 | 12/2016 | Shelton, IV et al. |
| 9,539,006 | B2 | 1/2017 | Collings et al. |
| 9,549,750 | B2 | 1/2017 | Shelton, IV et al. |
| 9,554,803 | B2 | 1/2017 | Smith et al. |
| 9,561,031 | B2 | 2/2017 | Heinrich et al. |
| 9,585,672 | B2 | 3/2017 | Bastia |
| 9,592,056 | B2 | 3/2017 | Mozdzierz et al. |
| 9,597,081 | B2 | 3/2017 | Swayze et al. |
| 9,615,828 | B2 | 4/2017 | Scirica |
| 9,622,744 | B2 | 4/2017 | Smith et al. |
| 9,636,091 | B2 | 5/2017 | Beardsley et al. |
| 9,649,110 | B2 | 5/2017 | Parilhar et al. |
| 9,655,614 | B2 | 5/2017 | Swensgard et al. |
| 9,662,110 | B2 | 5/2017 | Huang et al. |
| 9,675,348 | B2 | 6/2017 | Smith et al. |
| 9,685,281 | B2 | 6/2017 | Wang et al. |
| 9,687,230 | B2 | 6/2017 | Leimbach et al. |
| 9,687,234 | B2 | 6/2017 | Smith et al. |
| 9,687,236 | B2 | 6/2017 | Leimbach et al. |
| 9,687,253 | B2 | 6/2017 | Detry et al. |
| 9,700,310 | B2 | 7/2017 | Moragan et al. |
| 9,700,318 | B2 | 7/2017 | Scirica et al. |
| 9,743,928 | B2 | 8/2017 | Shelton, IV et al. |
| 9,750,499 | B2 | 9/2017 | Leimbach et al. |
| 9,775,610 | B2 | 10/2017 | Nicholas et al. |
| 9,782,172 | B2 | 10/2017 | Whitman |
| 9,782,187 | B2 | 10/2017 | Zergiebal et al. |
| 9,788,836 | B2 | 10/2017 | Overmyer et al. |
| 9,797,486 | B2 | 10/2017 | Zergiebal et al. |
| 9,801,626 | B2 | 10/2017 | Parilhar et al. |
| 9,826,976 | B2 | 11/2017 | Parihar et al. |
| 9,833,235 | B2 | 12/2017 | Penna et al. |
| 9,844,368 | B2 | 12/2017 | Boudreanx et al. |
| 9,844,375 | B2 | 12/2017 | Overmyer et al. |
| 9,867,612 | B2 | 1/2018 | Parilhar et al. |
| 9,877,720 | B2 | 1/2018 | Worrell et al. |
| 9,901,344 | B2 | 2/2018 | Moore et al. |
| 9,901,346 | B2 | 2/2018 | Moore et al. |
| 9,907,552 | B2 | 3/2018 | Measamer et al. |
| 9,924,942 | B2 | 3/2018 | Swayze et al. |
| 9,936,949 | B2 | 4/2018 | Measamer et al. |
| 9,936,951 | B2 | 4/2018 | Hufhagel et al. |
| 9,937,626 | B2 | 4/2018 | Rockrohr |
| 9,949,737 | B2 | 4/2018 | Zergiebel et al. |
| 9,955,965 | B2 | 5/2018 | Chen et al. |
| 9,955,966 | B2 | 5/2018 | Zergiebel |
| 9,962,157 | B2 | 5/2018 | Sapre |
| 9,962,159 | B2 | 5/2018 | Heunrich et al. |
| 9,974,539 | B2 | 5/2018 | Yates et al. |
| 9,980,729 | B2 | 5/2018 | Moore et al. |
| 9,991,069 | B2 | 6/2018 | Nicholas et al. |
| 10,004,498 | B2 | 6/2018 | Morgan et al. |
| 10,041,822 | B2 | 8/2018 | Zemlok |
| 10,045,778 | B2 | 8/2018 | Yates |
| 10,052,100 | B2 | 8/2018 | Morgan et al. |
| 10,064,621 | B2 | 9/2018 | Kerr et al. |
| 10,070,861 | B2 | 9/2018 | Spivey et al. |
| 10,076,379 | B2 | 9/2018 | Boudreaux |
| 10,085,752 | B2 | 10/2018 | Williams et al. |
| 10,111,662 | B2 | 10/2018 | Zemlok et al. |
| 10,111,665 | B2 | 10/2018 | Aranyi et al. |
| 10,117,654 | B2 | 11/2018 | Ingmanson et al. |
| 10,136,887 | B2 | 11/2018 | Shelton, IV et al. |
| 10,143,472 | B2 | 12/2018 | Williams |
| 10,149,683 | B2 | 12/2018 | Smith et al. |
| 10,172,612 | B2 | 1/2019 | Frushour |
| 10,178,992 | B2 | 1/2019 | Wise et al. |
| 10,180,463 | B2 | 1/2019 | Beckman et al. |
| 10,182,816 | B2 | 1/2019 | Shelton, IV |
| 10,190,888 | B2 | 1/2019 | Hryb et al. |
| 10,194,907 | B2 | 2/2019 | Marczyk et al. |
| 10,220,522 | B2 | 3/2019 | Rockrohr |
| 10,226,249 | B2 | 3/2019 | Jaworek et al. |
| 10,226,250 | B2 | 3/2019 | Beckman et al. |
| 10,245,033 | B2 | 4/2019 | Overmyer et al. |
| 10,426,468 | B2 | 10/2019 | Contini |
| 10,507,034 | B2 | 12/2019 | Timm |
| 10,568,651 | B2 | 2/2020 | Kostrzewski |
| 10,617,415 | B2 | 4/2020 | Wenchell et al. |
| 10,625,384 | B2 | 4/2020 | Park |
| 10,695,060 | B2 | 6/2020 | Satti, III |
| 10,709,512 | B2 | 7/2020 | Bajo et al. |
| 10,722,312 | B2 | 7/2020 | Marshall et al. |
| 10,736,706 | B2 | 8/2020 | Scheib |
| 10,765,486 | B2 | 9/2020 | Bajo et al. |
| 10,779,822 | B2 | 9/2020 | Yates |
| 10,779,901 | B2 | 9/2020 | Zietlow et al. |
| 10,780,539 | B2 | 9/2020 | Shelton, IV |
| 10,821,046 | B2 | 11/2020 | Hares et al. |
| 10,874,391 | B2 | 12/2020 | Shelton, IV |
| 10,905,422 | B2 | 2/2021 | Bakos et al. |
| 10,959,806 | B2 | 3/2021 | Hibner |
| 11,197,672 | B2 | 12/2021 | Dunki-Jacobs |
| 2002/0021018 | A1 | 2/2002 | Royer |
| 2002/0096341 | A1 | 7/2002 | Hagan |
| 2002/0143346 | A1 | 10/2002 | McGuckin, Jr. et al. |
| 2003/0105475 | A1 | 6/2003 | Sancoff |
| 2003/0105488 | A1 | 6/2003 | Chu |
| 2003/0149424 | A1 | 8/2003 | Barlev |
| 2005/0021018 | A1 | 1/2005 | Anderson et al. |
| 2005/0033352 | A1 | 2/2005 | Zepf |
| 2005/0107809 | A1 | 5/2005 | Litscher et al. |
| 2005/0187576 | A1 | 8/2005 | Whitman |
| 2006/0017210 | A1 | 1/2006 | Sato |
| 2006/0037766 | A1 | 2/2006 | Gass |
| 2007/0023477 | A1 | 2/2007 | Whitman |
| 2007/0112364 | A1 | 5/2007 | Gerbi |
| 2007/0118163 | A1 | 5/2007 | Boudreaux et al. |
| 2007/0139915 | A1 | 6/2007 | Walters |
| 2008/0039884 | A1 | 2/2008 | Nohilly |
| 2008/0077149 | A1 | 3/2008 | Hoegerle |
| 2008/0203135 | A1 | 8/2008 | Viola et al. |
| 2008/0255597 | A1 | 10/2008 | Pravong et al. |
| 2008/0281353 | A1 | 11/2008 | Aranyi et al. |
| 2008/0296346 | A1 | 12/2008 | Shelton, IV |
| 2009/0012520 | A1 | 1/2009 | Hixson |
| 2009/0095790 | A1 | 4/2009 | Whitman |
| 2009/0108048 | A1 | 4/2009 | Zemlok |
| 2009/0110533 | A1 | 4/2009 | Jinno |
| 2009/0171243 | A1 | 7/2009 | Hibner |

(56) References Cited

U.S. PATENT DOCUMENTS

| | | |
|---|---|---|
| 2009/0182193 A1 | 7/2009 | Whitman |
| 2009/0209979 A1 | 8/2009 | Yates et al. |
| 2009/0250501 A1 | 10/2009 | Sonnenschein |
| 2009/0312603 A1 | 12/2009 | Lam et al. |
| 2010/0170931 A1 | 7/2010 | Viola |
| 2010/0213240 A1 | 8/2010 | Kostrzewski |
| 2010/0258327 A1 | 10/2010 | Esenwein |
| 2010/0320252 A1 | 12/2010 | Viola |
| 2011/0011915 A1 | 1/2011 | Shelton, IV |
| 2011/0012446 A1 | 1/2011 | Maute |
| 2011/0017801 A1 | 1/2011 | Zemlok |
| 2011/0022032 A1 | 1/2011 | Zemlok et al. |
| 2011/0082471 A1 | 4/2011 | Holcomb et al. |
| 2011/0125138 A1 | 5/2011 | Malinouskas |
| 2011/0125176 A1 | 5/2011 | Yates et al. |
| 2011/0155785 A1 | 6/2011 | Laurent |
| 2011/0166585 A1 | 7/2011 | Roth |
| 2011/0220381 A1 | 9/2011 | Friese |
| 2011/0264129 A1 | 10/2011 | Holdgate |
| 2011/0282381 A1 | 11/2011 | Cronin et al. |
| 2011/0295242 A1 | 12/2011 | Spivey et al. |
| 2012/0061446 A1 | 3/2012 | Knodel |
| 2012/0110810 A1 | 5/2012 | Houser et al. |
| 2012/0116263 A1 | 5/2012 | Houser |
| 2012/0172924 A1 | 7/2012 | Allen, IV |
| 2012/0199632 A1 | 8/2012 | Spivey |
| 2012/0223121 A1 | 9/2012 | Viola |
| 2012/0286021 A1 | 11/2012 | Kostrzewski |
| 2012/0292367 A1* | 11/2012 | Morgan .............. A61B 34/20 227/175.1 |
| 2012/0298719 A1 | 11/2012 | Shelton, IV |
| 2013/0098968 A1 | 4/2013 | Aranyi |
| 2013/0181033 A1 | 7/2013 | Shelton, IV et al. |
| 2013/0184704 A1 | 7/2013 | Beardsley |
| 2013/0193189 A1 | 8/2013 | Swensgard |
| 2013/0296886 A1 | 11/2013 | Green |
| 2013/0331847 A1 | 12/2013 | Smith |
| 2014/0001235 A1 | 1/2014 | Shelton, IV |
| 2014/0005718 A1 | 1/2014 | Shelton, IV et al. |
| 2014/0012289 A1 | 1/2014 | Snow et al. |
| 2014/0058363 A1 | 2/2014 | Berkelaar |
| 2014/0114334 A1 | 4/2014 | Olson |
| 2014/0166023 A1 | 6/2014 | Kishi |
| 2014/0175150 A1 | 6/2014 | Shelton, IV |
| 2014/0207125 A1 | 7/2014 | Applegate et al. |
| 2014/0213848 A1 | 7/2014 | Moskowitz et al. |
| 2014/0246471 A1 | 9/2014 | Jaworek |
| 2014/0246474 A1 | 9/2014 | Hall |
| 2014/0257252 A1 | 9/2014 | Ishida |
| 2014/0276471 A1 | 9/2014 | Emery |
| 2014/0277334 A1 | 9/2014 | Yu |
| 2014/0291383 A1 | 10/2014 | Spivey |
| 2014/0305987 A1 | 10/2014 | Parihar |
| 2014/0305992 A1 | 10/2014 | Kimsey |
| 2014/0305995 A1 | 10/2014 | Shelton, IV et al. |
| 2014/0309665 A1 | 10/2014 | Parihar |
| 2014/0309666 A1 | 10/2014 | Shelton, IV |
| 2014/0364890 A1 | 12/2014 | Moody |
| 2015/0053737 A1 | 2/2015 | Leimbach |
| 2015/0053749 A1 | 2/2015 | Shelton, IV |
| 2015/0090760 A1 | 4/2015 | Giordano et al. |
| 2015/0126977 A1 | 5/2015 | Azarbarzin et al. |
| 2015/0133979 A1 | 5/2015 | Johnson |
| 2015/0150547 A1 | 6/2015 | Ingmanson |
| 2015/0209035 A1 | 7/2015 | Zemlok |
| 2016/0058443 A1 | 3/2016 | Yates et al. |
| 2016/0095585 A1 | 4/2016 | Zergiebel et al. |
| 2016/0106401 A1 | 4/2016 | Beardsley |
| 2016/0175062 A1 | 6/2016 | Limon |
| 2016/0213436 A1 | 7/2016 | Inoue |
| 2016/0220247 A1 | 8/2016 | Timm et al. |
| 2016/0220268 A1 | 8/2016 | Shelton, IV et al. |
| 2016/0249922 A1 | 9/2016 | Morgan et al. |
| 2016/0270780 A1 | 9/2016 | Hall |
| 2016/0310134 A1* | 10/2016 | Contini ............ A61B 17/07207 |
| 2016/0361131 A1 | 12/2016 | Dachs, II |
| 2016/0374666 A1 | 12/2016 | DiNardo et al. |
| 2017/0007254 A1 | 1/2017 | Jaworek |
| 2017/0007255 A1 | 1/2017 | Jaworek et al. |
| 2017/0035421 A1 | 2/2017 | Marczyk |
| 2017/0066119 A1 | 3/2017 | Fu |
| 2017/0079640 A1 | 3/2017 | Overmyer et al. |
| 2017/0079642 A1 | 3/2017 | Overmyer et al. |
| 2017/0128071 A1 | 5/2017 | Holsten et al. |
| 2017/0164945 A1 | 6/2017 | Chowaniec |
| 2017/0172574 A1 | 6/2017 | Zemlok et al. |
| 2017/0189020 A1 | 7/2017 | Harris et al. |
| 2017/0202607 A1 | 7/2017 | Shelton, IV |
| 2017/0207467 A1 | 7/2017 | Shelton, IV |
| 2017/0281167 A1 | 10/2017 | Shelton, IV et al. |
| 2017/0290583 A1 | 10/2017 | Reed et al. |
| 2017/0296176 A1 | 10/2017 | Contini et al. |
| 2018/0000483 A1 | 1/2018 | Leimbach et al. |
| 2018/0056496 A1 | 3/2018 | Rubens |
| 2018/0110519 A1 | 4/2018 | Lytle, IV et al. |
| 2018/0133883 A1 | 5/2018 | Nicholas et al. |
| 2018/0250002 A1 | 9/2018 | Eschbach |
| 2018/0317964 A1 | 11/2018 | Evans et al. |
| 2018/0340806 A1 | 11/2018 | Zemlok |
| 2018/0360486 A1 | 12/2018 | Beaupre |
| 2018/0368822 A1 | 12/2018 | Shelton et al. |
| 2019/0000577 A1 | 1/2019 | Shelton |
| 2019/0008512 A1 | 1/2019 | Nicholas et al. |
| 2019/0038283 A1 | 2/2019 | Shelton, IV |
| 2019/0053796 A1 | 2/2019 | Miller et al. |
| 2019/0059923 A1 | 2/2019 | Tillman |
| 2019/0069887 A1 | 3/2019 | Satti, III et al. |
| 2019/0069895 A1 | 3/2019 | Satti, III et al. |
| 2019/0069896 A1 | 3/2019 | Satti, III et al. |
| 2019/0069917 A1 | 3/2019 | Sholev |
| 2019/0117222 A1 | 4/2019 | Shelton, IV et al. |
| 2019/0142421 A1 | 5/2019 | Shelton, IV |
| 2019/0142423 A1 | 5/2019 | Satti, III |
| 2019/0183594 A1 | 6/2019 | Shelton, IV et al. |
| 2019/0239966 A1 | 8/2019 | Xu |
| 2019/0261991 A1 | 8/2019 | Beckman |
| 2020/0205817 A1 | 7/2020 | Nielsen et al. |
| 2020/0315725 A1 | 10/2020 | Graves et al. |
| 2021/0322007 A1 | 10/2021 | Satti, III |
| 2022/0061836 A1 | 3/2022 | Parihar |

FOREIGN PATENT DOCUMENTS

| | | |
|---|---|---|
| EP | 0699418 | 3/1996 |
| EP | 0705571 | 4/1996 |
| EP | 1889576 | 2/2008 |
| EP | 2243432 | 10/2010 |
| EP | 2243433 | 10/2010 |
| EP | 3005954 | 4/2016 |
| EP | 3078334 | 10/2016 |
| EP | 3178413 | 6/2017 |
| EP | 3189790 | 7/2017 |
| EP | 2792316 | 1/2018 |
| JP | 5415704 B2 | 11/2013 |
| WO | WO 2006/112849 | 10/2006 |
| WO | WO 2010/006057 | 1/2010 |
| WO | WO 2017/154007 | 9/2017 |
| WO | WO 2019/045995 | 3/2019 |
| WO | WO 2019/046132 | 3/2019 |
| WO | WO 2021/016006 | 1/2021 |

OTHER PUBLICATIONS

International search report and written opinion for international application PCT/US2018/048020 dated Oct. 30, 2018.
International search report for international application PCT/US2018/046370 dated Nov. 6, 2018.
International search report and written opinion for international application PCT/US2020/018714 dated Aug. 4, 2020.
International Search Report and Written Opinion dated Nov. 13, 2020 for International Application No. PCT/US2020/042033.
International search report and written opinion for international application PCT/US2022/016892 dated May 13, 2022.

(56) References Cited

OTHER PUBLICATIONS

Search Report For European Application EP 18849700 dated Jun. 8, 2021.

* cited by examiner

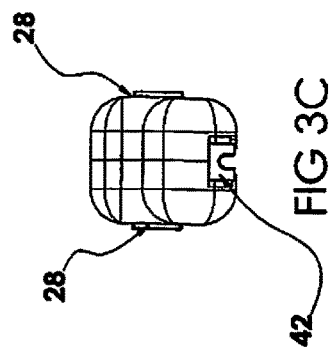
FIG 3C
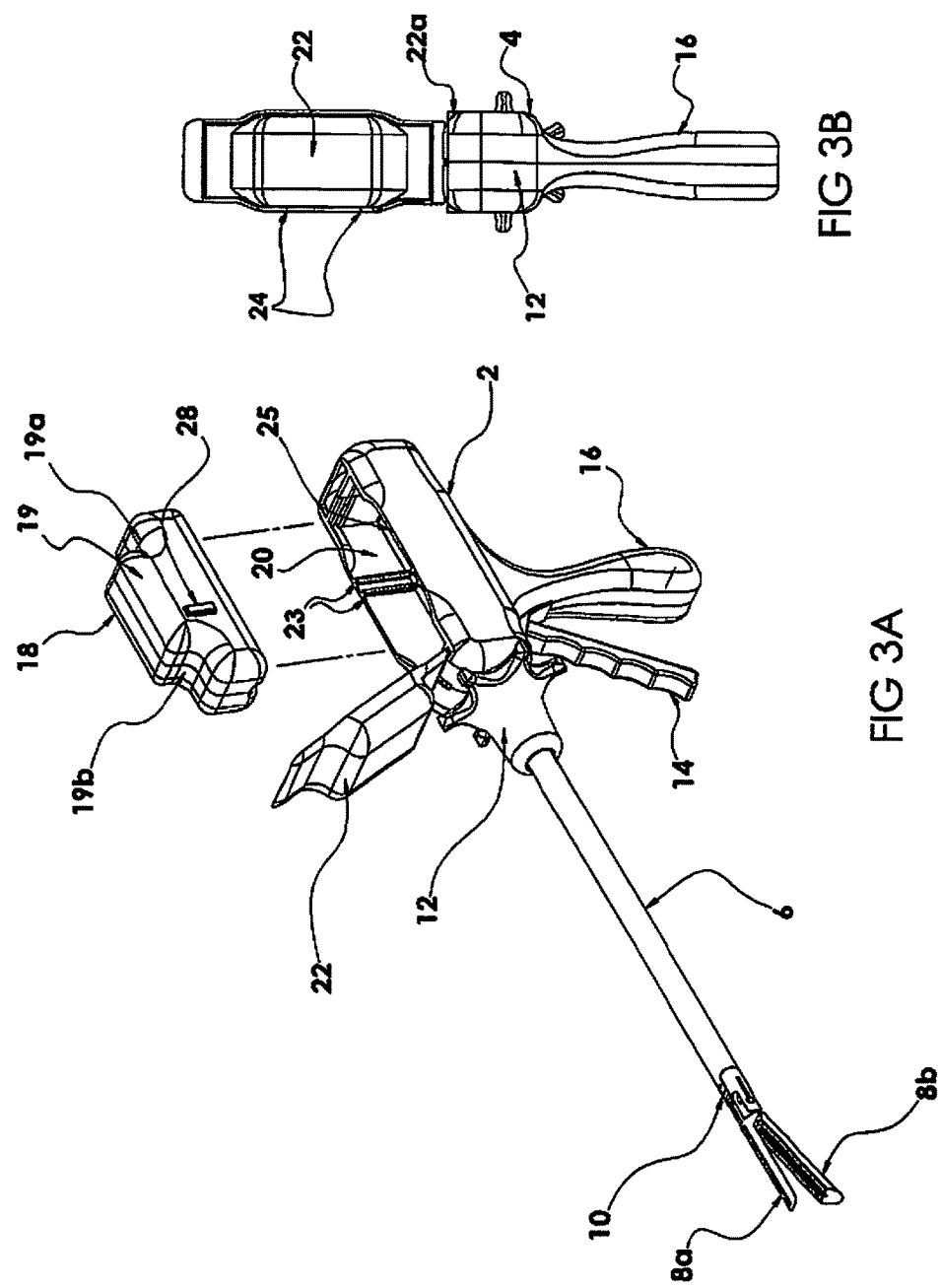
FIG 3B
FIG 3A

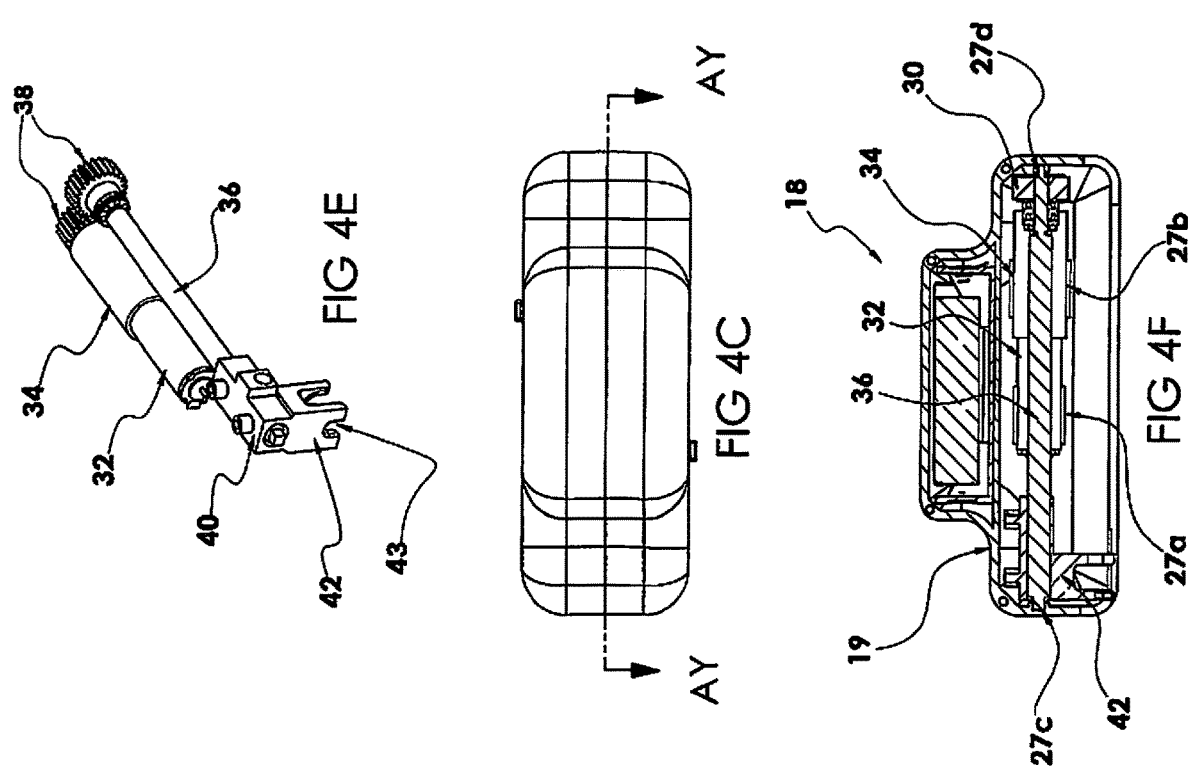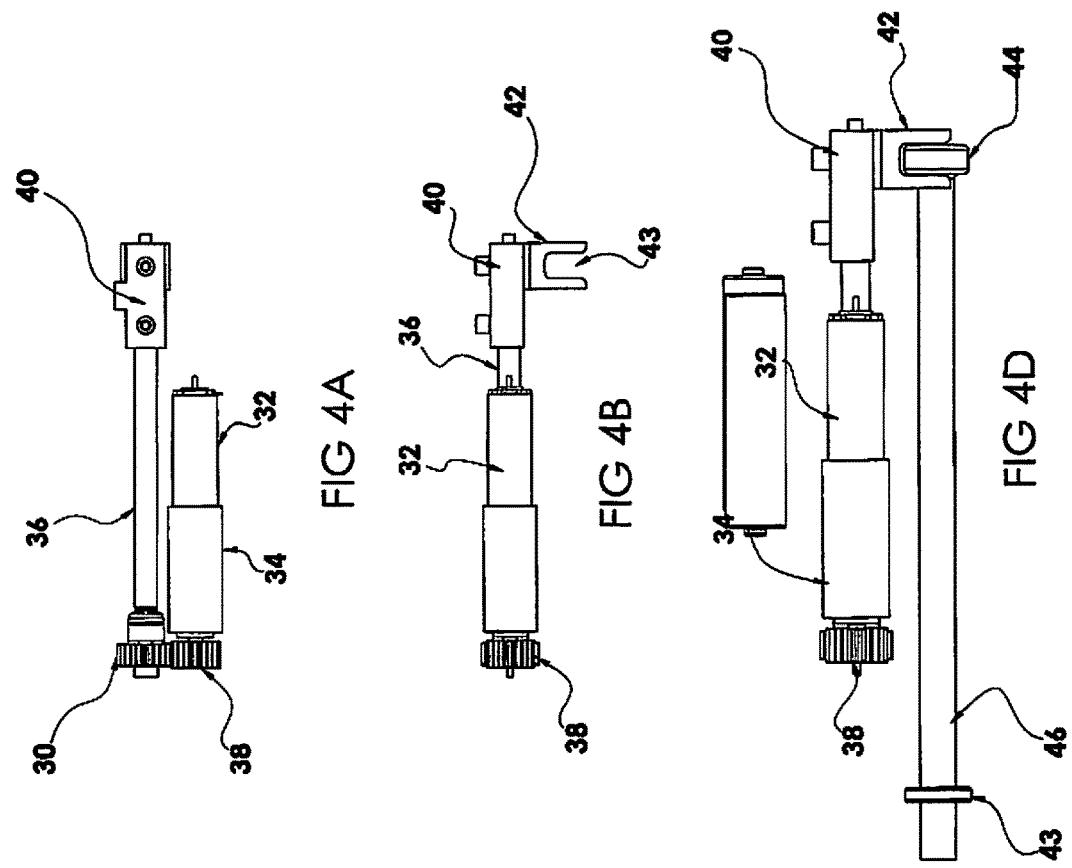

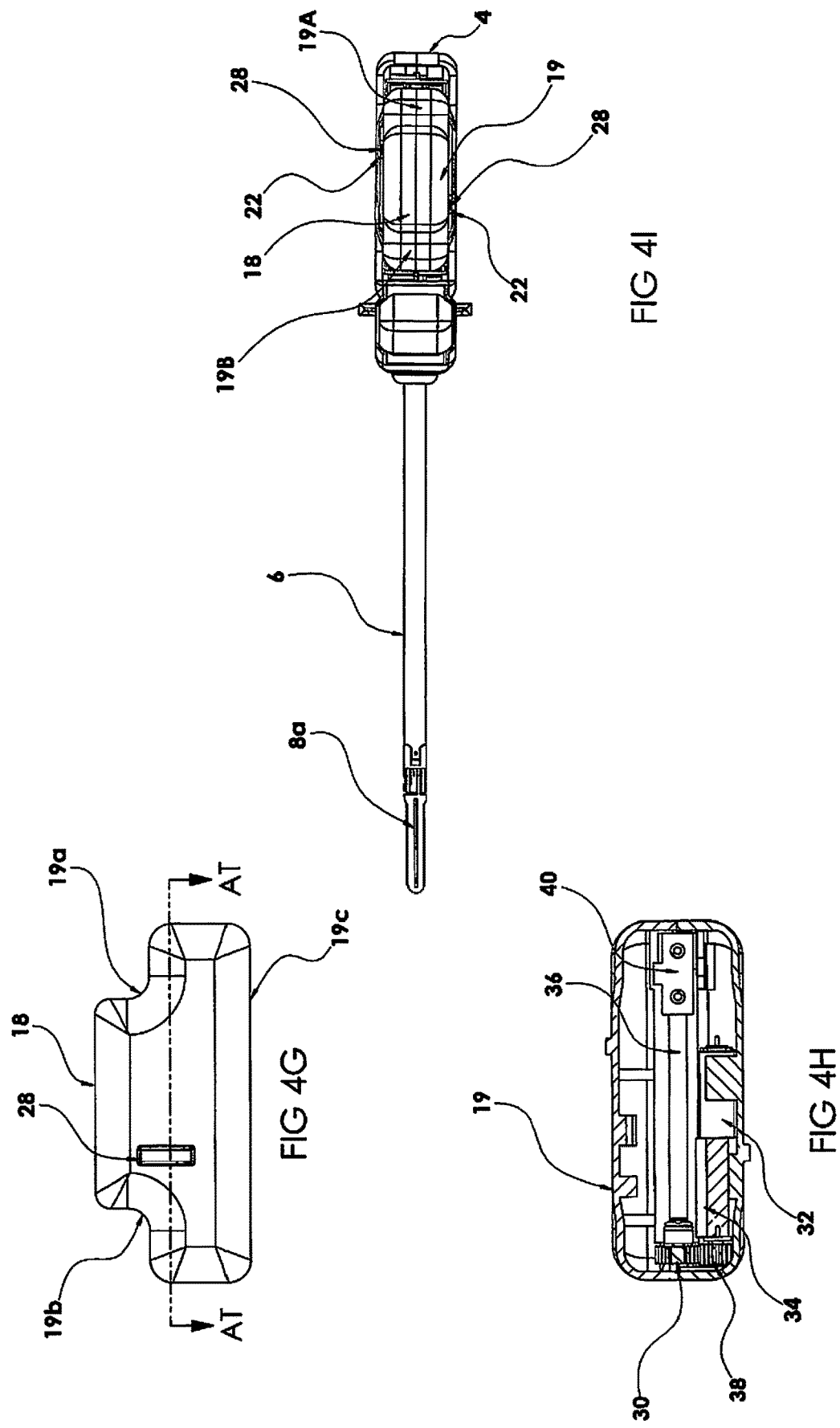

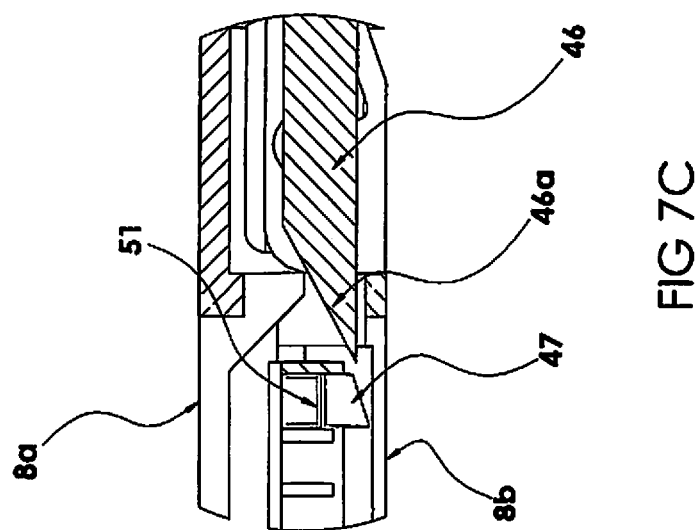
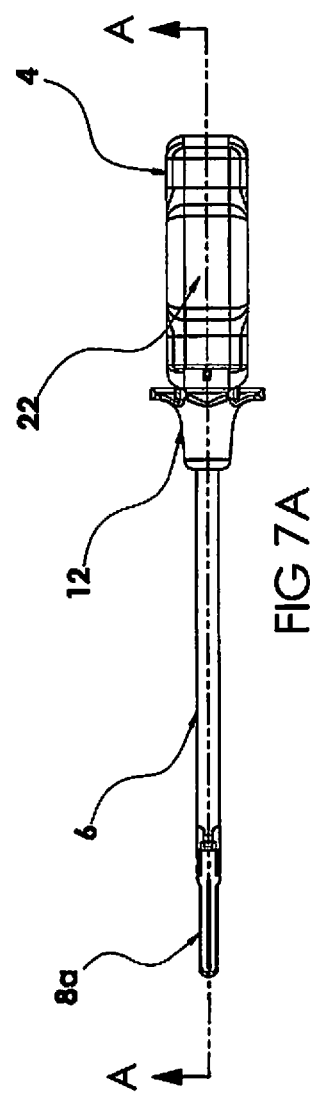
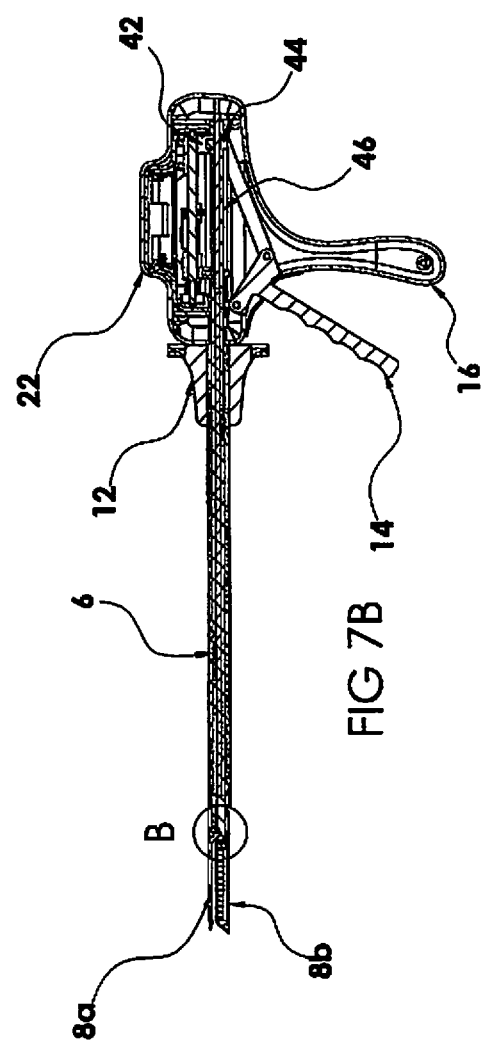

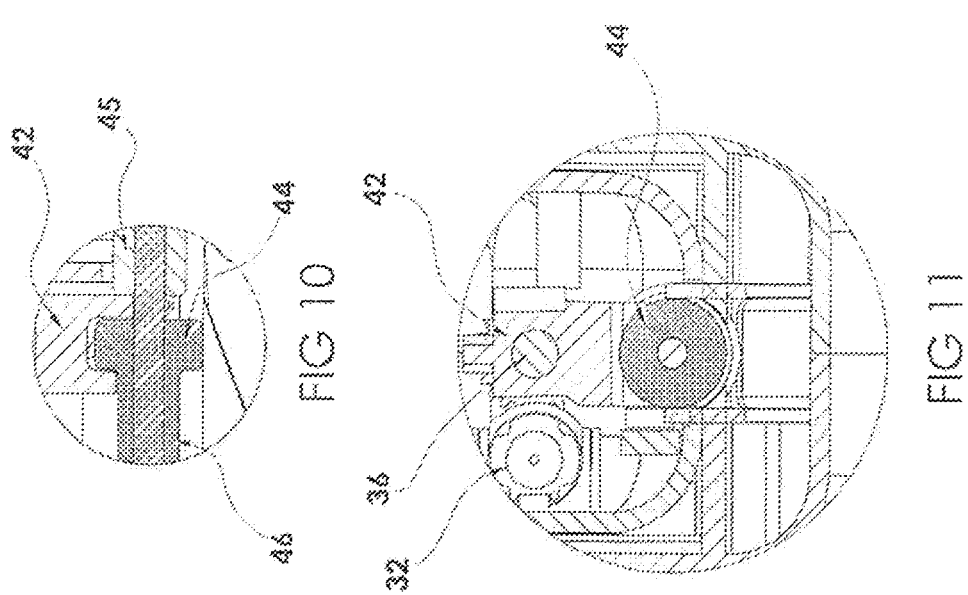
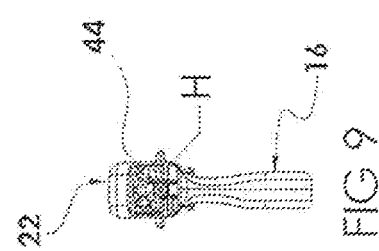
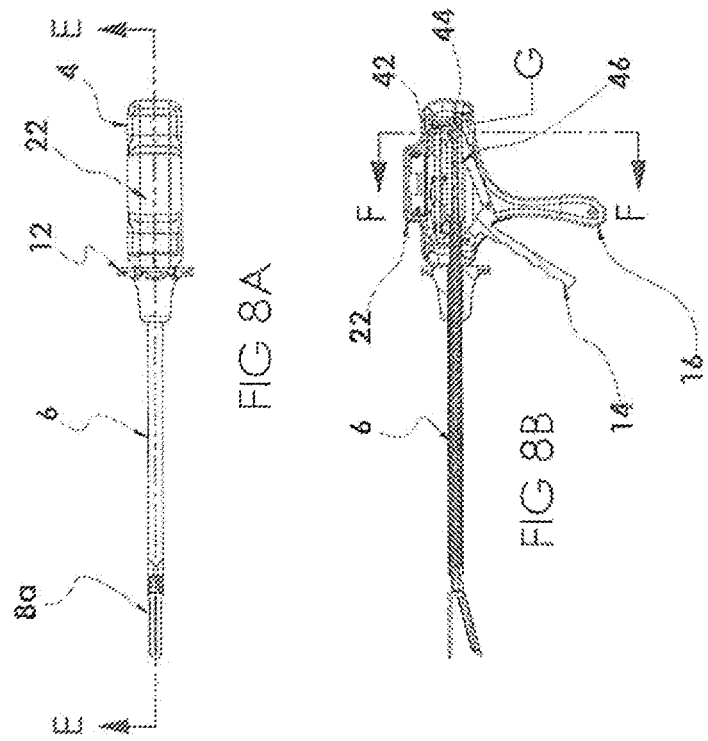

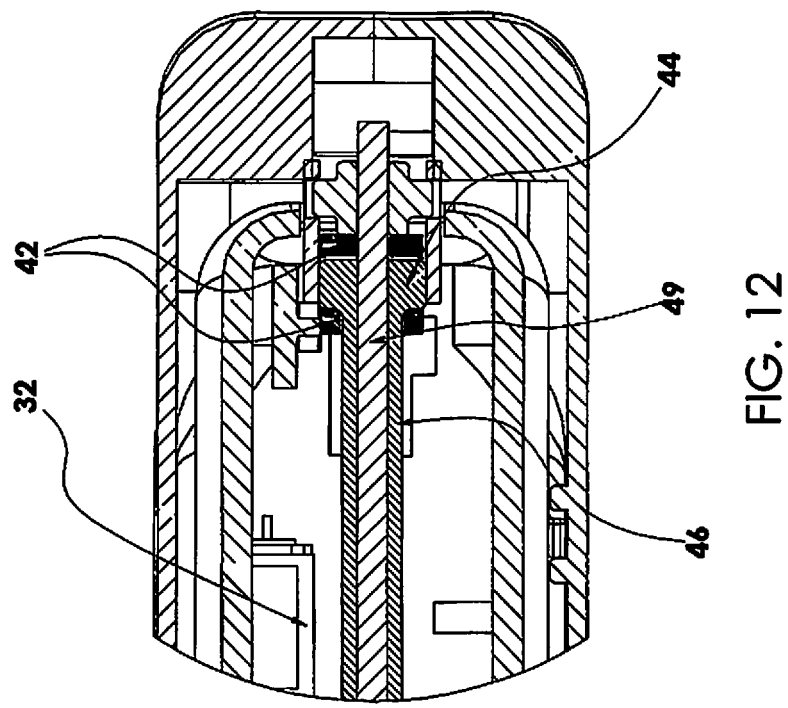
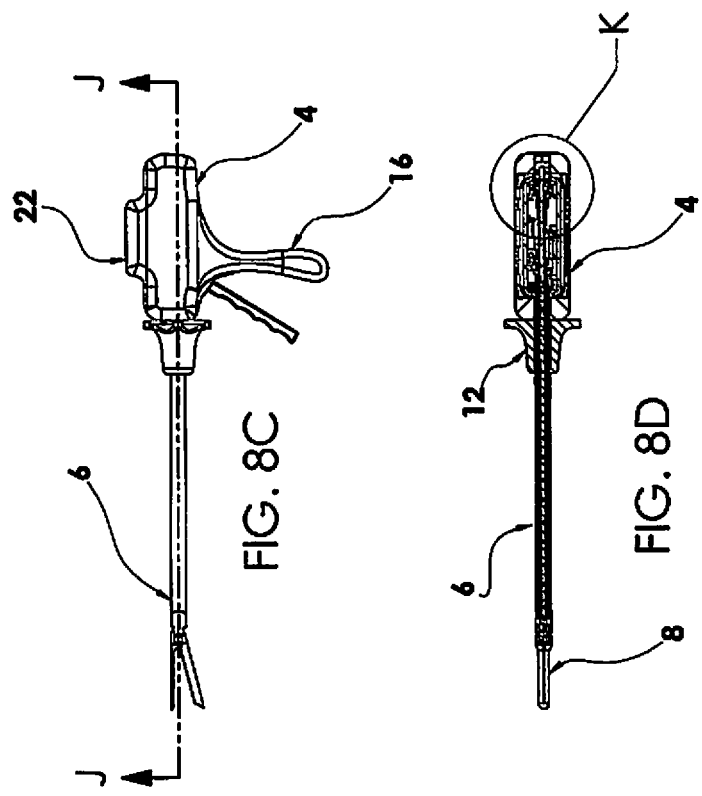

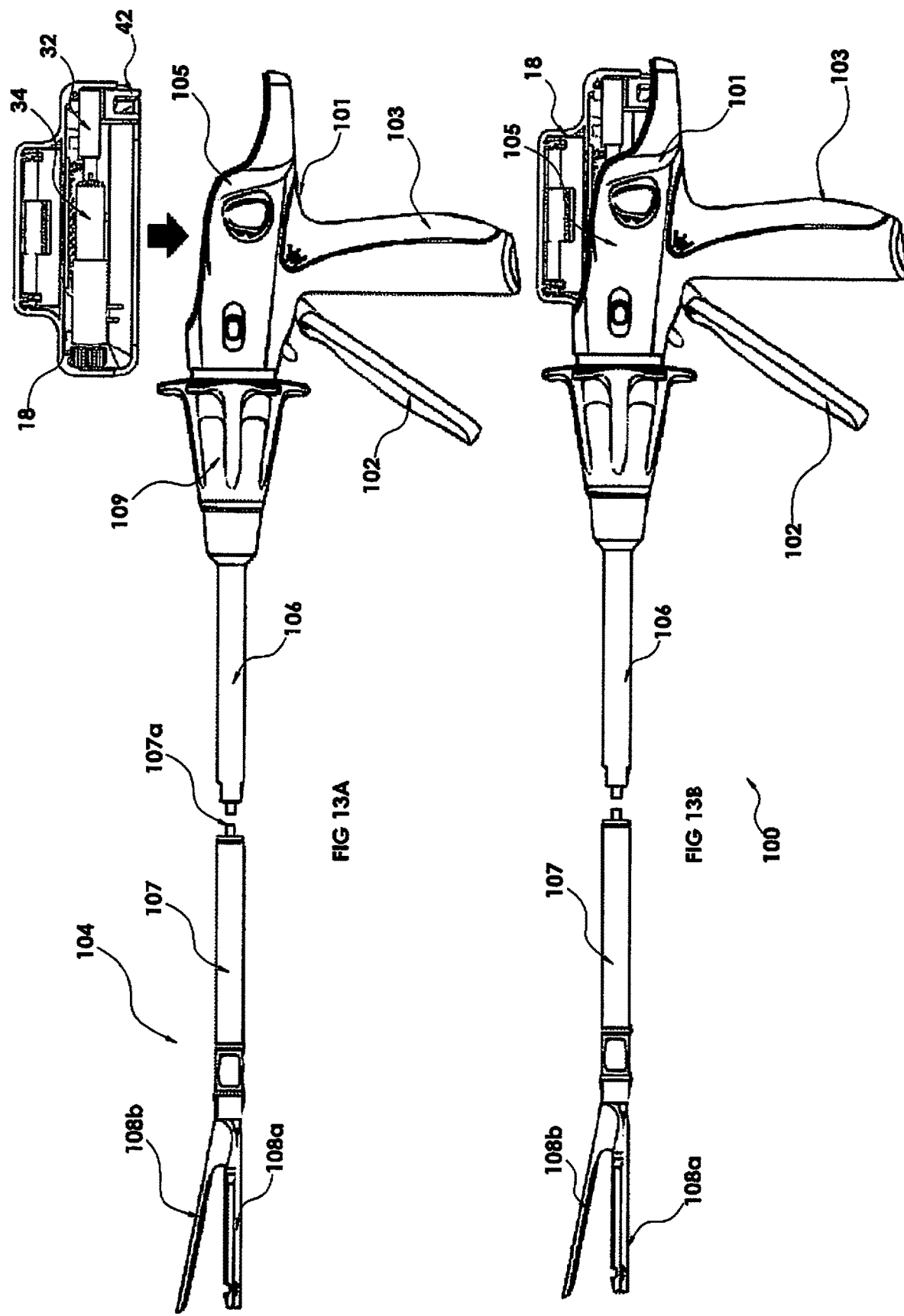

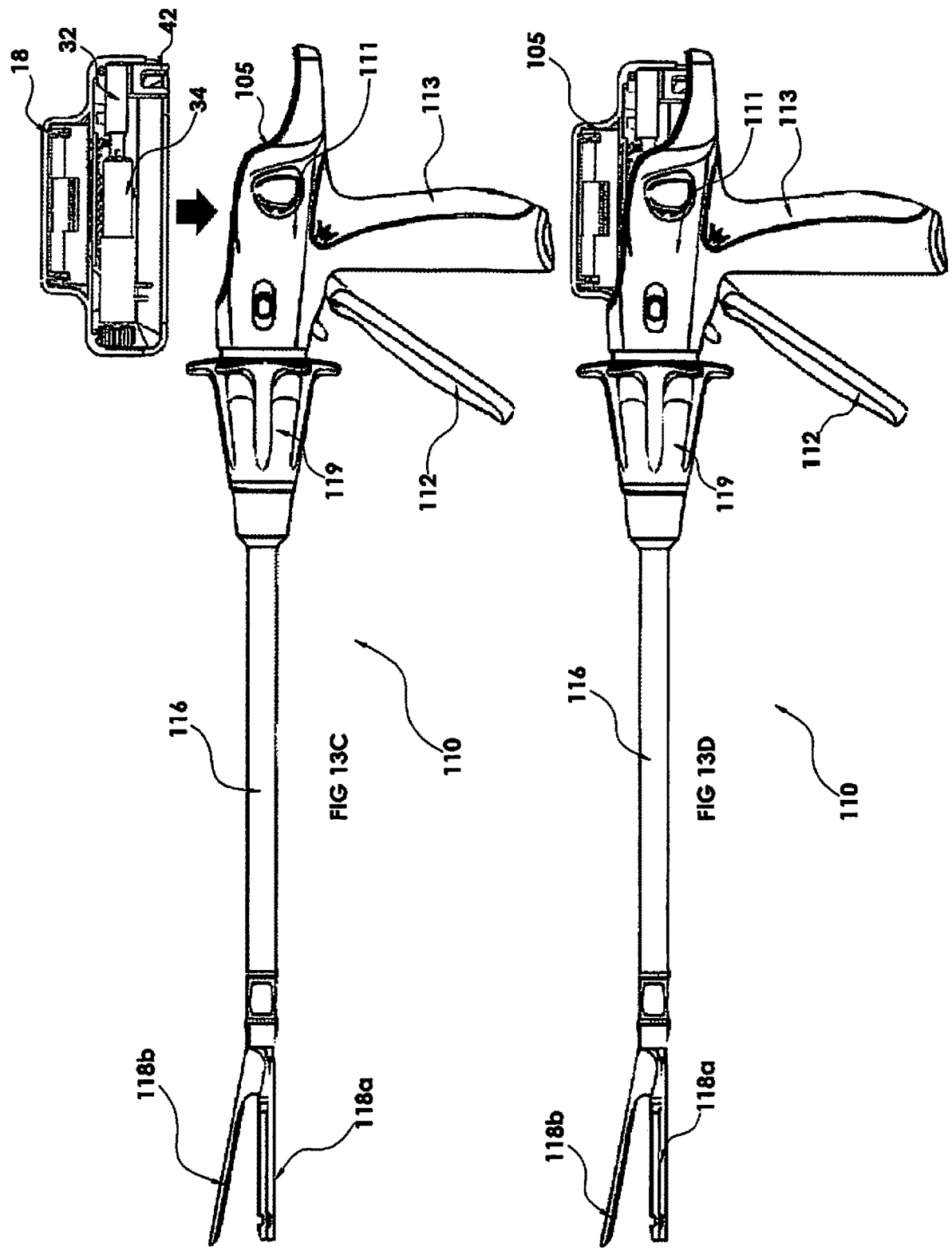

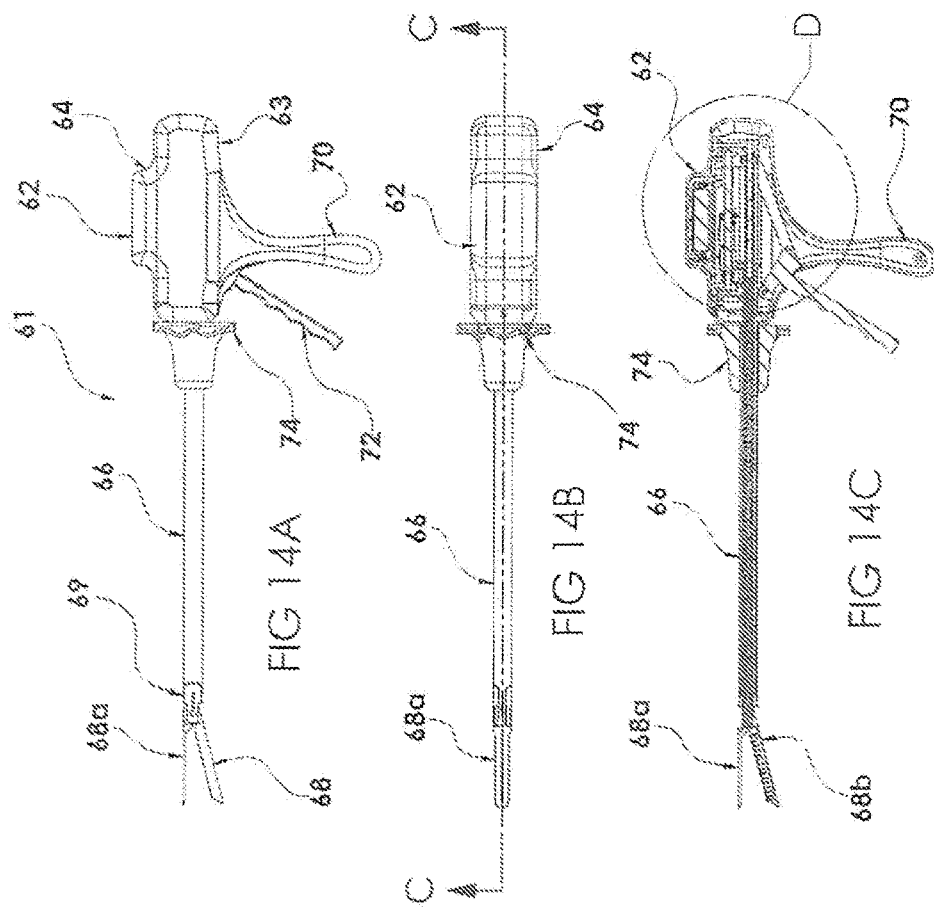

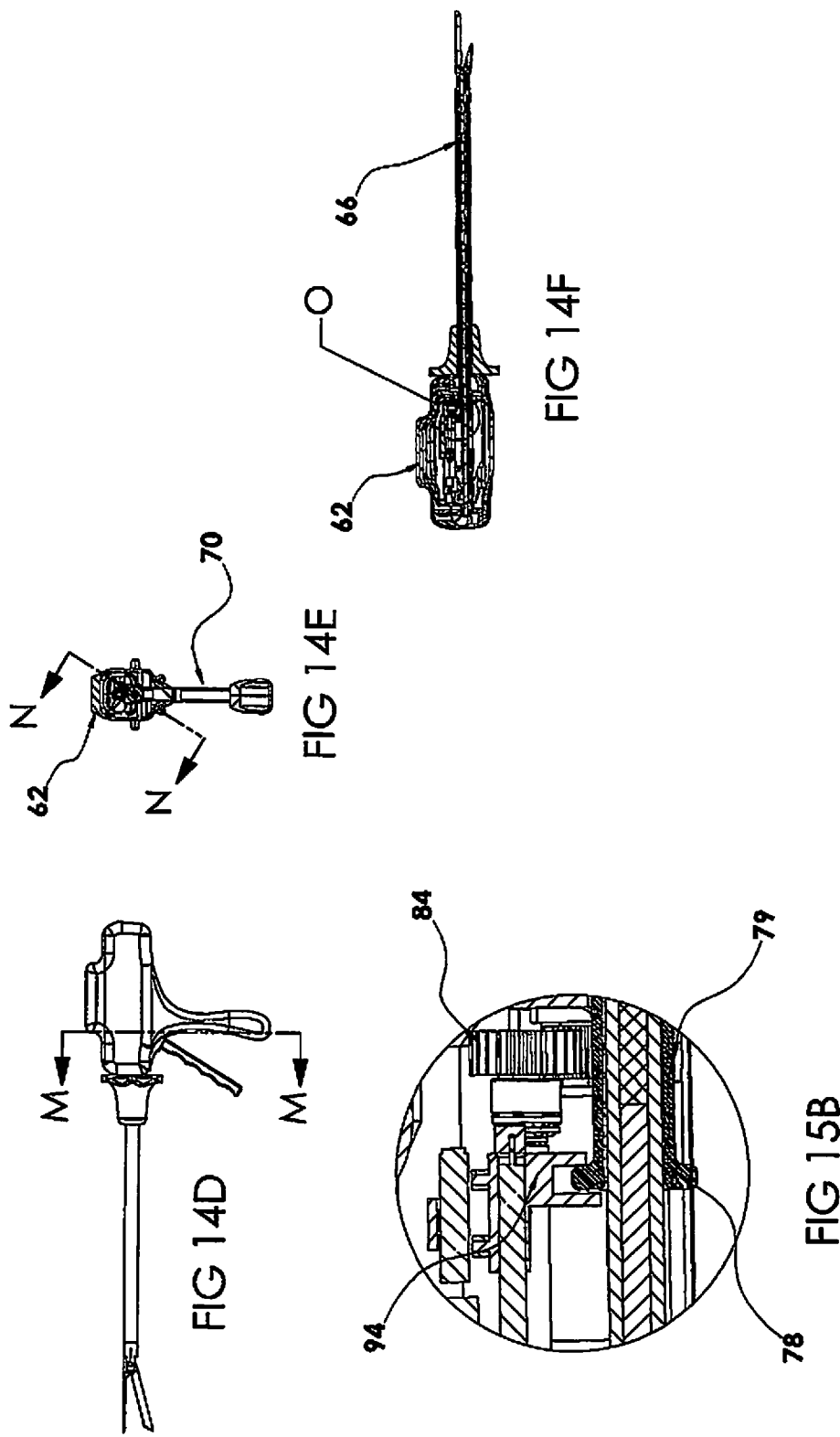

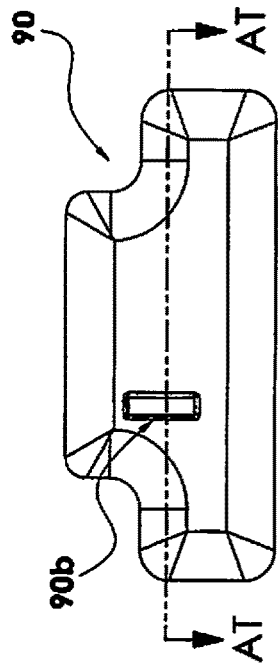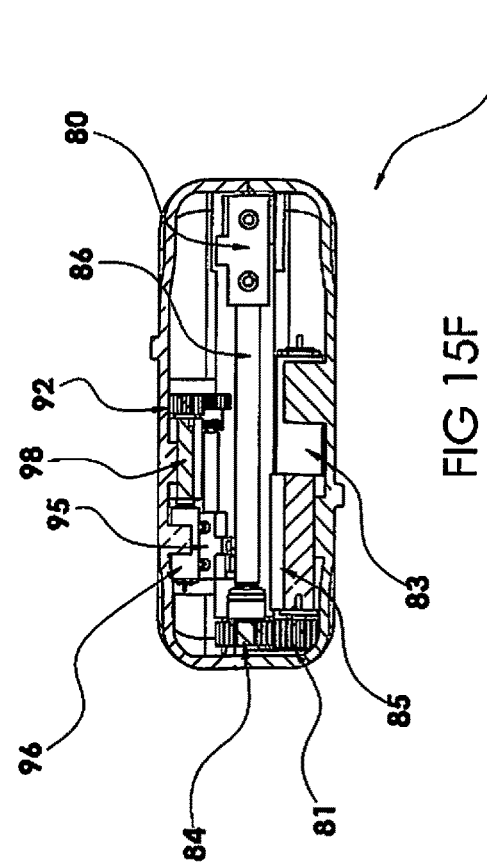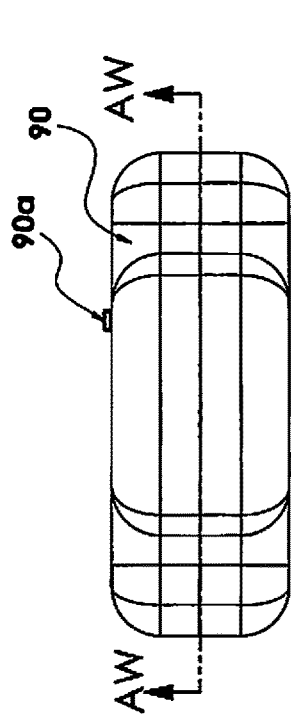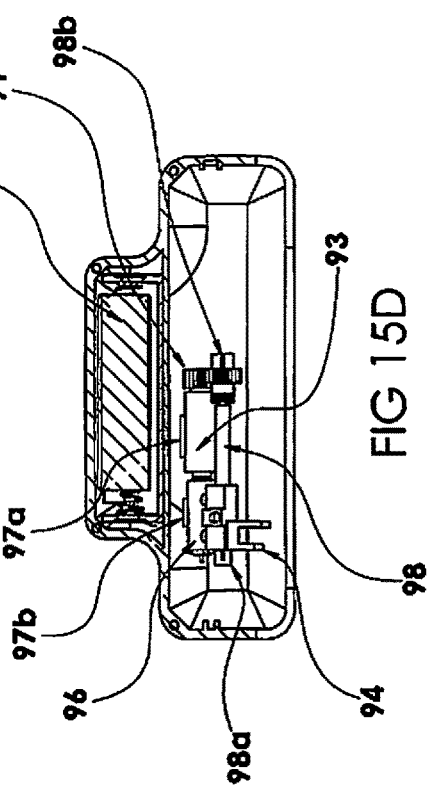

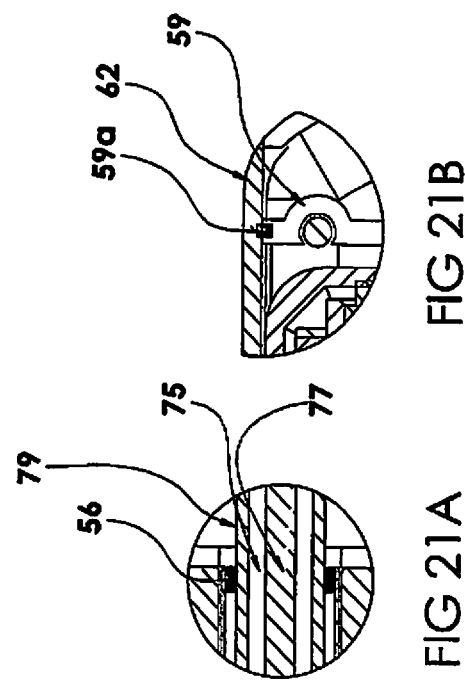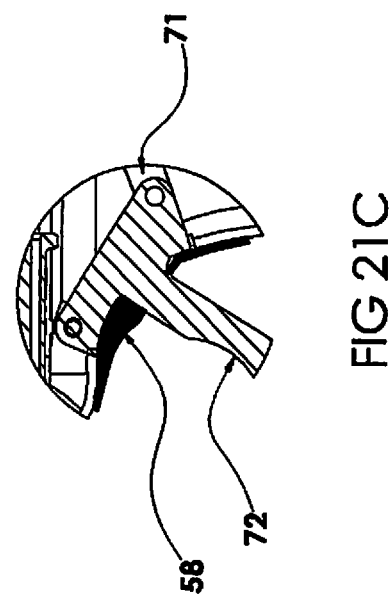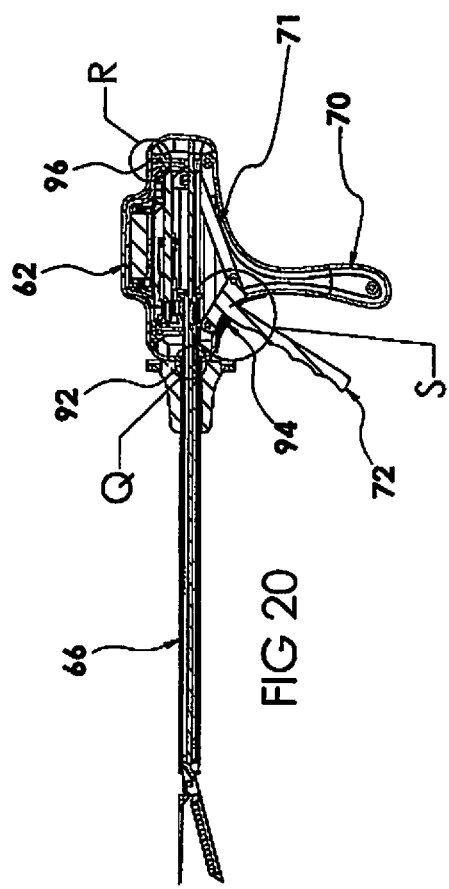

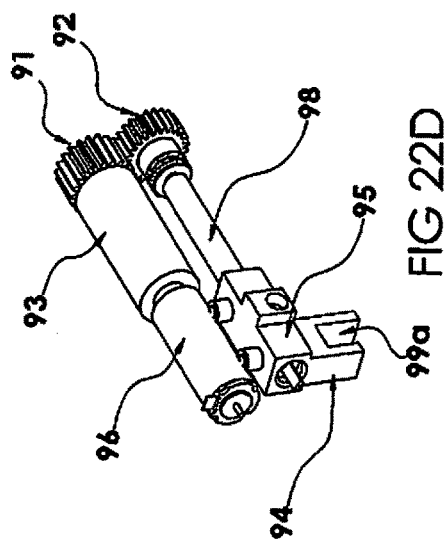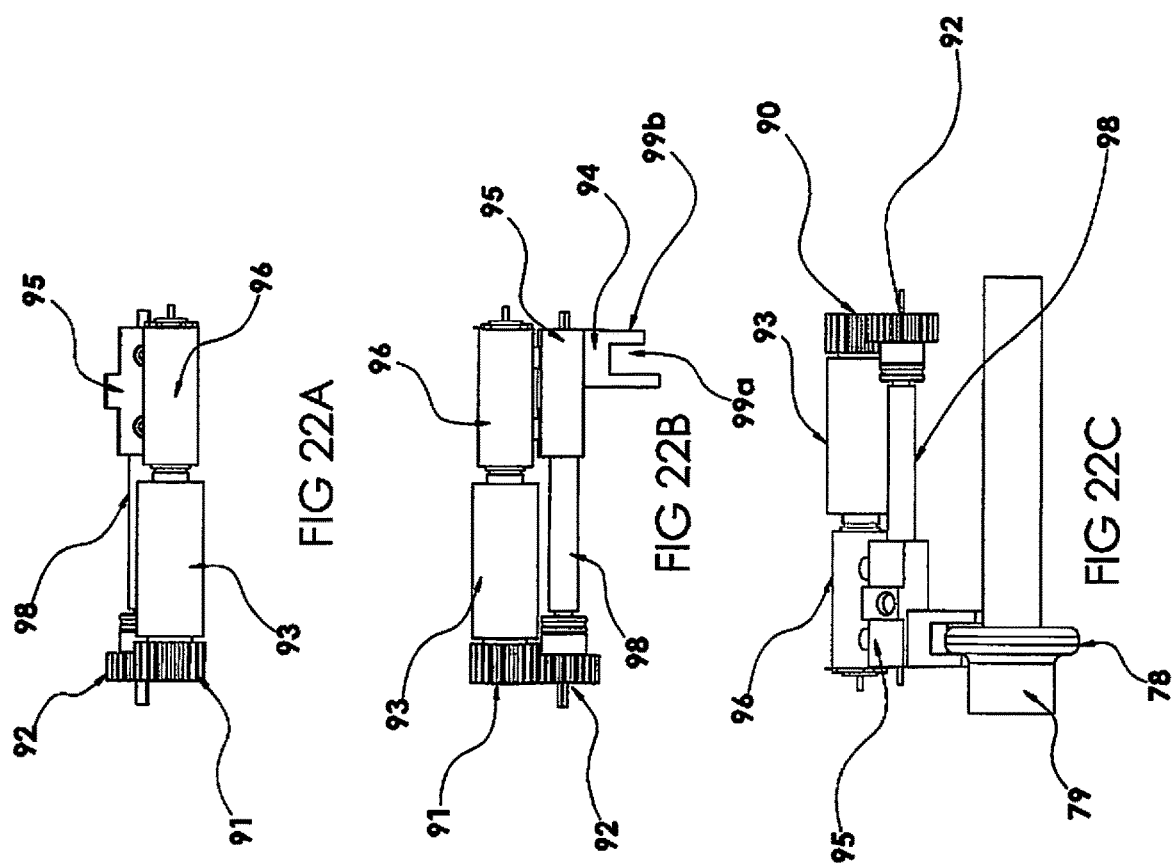

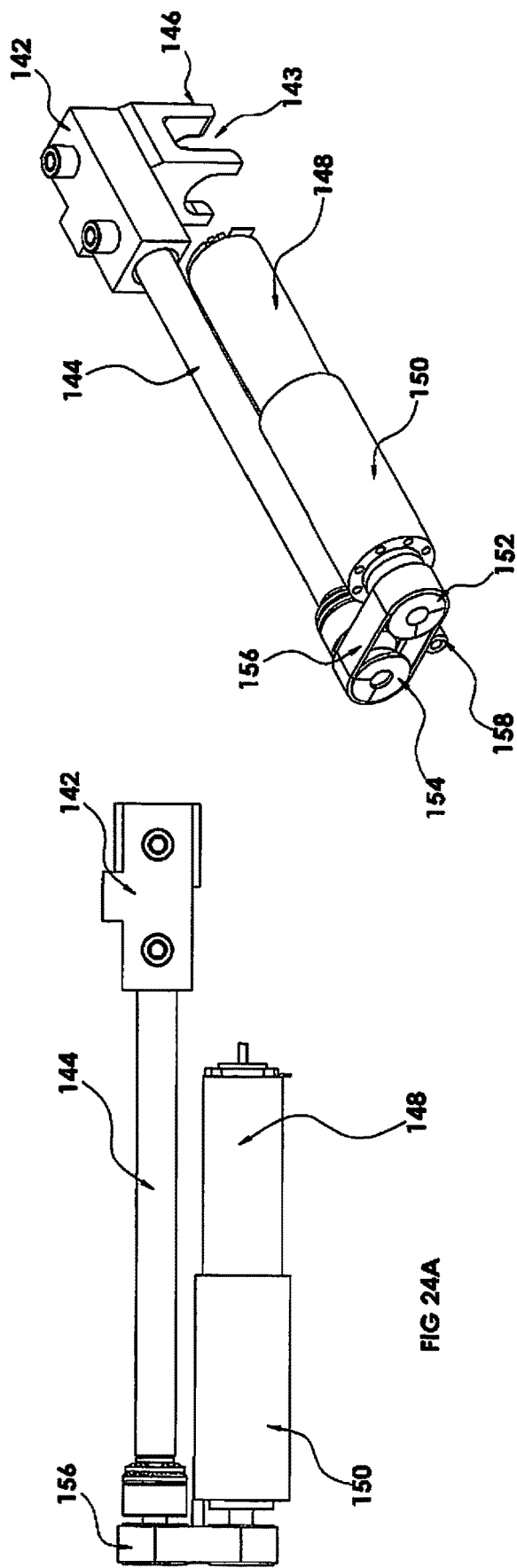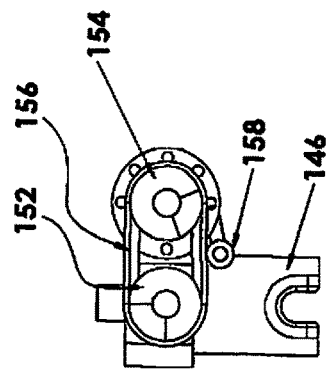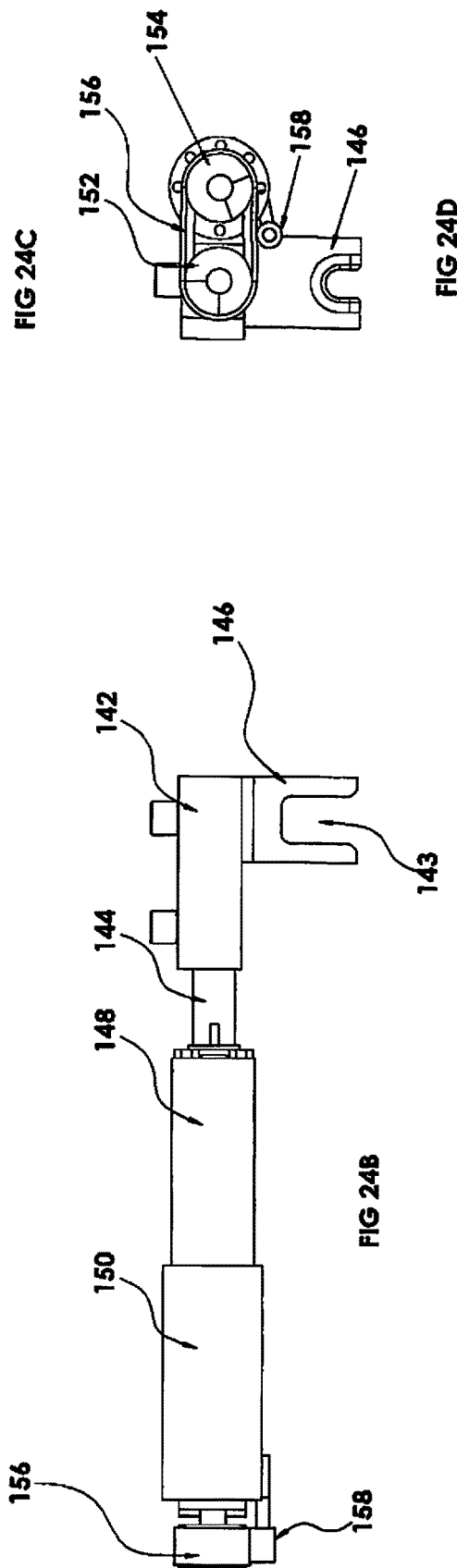

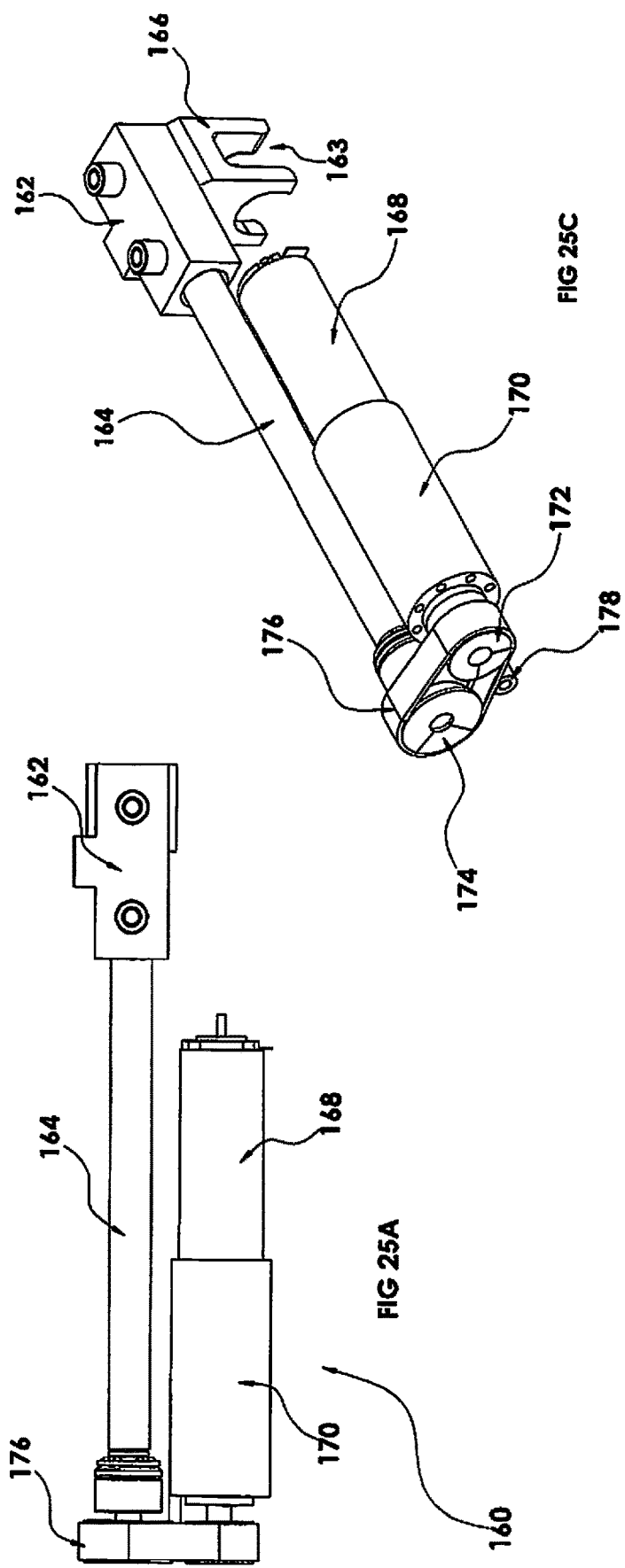

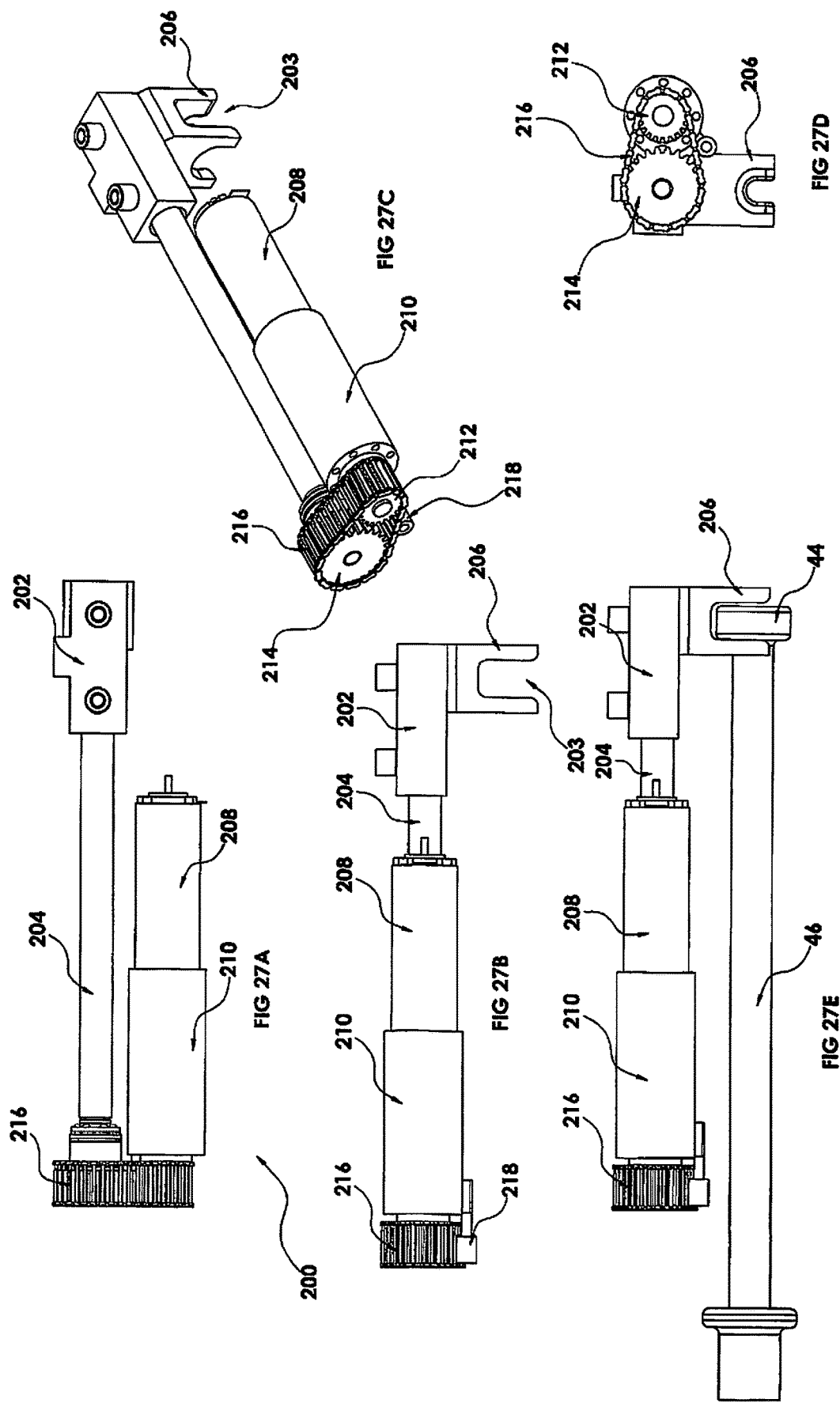

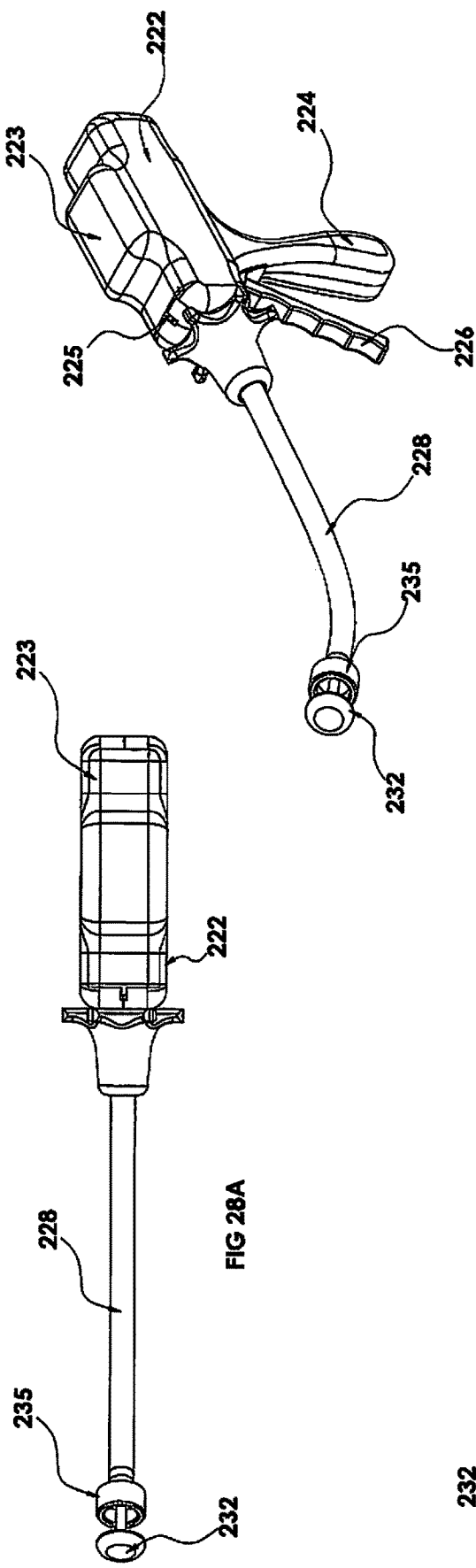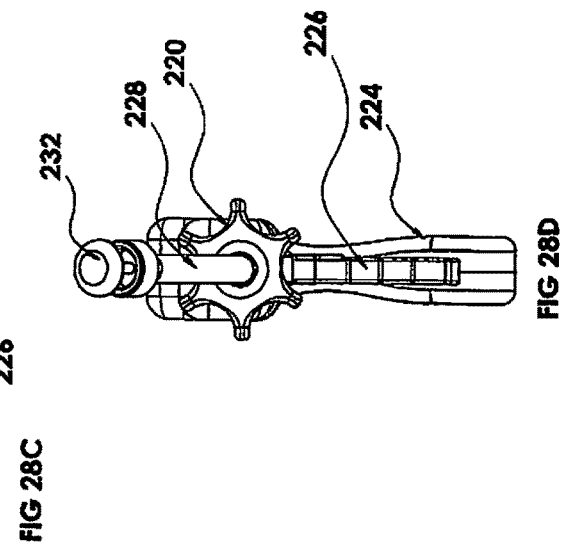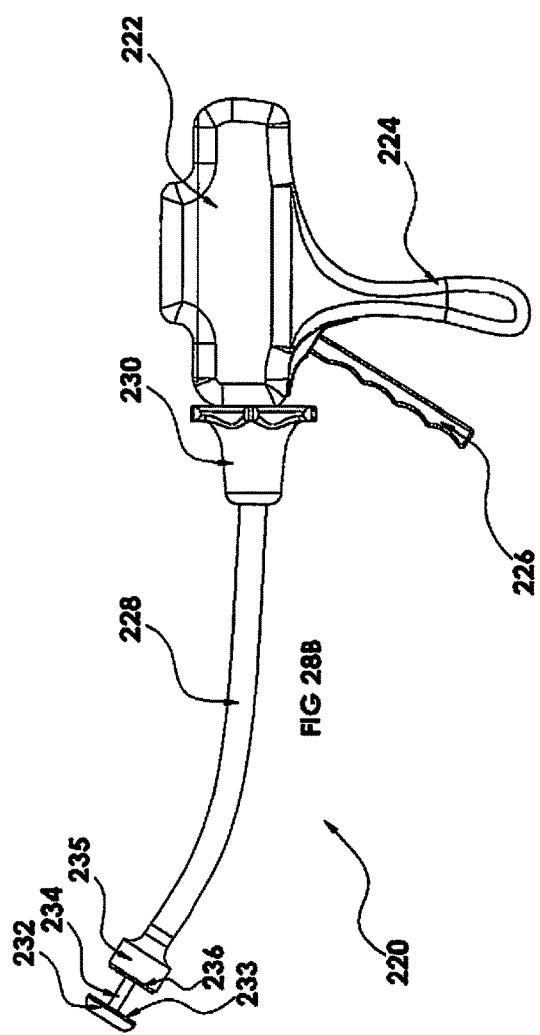

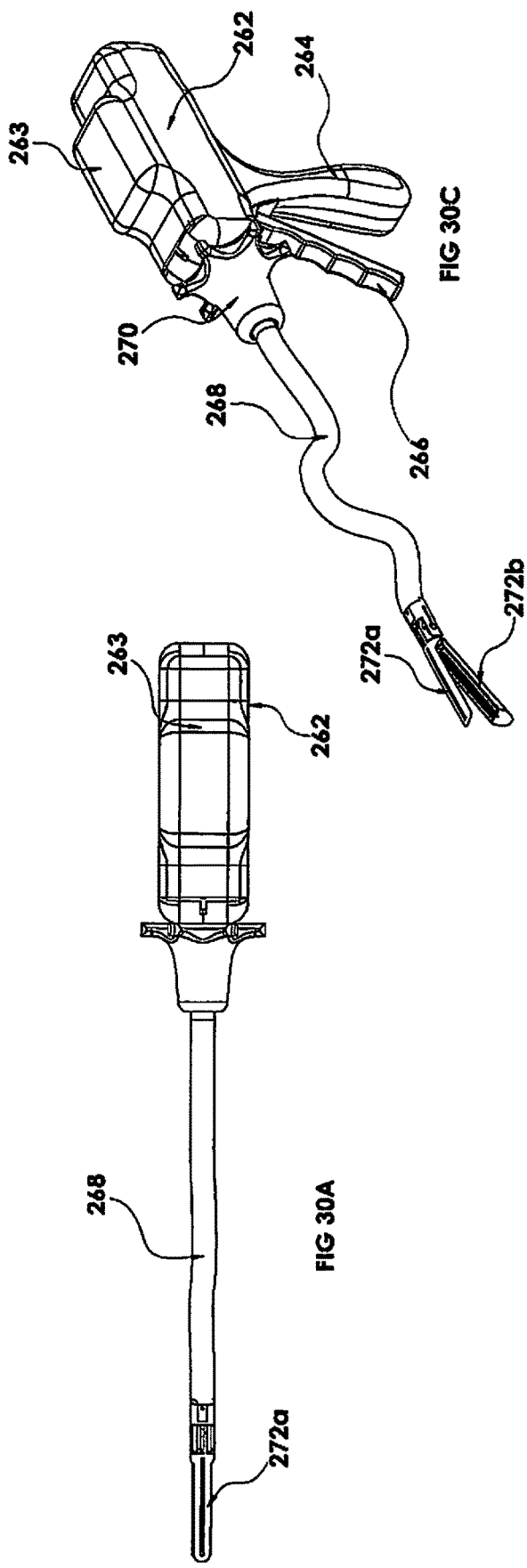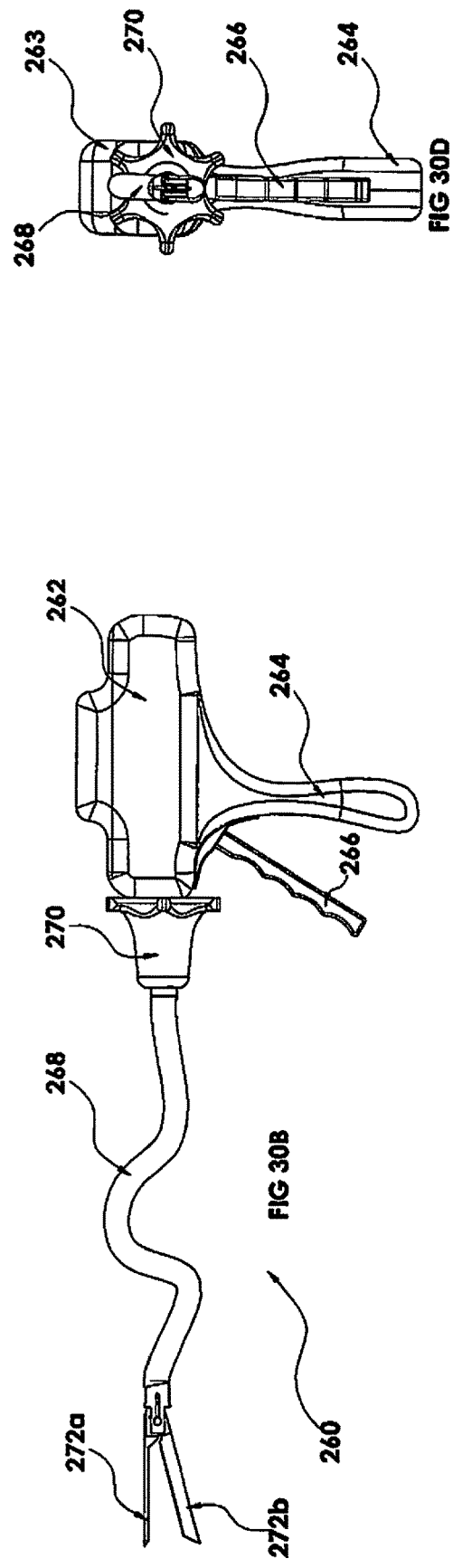

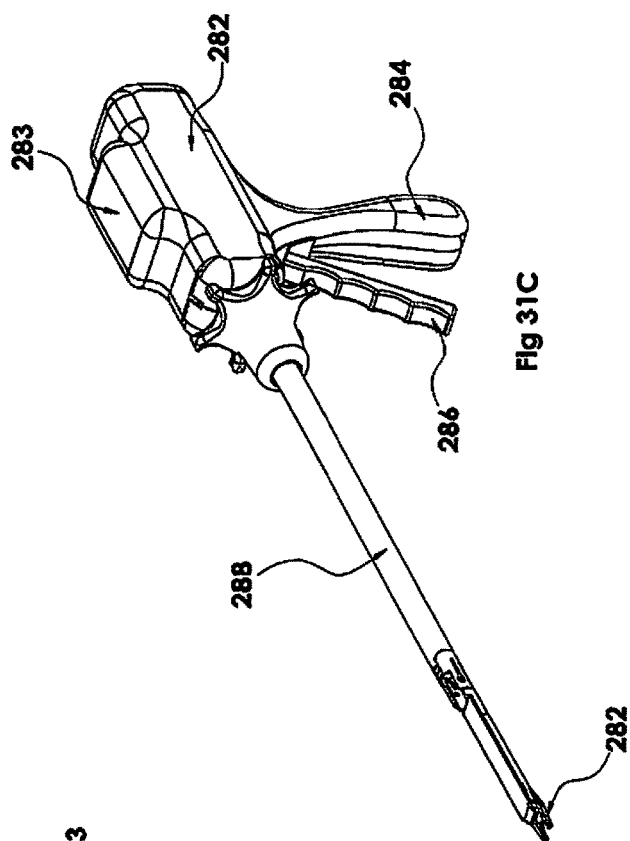
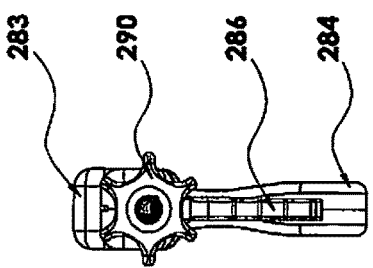
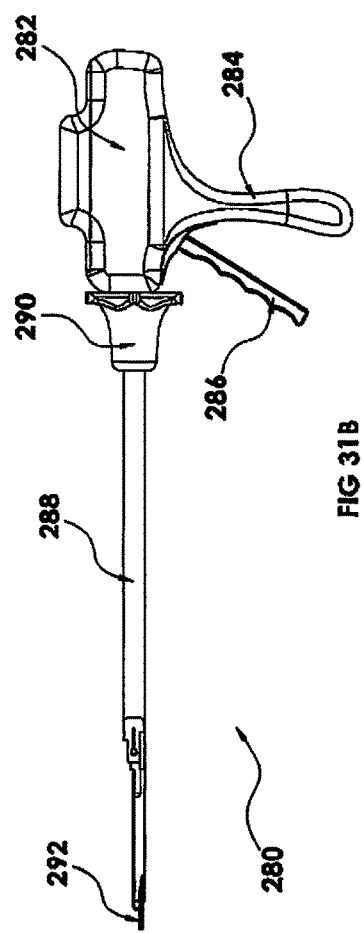

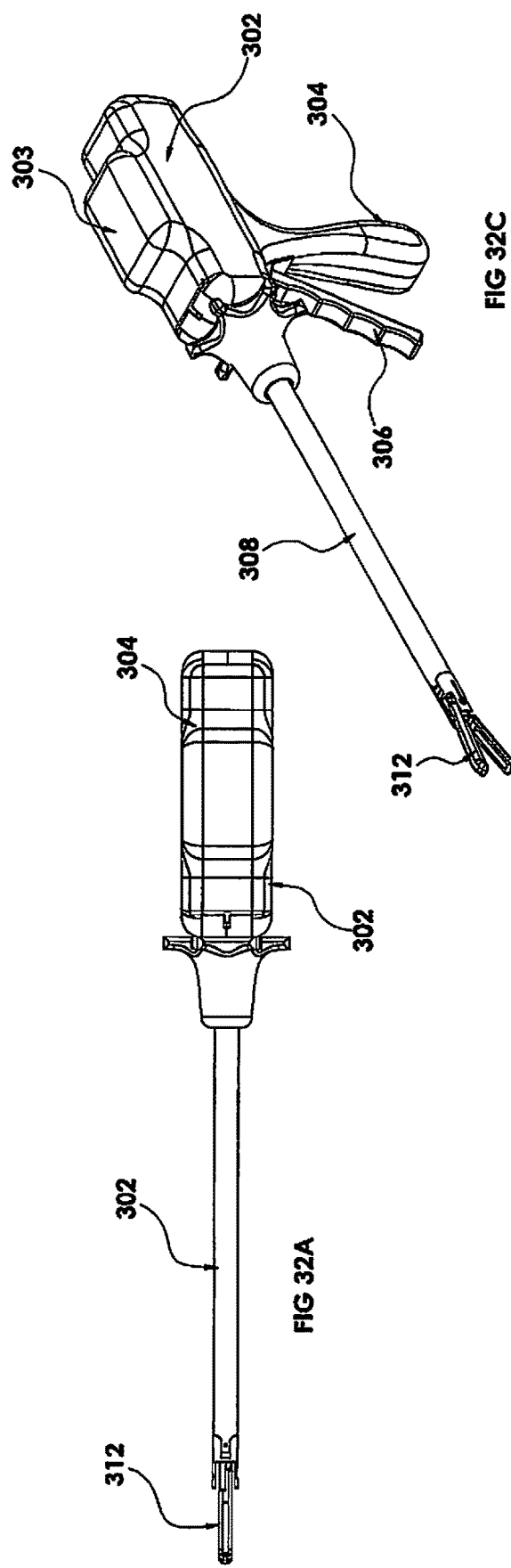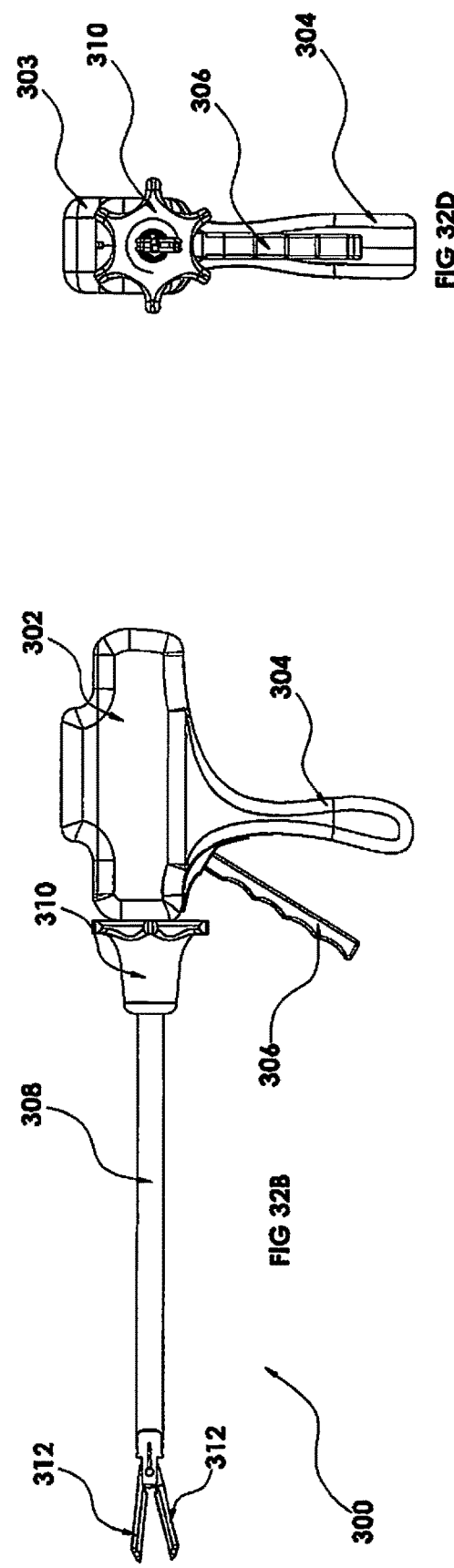

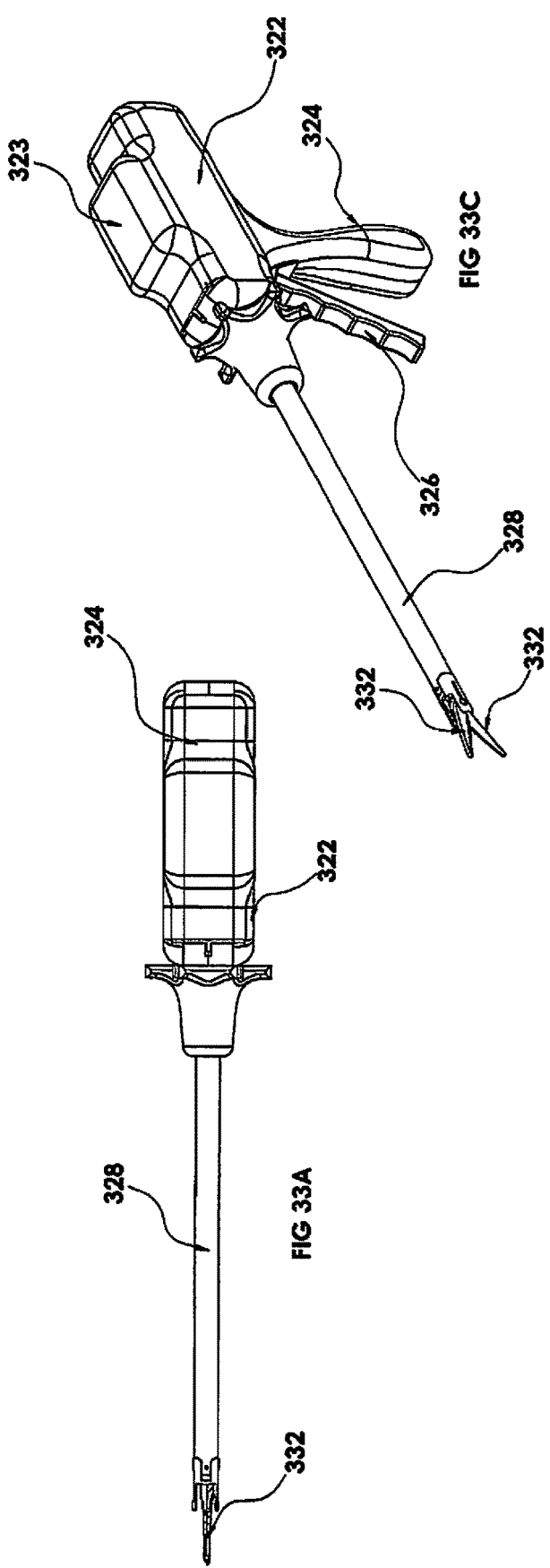

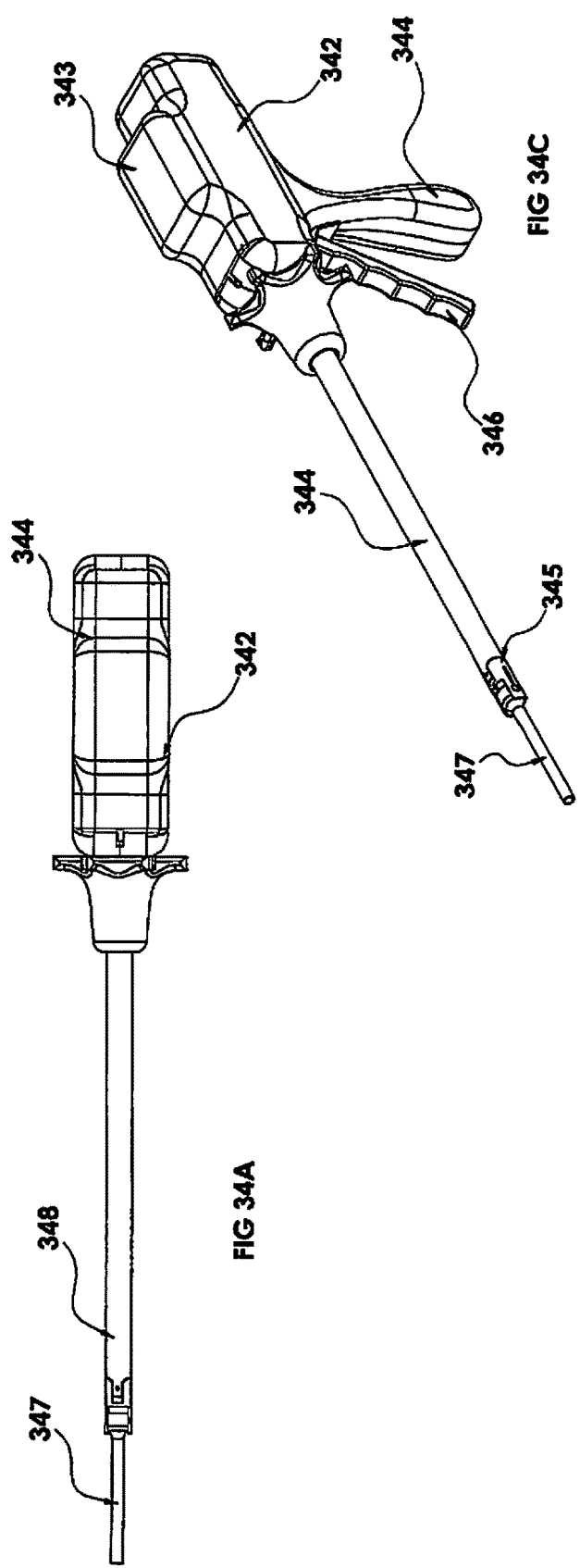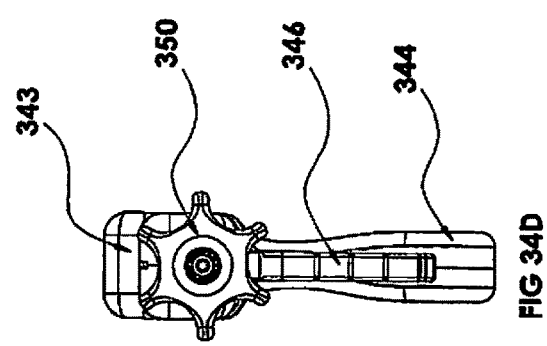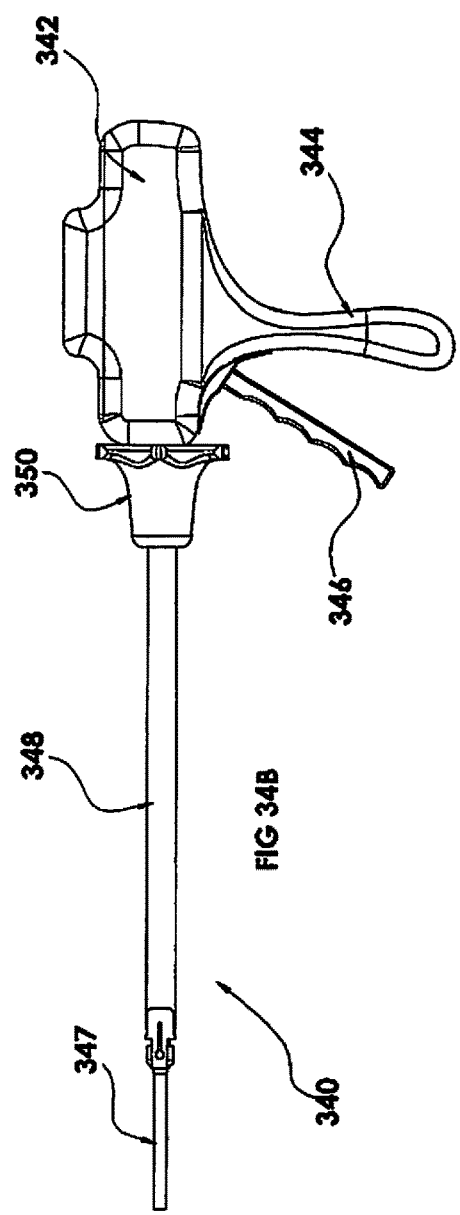

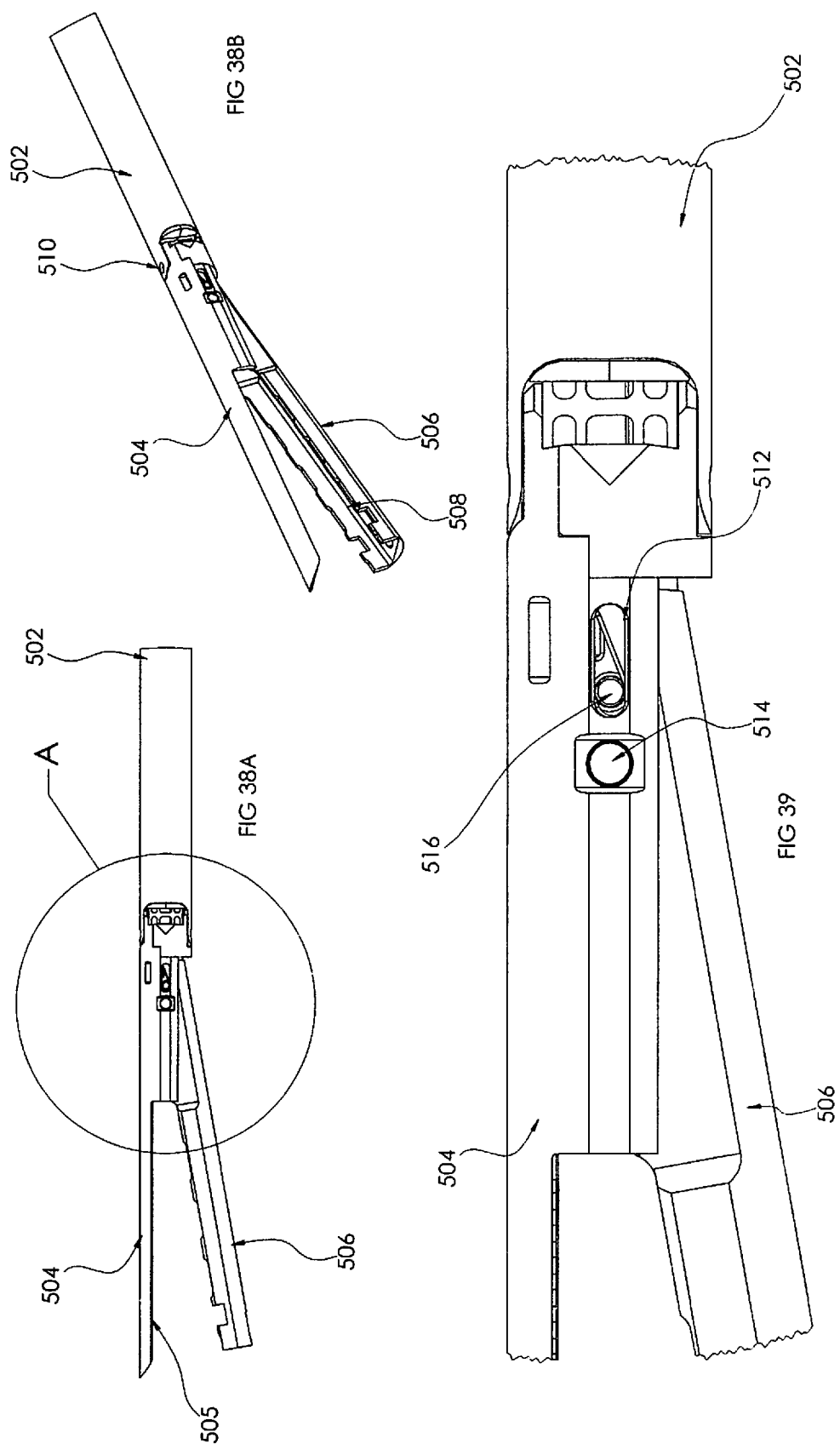

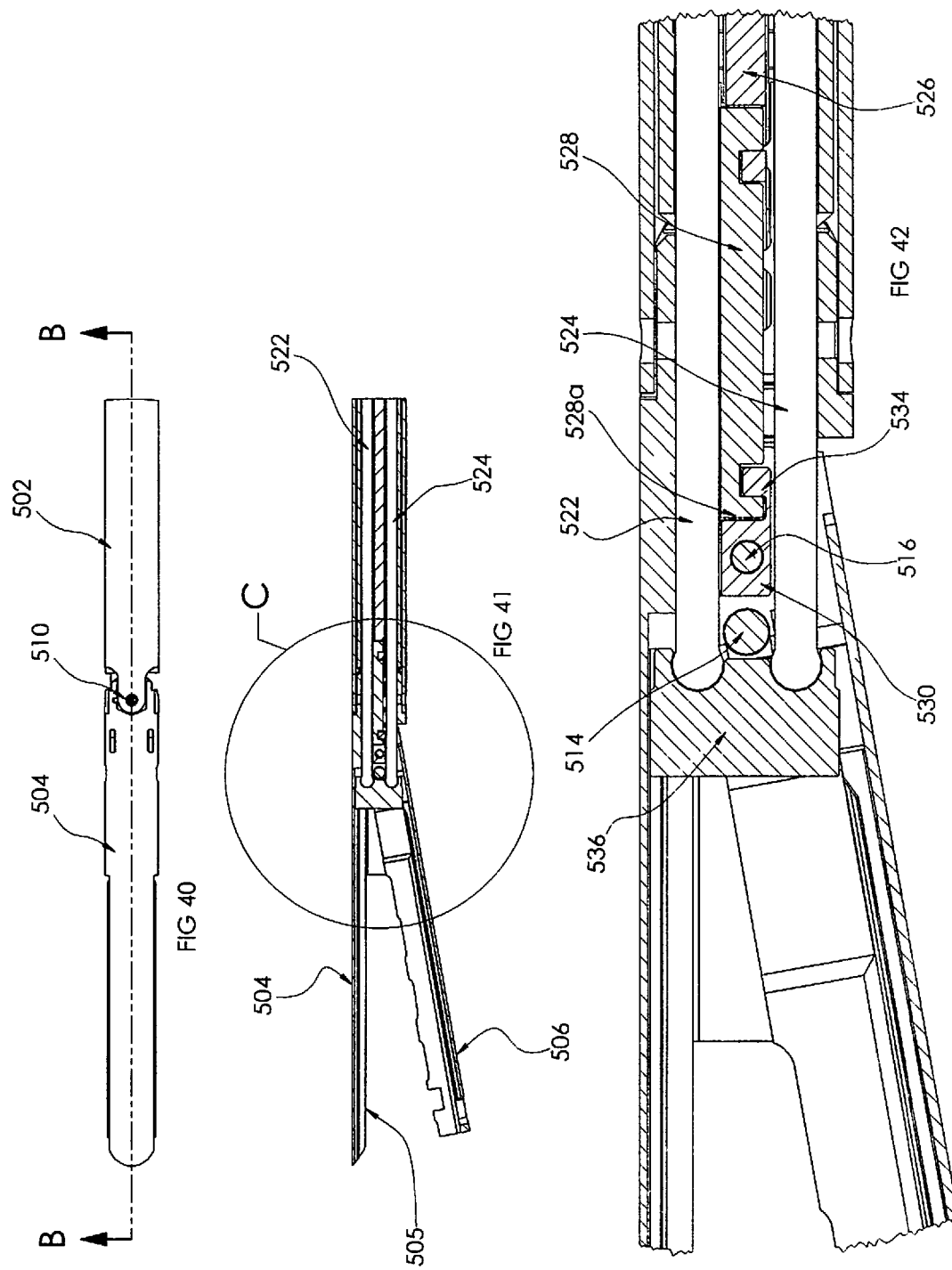

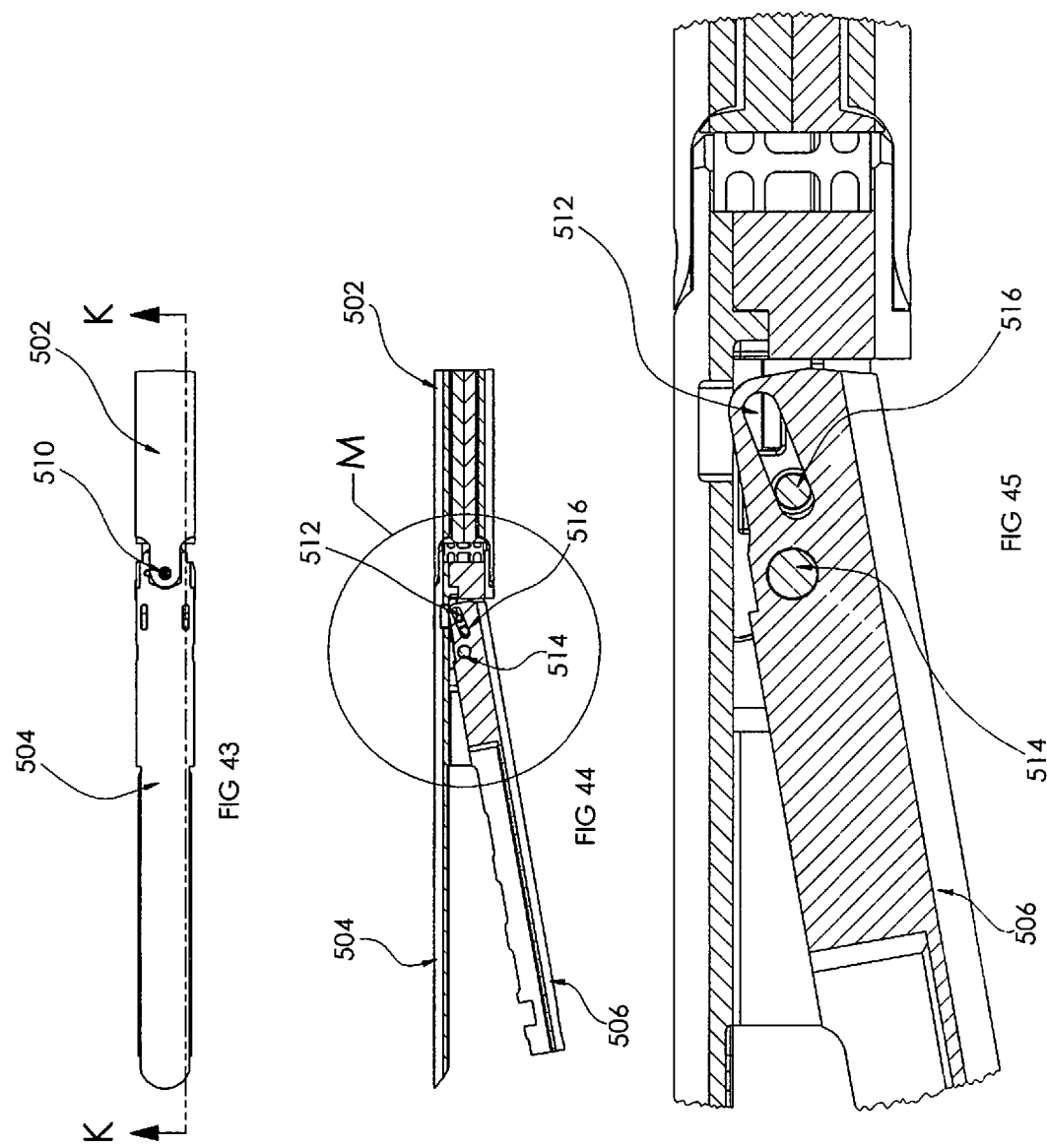

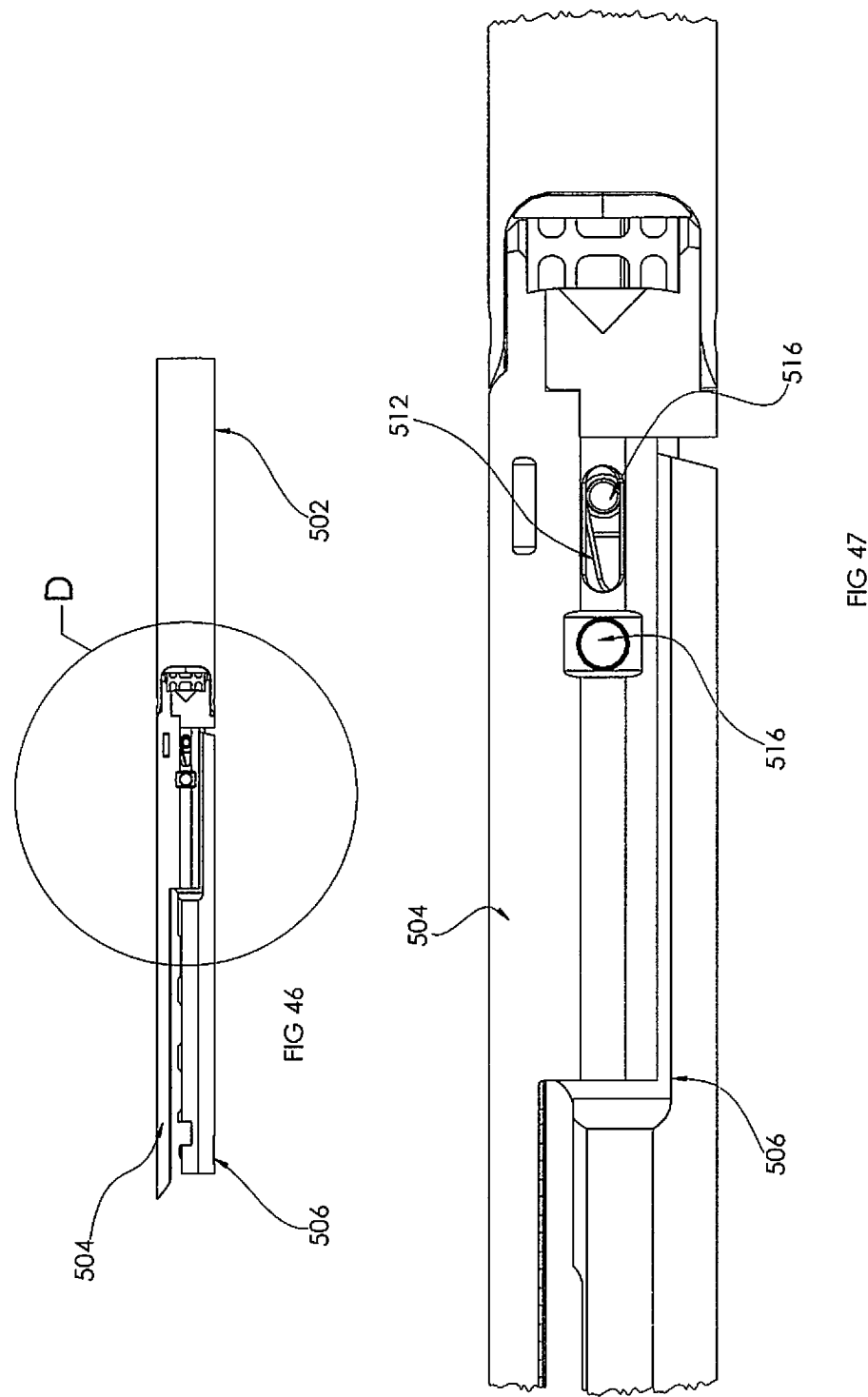

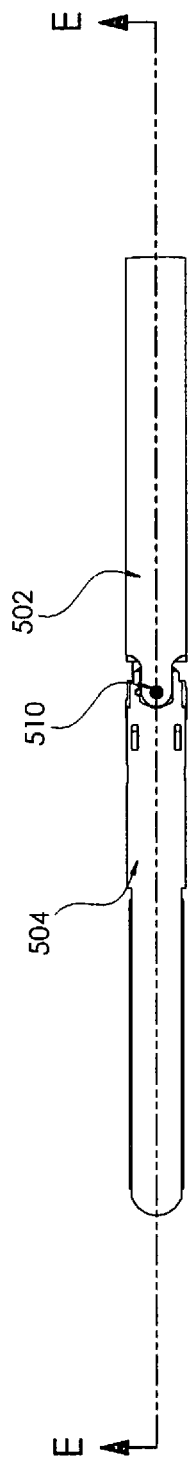
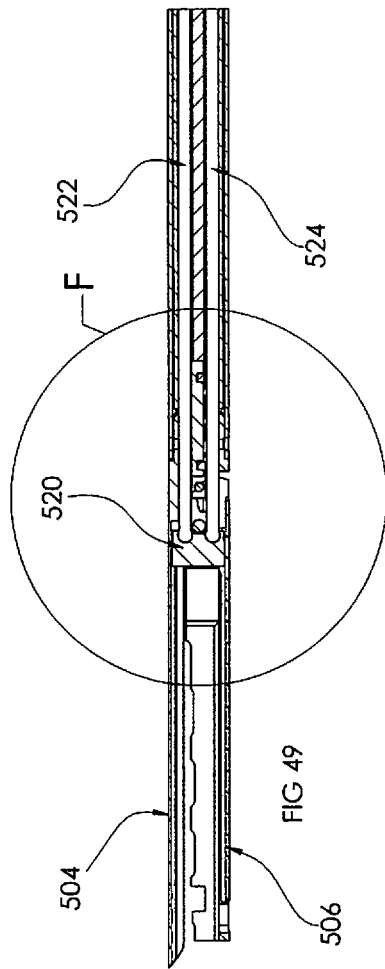
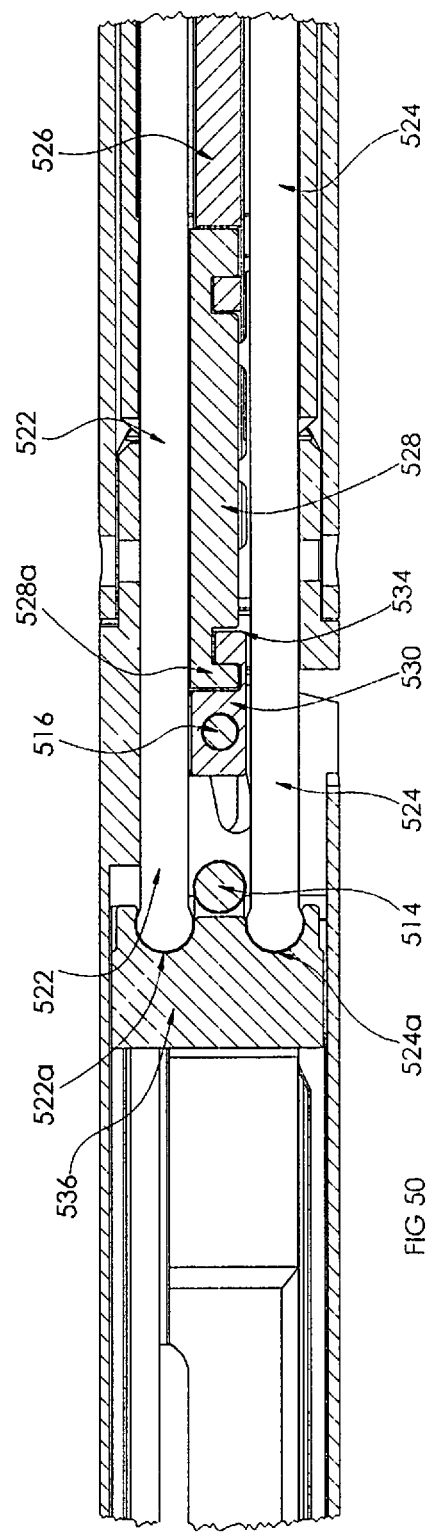
FIG 48
FIG 49
FIG 50

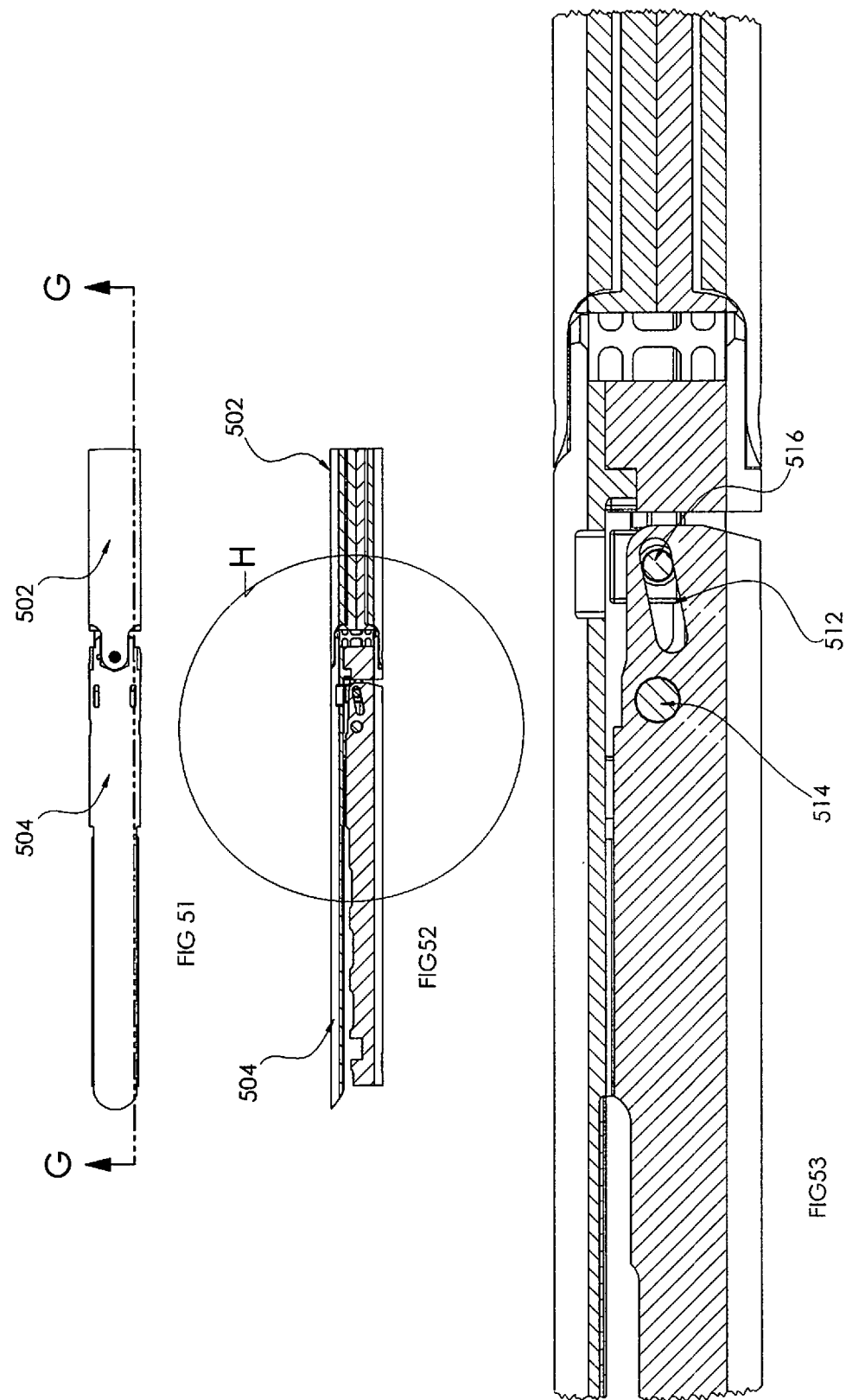

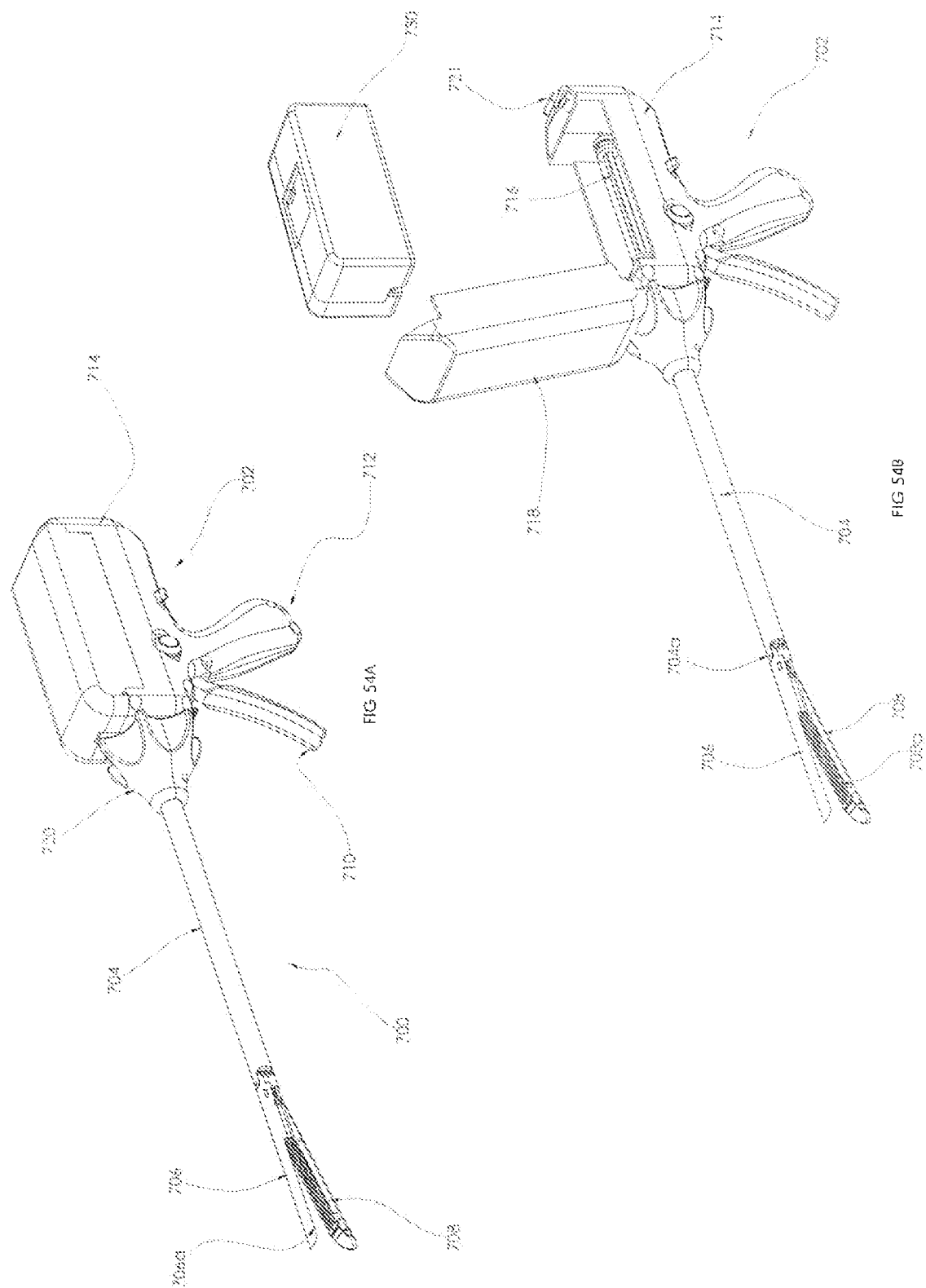

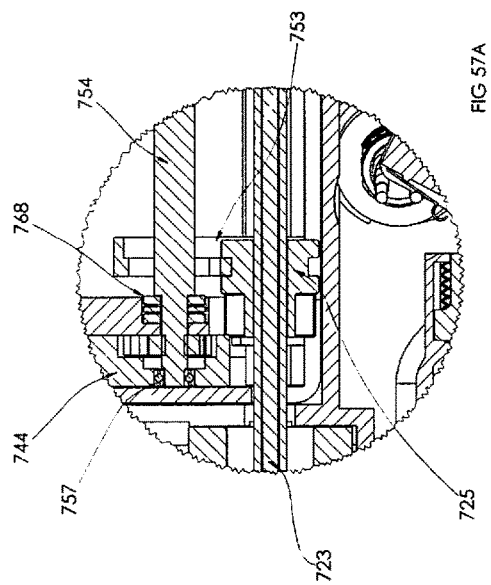
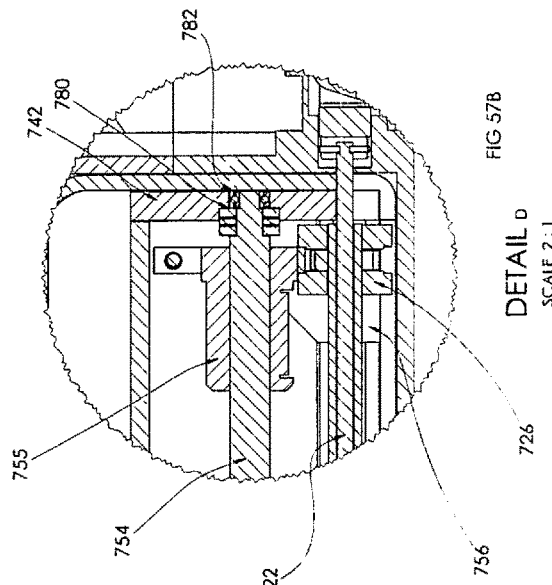
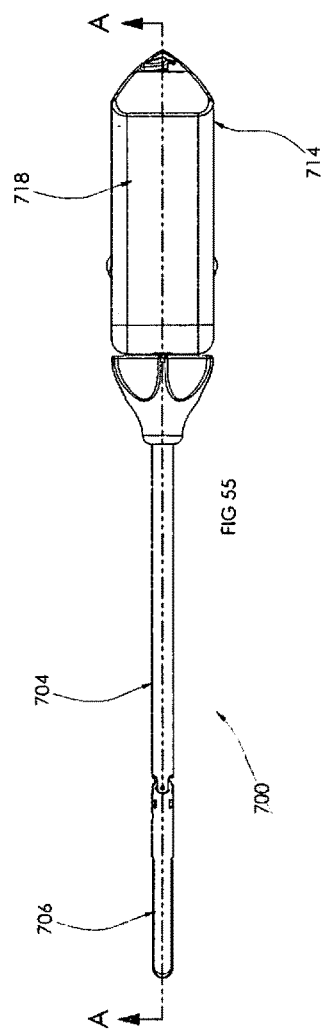
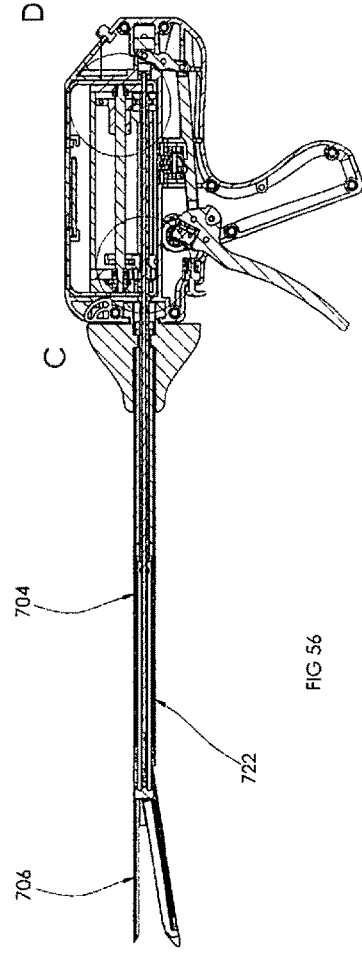

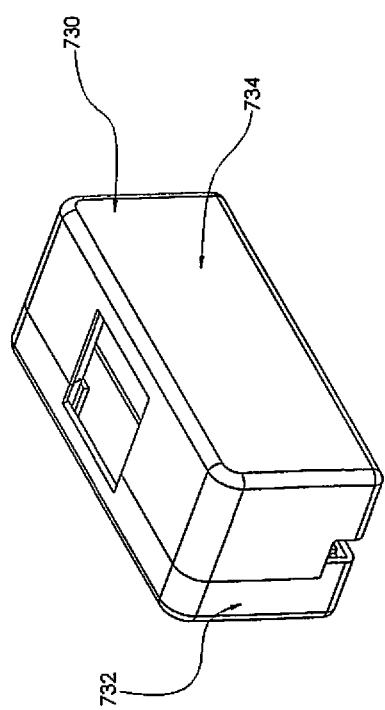

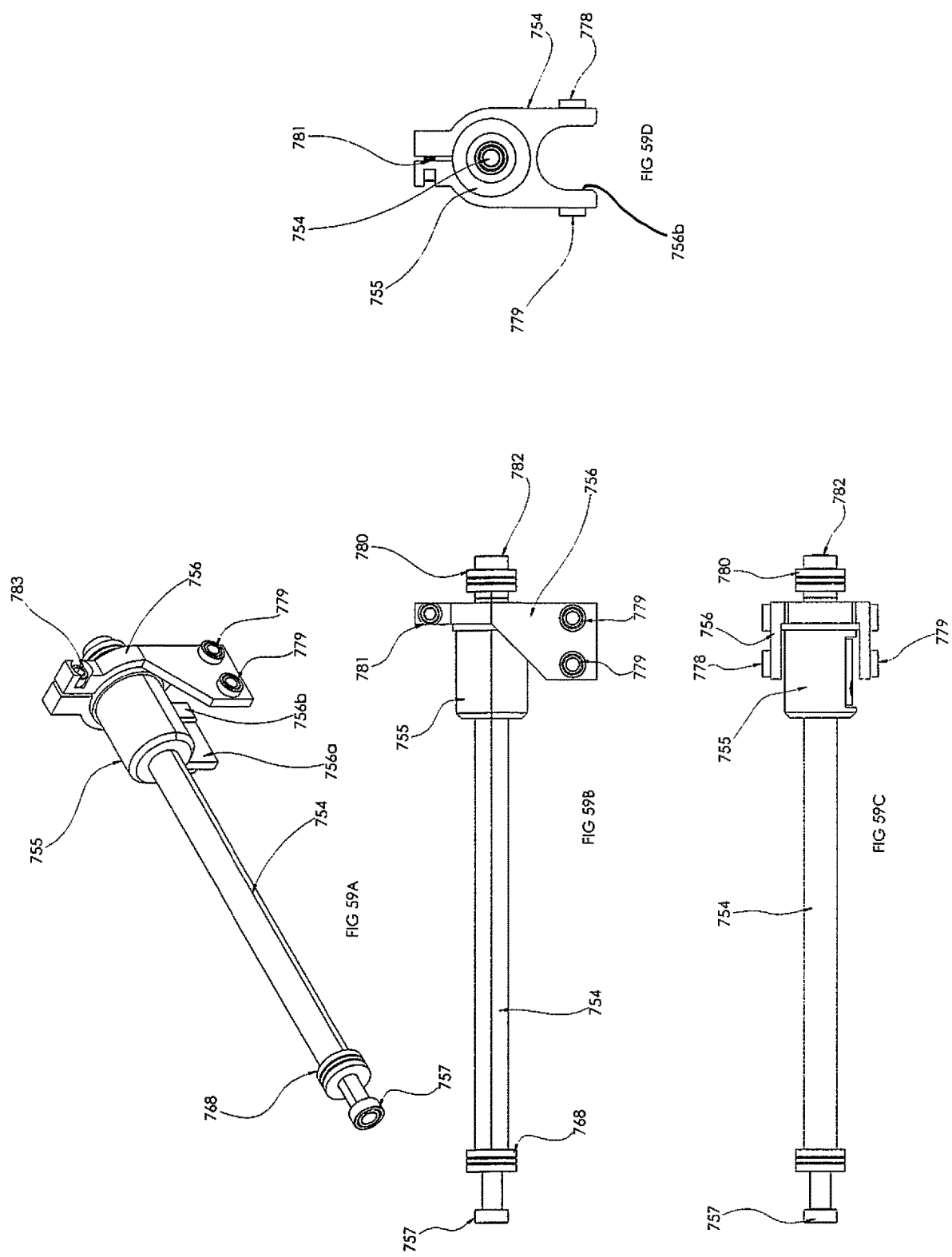

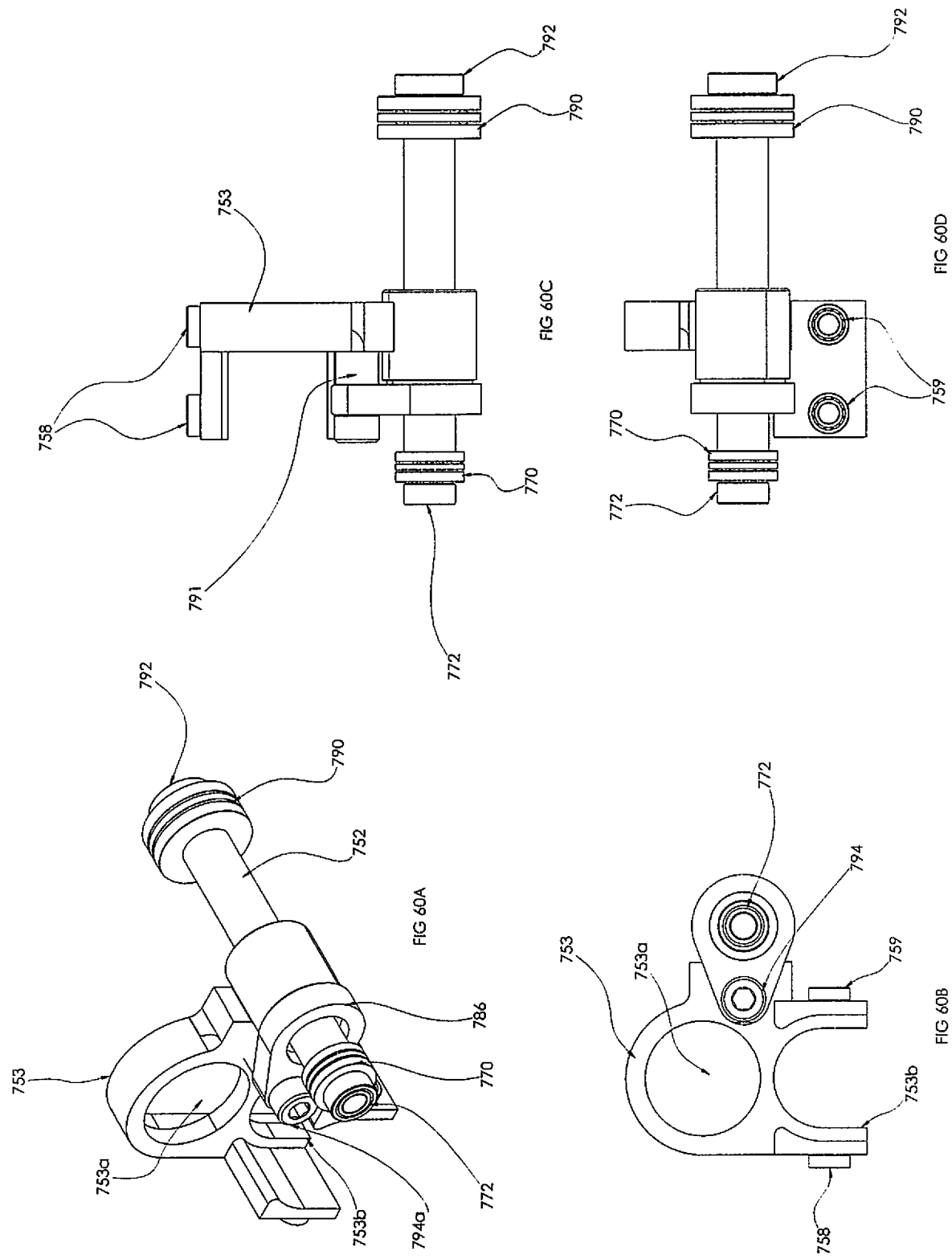

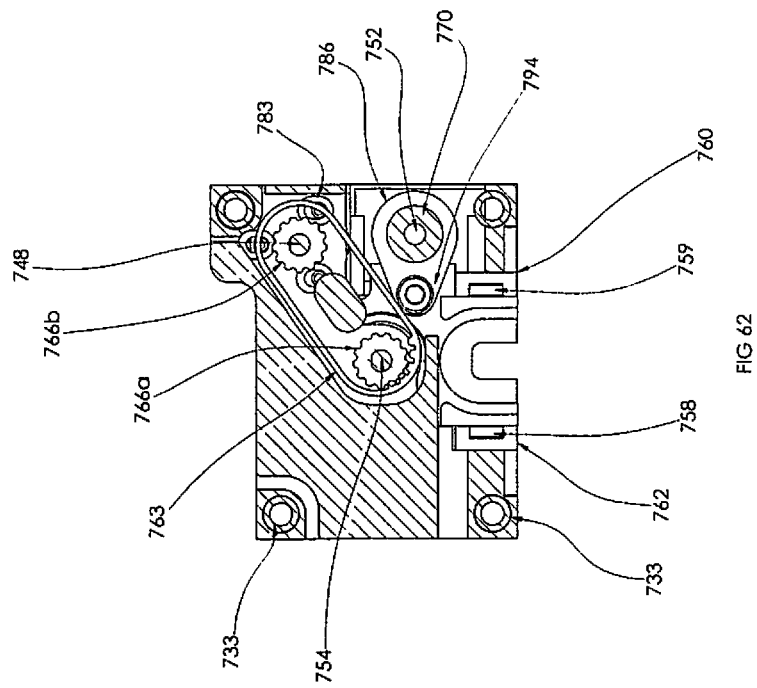
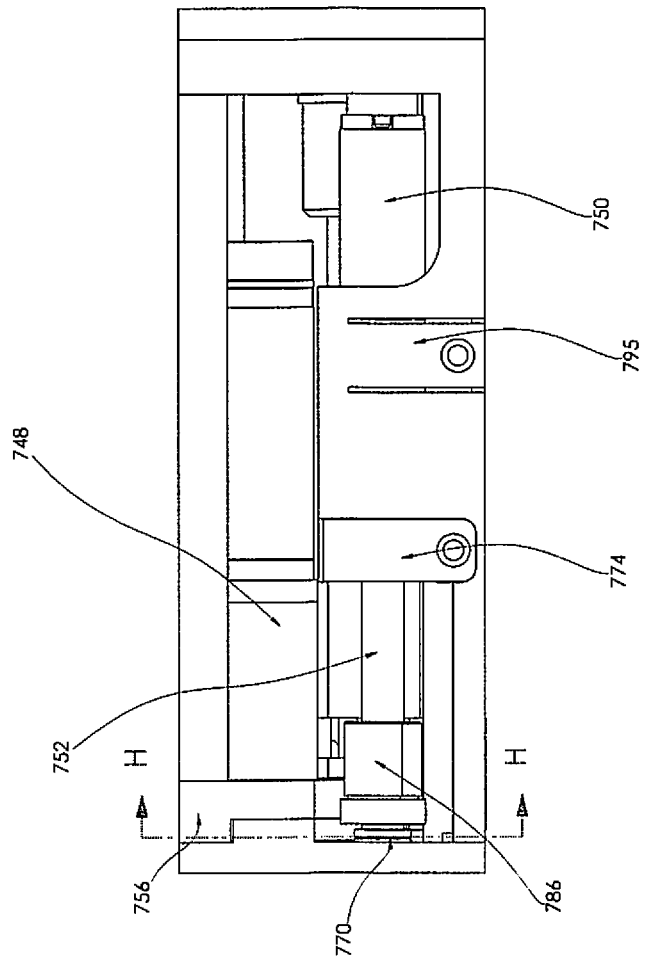

SECTION E-E

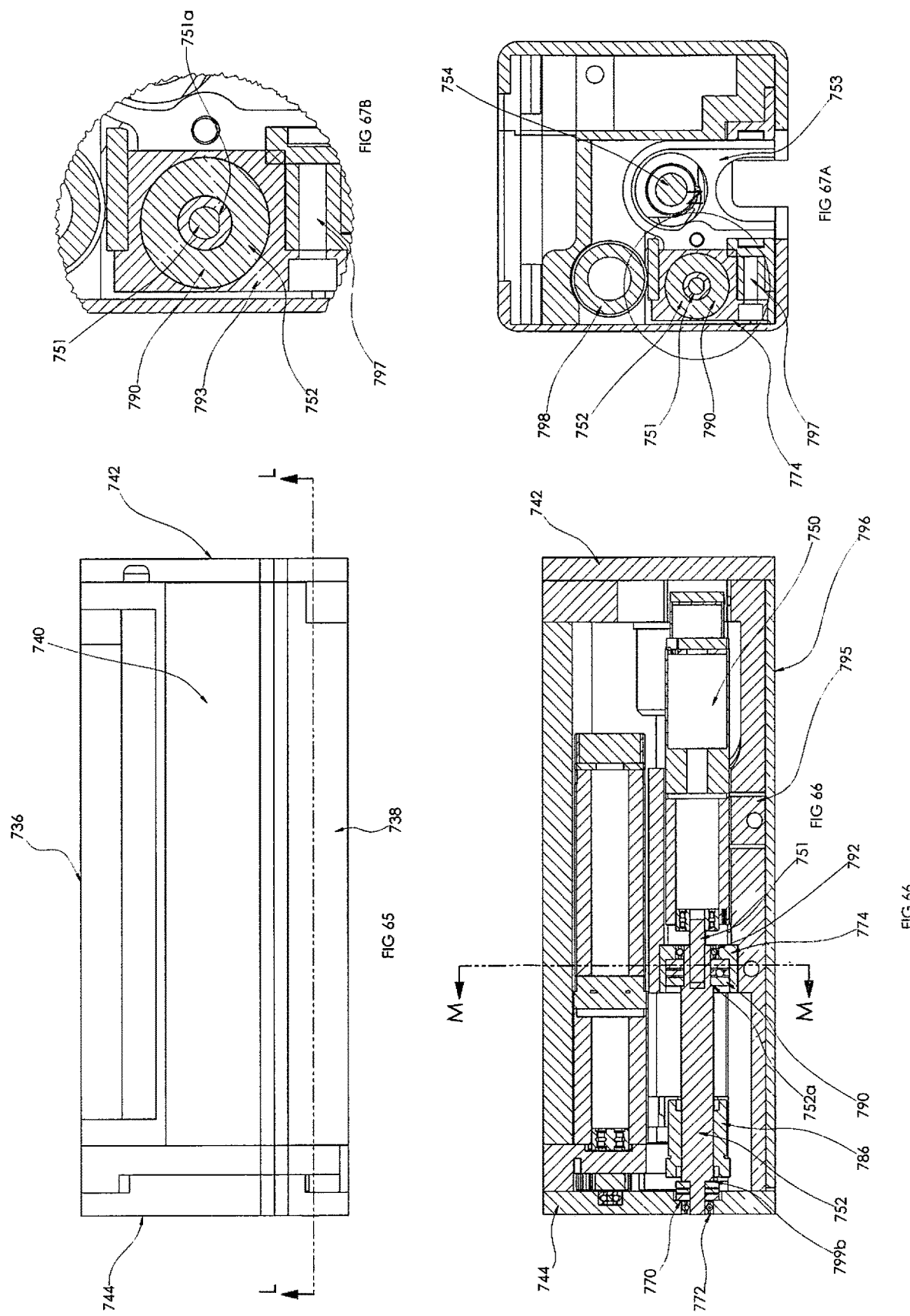

SURGICAL STAPLER WITH REMOVABLE POWER PACK AND INTERCHANGEABLE BATTERY PACK

This application is a continuation of application Ser. No. 16/792,110, filed Feb. 14, 2020, which claims priority from provisional application Ser. No. 62/812,934, filed Mar. 1, 2019 and from provisional application Ser. No. 62/900,146, filed Sep. 13, 2019, and is a continuation in part of application Ser. No. 15/965,737, filed Apr. 27, 2018, now U.S. Pat. No. 10,966,720, which claims priority from provisional application Ser. No. 62/553,297, filed Sep. 1, 2017 and from provisional application Ser. No. 62/616,045, filed Jan. 11, 2018. The entire contents of each of these applications are incorporated herein by reference.

BACKGROUND OF THE INVENTION

1. Field of the Invention

This application relates to surgical staplers, and more particularly, to surgical staplers having removable power packs to effect firing of the staples.

2. Background

Surgical staplers are used in various medical applications where a device is needed to join and dissect anatomical tissue. However, there are drawbacks and costs associated with use of surgical staplers. Currently staplers are either fully disposable, reusable or partially reusable. Due to contamination during the surgical procedure, e.g., exposure to the patient's body fluids, the staplers are required to be sterilized after use, a time consuming and expensive process, with possible risks of infection if not properly sterilized as contaminants adhered to the surgical stapler from a previous use could be transferred to another patient. To avoid the risks of resterilization, some surgical staplers are disposed after use in the surgical procedure. These staplers can be reloaded to fire multiple cartridges of staples, but after the procedure, the staplers are discarded. However, the practice of using single use disposable surgical staplers is costly.

In certain procedures, high forces are required to fire the staples through tissue into contact with the anvil for formation. This is compounded when multiple rows of staples are fired either simultaneously or sequentially from the stapler. Therefore, powered staplers have been introduced to reduce the force requirements of the user. Such powered staplers have motor driven mechanisms (assemblies) to advance components within the stapler to fire the staples from the cartridge through tissue. Such powered staplers, if reusable, are subject to the same aforementioned costs and risk of resterilization. However they suffer from additional drawbacks since the sterilization process and/or heat or chemicals used in the sterilization process can damage the electronic components of the drive assemblies, which may shorten the lifespan of the surgical stapler or adversely affect its function if resterilization compromises the function of the motor or drive assembly. If the stapler is disposable, the stapler becomes more costly since the electronic components, which add to the cost of the stapler, are also discarded with the stapler.

It would be advantageous to provide a cost effective, efficient, simple to use and advanced assemblies for powering surgical instruments which overcome the drawbacks of manual actuation without suffering from the disadvantages of current power driven staplers.

SUMMARY

The present invention overcomes the deficiencies and disadvantages of the prior art. The present invention advantageously provides surgical staplers that overcome the drawbacks discussed above by having a fully enclosed and removable power pack. The power packs according to the present disclosure may be used multiple times without the need to sterilize the power pack between uses because the power pack is fully enclosed and sealed by the surgical stapler handle assembly or housing, thereby preventing contact between the power pack and the patient and/or patient's bodily fluids or the like. Thus, the surgical staplers of the present disclosure advantageously reduce the time, resources and/or costs for preparing the surgical stapler for its next use. The present disclosure also provides power packs that are cost effective, efficient and easily loadable into surgical staplers where they engage structure in the housing to effect varied functions of the stapler.

In accordance with one aspect of the present disclosure, a surgical fastener applier is provided comprising a housing containing a compartment therein and an elongated member extending distally from the housing. A first jaw and a second jaw are positioned at a distal portion of the elongated member, wherein at least the first jaw is movable with respect to the second jaw to clamp tissue between the first and second jaws. A firing mechanism is positioned within the housing and is movable between a first position and a second firing position, wherein in the second position, the firing mechanism effects firing of fasteners into the tissue clamped between the first and second jaws. A cover on the housing is openable to access the compartment within the housing and a power pack is removably loadable into the compartment, the power pack having a motor and an engagement member removably engageable with the firing mechanism within the compartment when the power pack is loaded into the compartment to effect movement of the firing mechanism from the first position to the second firing position.

In some embodiments, a first seal to seal about the cover in the closed position is provided to protect the power pack positioned within the housing and/or the apparatus includes a second seal to block passage of body fluids from the elongated member into the compartment.

In some embodiments, the power pack has a housing and one of the housing or the compartment has at least one external rib and another of the housing or the compartment has at least one groove to receive the rib to guide the power pack within the compartment. Other guide structures could alternatively be provided.

In some embodiments, the power pack includes a second engagement member removably engageable with an articulating mechanism of the surgical fastener applier to effect articulation of the first and second jaws from a linear position to a position angled with respect to a longitudinal axis of the elongated member. The power pack can include a second motor and the second motor can effect linear movement of the articulation mechanism of the surgical fastener applier.

In some embodiments, the power pack includes a gear mechanism powered by the motor, wherein rotation of a motor shaft of the motor effects rotation of the gear mechanism which effects linear movement of the firing mechanism of the surgical fastener applier. In other embodiments, the power pack includes a drive belt powered by the motor, wherein rotation of a motor shaft of the motor effects rotation of a first disc which moves the drive belt to effect linear movement of the firing mechanism of the surgical fastener applier.

In accordance with another aspect of the present disclosure, a surgical fastener applier is provided comprising a housing containing a compartment therein, an elongated member extending distally from the housing and a jaw assembly including a first jaw and a second jaw at a distal portion of the elongated member wherein at least the first jaw is movable with respect to the second jaw. A jaw clamping mechanism is movable between a first position and second position to move at least the first jaw toward the second jaw to clamp tissue between the first and second jaws. A firing mechanism is movable between a first position and a second firing position to fire fasteners into the tissue clamped between the first and second jaws. An articulation mechanism is movable between a first position and a second position to articulate the jaw assembly from a linear position to a second position angled with respect to a longitudinal axis of the elongated member. A cover on the housing is movable from a closed position to an open position to access the compartment. A power pack is loadable into the compartment, the power pack having a motor and an engagement member engageable with the articulation mechanism to effect movement of the articulation mechanism from the first position to the second position.

In some embodiments, the power pack includes a gear mechanism for moving a drive mechanism linearly to move the articulation mechanism linearly to articulate the jaw assembly. In other embodiments, the power pack includes a drive belt for moving a drive mechanism linearly to move the articulation mechanism linearly to articulate the jaw assembly.

In accordance with another aspect of the present disclosure, a method for powering a surgical stapler is provided comprising the steps of:

providing a surgical stapler having a housing containing a compartment and a cover movable between a closed position and an open position;

loading a power pack having a drive mechanism into the compartment when the cover is in the open position, wherein the step of loading the power pack releasably engages the drive mechanism with a firing mechanism in the housing;

closing the cover to seal the compartment from an external environment;

actuating the motor to move the drive mechanism linearly to thereby move the firing mechanism linearly to advance a plurality of staples into body tissue; and after advancing the staples, opening the cover and removing the power pack from the compartment to release the engagement of the drive mechanism from the firing mechanism.

In some embodiments, the surgical stapler has first and second jaws movable from an open position to a closed by position by manual movement of a handle.

In some embodiments, the step of loading a power pack into the compartment releasably engages a second drive mechanism of the power pack with an articulation mechanism in the housing.

In accordance with another aspect of the present invention, a power pack is provided removably loadable into a housing of a surgical instrument, the power pack comprising a motor having a motor shaft, a rotatable disc operably connected to the motor shaft, a drive mechanism operably connected to the rotatable disc, and an engagement member linearly movable by the drive mechanism. The engagement member is configured to removably engage an axially movable member in the housing of the surgical instrument, wherein actuation of the motor causes linear movement of the engagement member to effect movement of the axially movable member in an axial direction.

In some embodiments, the rotatable disc is engageable with a drive belt to move the drive mechanism in an axial direction. In some embodiments, the rotatable disc is a gear for moving the drive mechanism axially.

In some embodiments, a second engagement member is provided which is configured to engage a second axially movable member in the housing of the surgical instrument. A second motor and second rotatable disk can be provided for moving the second engagement member axially.

In some embodiments, the first motor is configured to drive a plurality of staples through tissue and the second motor is configured to articulate jaws of the surgical instrument to an angled position with respect to the instrument. In some embodiments, the first motor or the second motor is configured to move the jaws of the surgical instrument between an open and closed position.

In accordance with another aspect of the present disclosure, a surgical instrument is provided comprising a housing containing a compartment therein, an elongated member extending distally from the housing, and a first jaw and a second jaw at a distal portion of the elongated member, at least the first jaw movable with respect to the second jaw. An advancing mechanism is positioned within the housing and is movable between a first position and a second position. A cover on the housing is openable to access the compartment within the housing. A power pack is loadable into the compartment, the power pack having a motor and an engagement member engageable with the advancing mechanism within the compartment when the power pack is loaded into the compartment to effect movement of the advancing mechanism from the first position to the second position.

In some embodiments, the advancing mechanism is operably connected to at least one of the first and second jaws, wherein movement of the jaw advancing mechanism effects closing of the first and second jaws. In other embodiments, movement of the advancing mechanism effects firing of at least one fastener into the tissue clamped between the first and second jaws.

In some embodiments, the power pack has a second motor and a second engagement member engageable with a second advancing mechanism positioned within the housing of the instrument when the power pack is loaded into the compartment to effect movement of the second advancing mechanism from the first position to the second position.

In accordance with another aspect of the present disclosure, a surgical instrument is provided comprising a housing containing a compartment therein configured to receive a power pack, an elongated member extending distally from the housing and a first jaw and a second jaw at a distal portion of the elongated member, at least the first jaw movable with respect to the second jaw to clamp tissue between the first and second jaws. A firing mechanism is positioned within the housing, the firing mechanism movable between a first position and a second firing position, wherein in the second position, the firing mechanism effects firing of at least one fastener into the tissue clamped between the first and second jaws. A cover is mounted on the housing movable from a closed position to an open position to access the compartment within the housing, the cover in the closed position sealing the compartment from the external environment to protect a power pack when loaded therein. A first seal is provided to prevent flow of body fluids into the compartment from the elongated member to protect the power pack when loaded in the compartment.

In some embodiments, the housing contains a firing rod positioned therein to removably receive an engagement member of the power pack when loaded therein for motorized advancement of the firing rod to effect firing of at least one fastener supported in the instrument.

In accordance with another aspect of the present invention, a surgical fastener applier is provided comprising a housing containing a compartment therein, an elongated member extending distally from the housing and a first jaw and a second jaw at a distal portion of the elongated member, at least the first jaw movable with respect to the second jaw to clamp tissue between the first and second jaws. A firing mechanism is positioned within the housing movable between a first position and a second position, wherein movement to the second position effects firing of fasteners into the tissue clamped between the first and second jaws. A power pack is removably loadable into the compartment, the power pack having a motor and an engagement member removably engageable with the firing mechanism when the power pack is loaded into the compartment to effect movement of the firing mechanism from the first position to the second position. An interchangeable battery pack is removably connectable with the power pack for powering the motor.

In some embodiments, the surgical fastener applier includes a cover on the housing openable to access the compartment, wherein the cover includes a first seal to seal about the cover in a closed position of the cover to protect the power pack positioned within the compartment. The applier can include a second seal to block passage of body fluids from the elongated member into the compartment.

In some embodiments, the battery pack is slidable into a cavity in the power pack; in other embodiments, the battery pack is mountable to an outer surface, e.g., upper surface, of the power pack.

The battery pack can have an engagement tab for gripping by a user to facilitate removal from the power pack.

In some embodiments, the power pack includes a second engagement member, the second engagement member removably engageable with an articulating mechanism in the housing of the surgical fastener applier to effect articulation of the first and second jaws from a linear position to a position angled with respect to a longitudinal axis of the elongated member. In some embodiments, the power pack includes a second motor and the second motor effects linear movement of the articulating mechanism.

In accordance with another aspect, the present invention provides a power pack removably loadable into a compartment of a housing of a surgical instrument, the power pack having a motor, a motor shaft, a drive mechanism operably connected to the motor shaft and including an engagement member linearly movable. The power pack has a replaceable battery pack removably connectable to a contact within the power pack for powering the motor. The engagement member is configured to removably engage an axially movable member in the housing of the surgical instrument, wherein actuation of the motor causes linear movement of the engagement member to effect movement of the axially movable member in an axial direction.

In some embodiments, the power pack includes a second engagement member configured to engage a second axially movable member in the housing of the surgical instrument and a second motor for moving the second engagement member axially.

In some embodiments, the battery pack is replaceable while the power pack remains in the compartment of the surgical instrument.

In accordance with another aspect of the present invention, a method for powering a disposable surgical stapler is provided comprising:
 a) providing a disposable surgical stapler having first and second jaws, an elongated shaft and a housing containing a compartment;
 b) loading a reusable power pack into the compartment of the housing, the reusable power pack having a motor;
 c) actuating the motor to advance a plurality of staples from the first jaw into body tissue;
 d) in an event of battery failure, removing a battery pack from the power pack for replacement with a second charged battery pack; and
 e) after advancing the plurality of staples, removing the power pack from the compartment for subsequent reuse of the power pack in another surgical stapler in another procedure without requiring sterilization.

In some embodiments, the power pack has a drive mechanism and the step of loading the power pack into the compartment releasably engages the drive mechanism with a firing mechanism in the housing of the surgical stapler for firing the plurality of staples, and removal of the power packs releases the engagement of the drive mechanism from the firing mechanism.

In some embodiments, the power pack includes a second motor, and the step of loading the power pack into the compartment releasably engages a second drive mechanism of the power pack with an articulation mechanism in the housing of the surgical stapler, the articulation mechanism movable to move the first and second jaws to an angle to a longitudinal axis of the elongated shaft.

In some embodiments, the battery pack is loaded into or onto the power pack prior to the step of loading the power pack into the compartment.

In some embodiments, in the event of battery failure during a surgical procedure, the battery pack is removed from the power pack while the power pack remains in the compartment and replaced with the second battery pack while the battery pack remains in the compartment. In other embodiments, in the event of battery failure during a surgical procedure, the power pack is removed from the compartment and replaced with a second battery pack outside the compartment.

In accordance with another aspect of the present invention. a surgical fastener applier is provided including a housing containing a compartment therein, an elongated member extending distally from the housing, and a first jaw and a second jaw adjacent a distal portion of the elongated member, at least the first jaw movable with respect to the second jaw to clamp tissue between the first and second jaws. A fastener firing mechanism is positioned within the housing and is movable between a first position and a second position, wherein in the second position, the firing mechanism effects firing of fasteners into the tissue clamped between the first and second jaws. A power pack is removably loadable into the compartment, the power pack has a first motor and a first engagement member removably engageable with the firing mechanism within the housing when the power pack is loaded into the compartment. The first engagement member is movable axially in response to rotation of a first screw operatively connected to the motor, and at least one bearing limits one or both of radial movement and axial movement of the first screw, wherein movement of the first engagement member effects movement of the firing mechanism from the first position to the second position.

In some embodiments, the power pack includes a second motor and a second engagement member removably engageable with an articulation mechanism within the housing when the power pack is loaded into the compartment. The second engagement member can be movable axially in response to rotation of a second screw operatively connected to the motor, and at least one bearing limits one or both of radial movement and axial movement of the second screw, wherein movement of the second engagement member effects movement of the articulation mechanism to effect articulation of the first and second jaws with respect to a longitudinal axis of the elongated member.

In some embodiments, one or both of the first engagement member and second engagement member has a pair of bearings movable within a track during axial movement. In some embodiments, the first and second engagement members are axially aligned. In some embodiments, the second motor and second screw are in axial alignment and the first motor and first engagement member are radially offset.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein:

FIG. 3A is a perspective view of the surgical stapler of FIG. 1 showing the handle compartment cover in the open position and further showing the power pack prior to insertion into the handle compartment;

FIG. 3B is front view of the surgical stapler of FIG. 3A showing the handle compartment cover in the open position;

FIG. 3C is a front view of the power pack of FIG. 3A;

FIG. 4A is a top view of the motor and drive mechanism (assembly) of the power pack of FIG. 3A;

FIG. 4B is a side view of the motor and drive mechanism of the power pack of FIG. 4A;

FIG. 4C is a top view of the power pack of FIG. 3A;

FIG. 4D is a side view of the motor and drive (mechanism) of FIG. 4A shown engaged with the rod of the firing assembly mechanism of the surgical stapler of FIG. 1;

FIG. 4E is a perspective view of the motor and drive mechanism of the power pack of FIG. 3A;

FIG. 4F is a cross-sectional view taken along line AY-AY of FIG. 4C showing the power pack engaging the firing rod of the surgical stapler of FIG. 1;

FIG. 4G is a side view of the power pack of FIG. 3A;

FIG. 4H is a cross-sectional view taken along line AT-AT of FIG. 4G;

FIG. 4I is a top view of the surgical stapler of FIG. 1;

FIG. 7A is a top view of the surgical stapler of FIG. 1 with the power pack fully inserted into the compartment in the handle and the cover in the closed position;

FIG. 7B is a cross-sectional view taken along line A-A of FIG. 7A;

FIG. 7C is a close up view of the area of detail B of FIG. 7B showing the firing mechanism at the distal end for firing staples;

FIG. 8A is a top view of the surgical stapler of FIG. 1 showing the power pack fully inserted and the cover of the handle compartment in the closed position, the view the same as FIG. 7A but having section line E-E;

FIG. 8B is a cross-sectional view taken along line E-E of FIG. 8A, the view being the same as FIG. 7B but having section lines F-F and identified area of detail B;

FIG. 8C is a side view of the surgical stapler of FIG. 1 showing the power pack fully inserted in the handle compartment and the compartment cover closed;

FIG. 8D is a cross-sectional view taken along line J-J of FIG. 8C;

FIG. 9 is a cross-sectional view taken along line F-F of FIG. 8B;

FIG. 10 is a close up view of the area of detail G of FIG. 8B;

FIG. 11 is a close up view of the area of detail H of FIG. 9;

FIG. 12 is a close up view of the detail K of FIG. 8D;

FIG. 13A is a side view of an alternate embodiment of the surgical stapler showing the power pack of FIG. 3A prior to insertion into the handle compartment;

FIG. 13B is a side view similar to FIG. 13A showing the power pack of FIG. 3A inserted into the handle compartment;

FIG. 13C is a side view of another alternate embodiment of the surgical stapler showing the power pack of FIG. 3A prior to insertion into the handle compartment;

FIG. 13D is a side view similar to FIG. 13C showing the power pack of FIG. 3A inserted into the handle compartment;

FIG. 14A is a side view illustrating an alternate embodiment having a power pack for effecting both firing and articulation of the surgical stapler, the power pack shown fully inserted into the compartment of the handle of the surgical stapler and the compartment cover shown in the closed position;

FIG. 14B is a top view of the surgical stapler of FIG. 14A;

FIG. 14C is a cross-sectional view taken along line C-C FIG. 14B;

FIG. 14D is a side view of the surgical stapler of FIG. 14A, the view being the same as FIG. 14A but having section line M-M;

FIG. 14E is cross-sectional view taken along line M-M of FIG. 14D;

FIG. 14F is a cross-sectional view taken along line N-N of FIG. 14D;

FIG. 15A is a close up view of the area of detail D of FIG. 14C;

FIG. 15B is a close up view of the area of detail O of FIG. 14E;

FIG. 15C is a top view of the power pack of FIG. 14A for effecting both firing and articulation of the surgical stapler;

FIG. 15D is a cross-sectional view taken along line AW-AW of FIG. 15C;

FIG. 15E is a side view of the power pack of FIG. 14A;

FIG. 15F is a cross-sectional view taken along line AT-AT of FIG. 15E;

FIG. 20 is a cross-sectional side view of the surgical stapler of FIG. 14A, the view being the same as FIG. 14C but having identified areas of detail Q, R and S;

FIG. 21A is an enlarged view of the area of detail Q of FIG. 20;

FIG. 21B is an enlarged view of the area of detail R of FIG. 19A;

FIG. 21C is an enlarged view of the area of detail S of FIG. 19A;

FIG. 22A is a top view of the motor and drive mechanism (assembly) of the power pack of FIG. 14A for effecting staple firing and articulation;

FIG. 22B is a side view of the motor and drive mechanism of the power pack of FIG. 14A;

FIG. 22C is a side view of the motor and drive mechanism of FIG. 14A shown engaged with the articulation rod of the articulation assembly of the surgical stapler of FIG. 14A;

FIG. 22D is a perspective view of the motor and drive mechanism (assembly) of the power pack of FIG. 14A;

FIG. 24A is a top view of the motor and drive mechanism (assembly) of the power pack of an alternate embodiment having a belt drive;

FIG. 24B is a side view of the motor and drive mechanism of FIG. 24A;

FIG. 24C is a perspective view of the motor and drive mechanism of FIG. 24A;

FIG. 24D is a front view of the motor and drive mechanism of FIG. 24A;

FIG. 25A is a top view of the motor and drive mechanism (assembly) of the power pack of an another alternate embodiment having a belt drive;

FIG. 25B is a side view of the motor and drive mechanism of FIG. 25A;

FIG. 25C is a perspective view of the motor and drive mechanism of FIG. 25A;

FIG. 25D is a front view of the motor and drive mechanism of FIG. 25A;

FIG. 27A is a top view of the motor and drive mechanism (assembly) of the power pack of an alternate embodiment having a belt drive;

FIG. 27B is a side view of the motor and drive mechanism of FIG. 27A;

FIG. 27C is a perspective view of the motor and drive mechanism of FIG. 27A;

FIG. 27D is a front view of the motor and drive mechanism of FIG. 27A;

FIG. 27E is a view similar to FIG. 27B showing engagement with the stapler firing rod;

FIG. 28A is a top view of an alternate embodiment of the surgical instrument containing the power pack of FIG. 3A within the handle compartment, the surgical instrument being a circular stapler;

FIG. 28B is a side view of the circular stapler of FIG. 28A;

FIG. 28C is a perspective view of the circular stapler of FIG. 28A;

FIG. 28D is a front view of the circular stapler of FIG. 28A;

FIG. 30A is a top view of an alternate embodiment of the surgical instrument containing the power pack of FIG. 3A within the handle compartment, the surgical instrument being a flexible endoscopic linear stapler;

FIG. 30B is a side view of the linear stapler of FIG. 30A;

FIG. 30C is a perspective view of the linear stapler of FIG. 30A;

FIG. 30D is a front view of the linear stapler of FIG. 30A;

FIG. 31A is a top view of an alternate embodiment of the surgical instrument containing the power pack of FIG. 3A within the handle compartment, the surgical instrument being an endoscopic clip applier;

FIG. 31B is a side view of the clip applier of FIG. 31A;

FIG. 31C is a perspective view of the clip applier of FIG. 31A;

FIG. 31D is a front view of the clip applier of FIG. 31A;

FIG. 32A is a top view of an alternate embodiment of the surgical instrument containing the power pack of FIG. 3A within the handle compartment, the surgical instrument being an endoscopic grasper;

FIG. 32B is a side view of the endoscopic grasper of FIG. 32A;

FIG. 32C is a perspective view of the endoscopic grasper of FIG. 32A;

FIG. 32D is a front view of the endoscopic grasper of FIG. 32A;

FIG. 33A is a top view of an alternate embodiment of the surgical instrument containing the power pack of FIG. 3A within the handle compartment, the surgical instrument being an endoscopic scissor;

FIG. 33B is a side view of the endoscopic scissor of FIG. 33A;

FIG. 33C is a perspective view of the endoscopic scissor of FIG. 33A; and

FIG. 33D is a front view of the endoscopic scissor of FIG. 33A.

FIG. 34A is a top view of an alternate embodiment of the surgical instrument containing the power pack of FIG. 3A within the handle compartment, the surgical instrument being a fastener applier;

FIG. 34B is a side view of the fastener applier of FIG. 34A;

FIG. 34C is a perspective view of the fastener applier of FIG. 34A;

FIG. 34D is a front view of the fastener applier of FIG. 34A;

FIG. 37B is a side view of the surgical instrument and battery pack of FIG. 37A;

FIG. 37C is a perspective view of the surgical instrument of FIG. 37A showing the power pack and battery pack within the compartment of the surgical instrument;

FIGS. 38A and 38B are side and perspective views, respectively, of an embodiment of a jaw clamping mechanism of the present invention, the cartridge jaw shown in the open position;

FIG. 39 is a close up view of the clamping mechanism of FIG. 38A;

FIG. 40 is top view of the jaws of FIG. 38A;

FIG. 41 is a cross-sectional view taken along line B-B of FIG. 40;

FIG. 42 is a close up view of the area of detail C of FIG. 41;

FIG. 43 is top view of the jaws of FIG. 38A;

FIG. 44 is a cross-sectional view taken along line K-K of FIG. 43;

FIG. 45 is a close up view of the area of detail M of FIG. 44;

FIG. 46 is a side view of the jaw clamping mechanism of FIG. 38A, the cartridge jaw shown in the closed position;

FIG. 47 is a close up view of the area of detail D of FIG. 46;

Figure 58B:
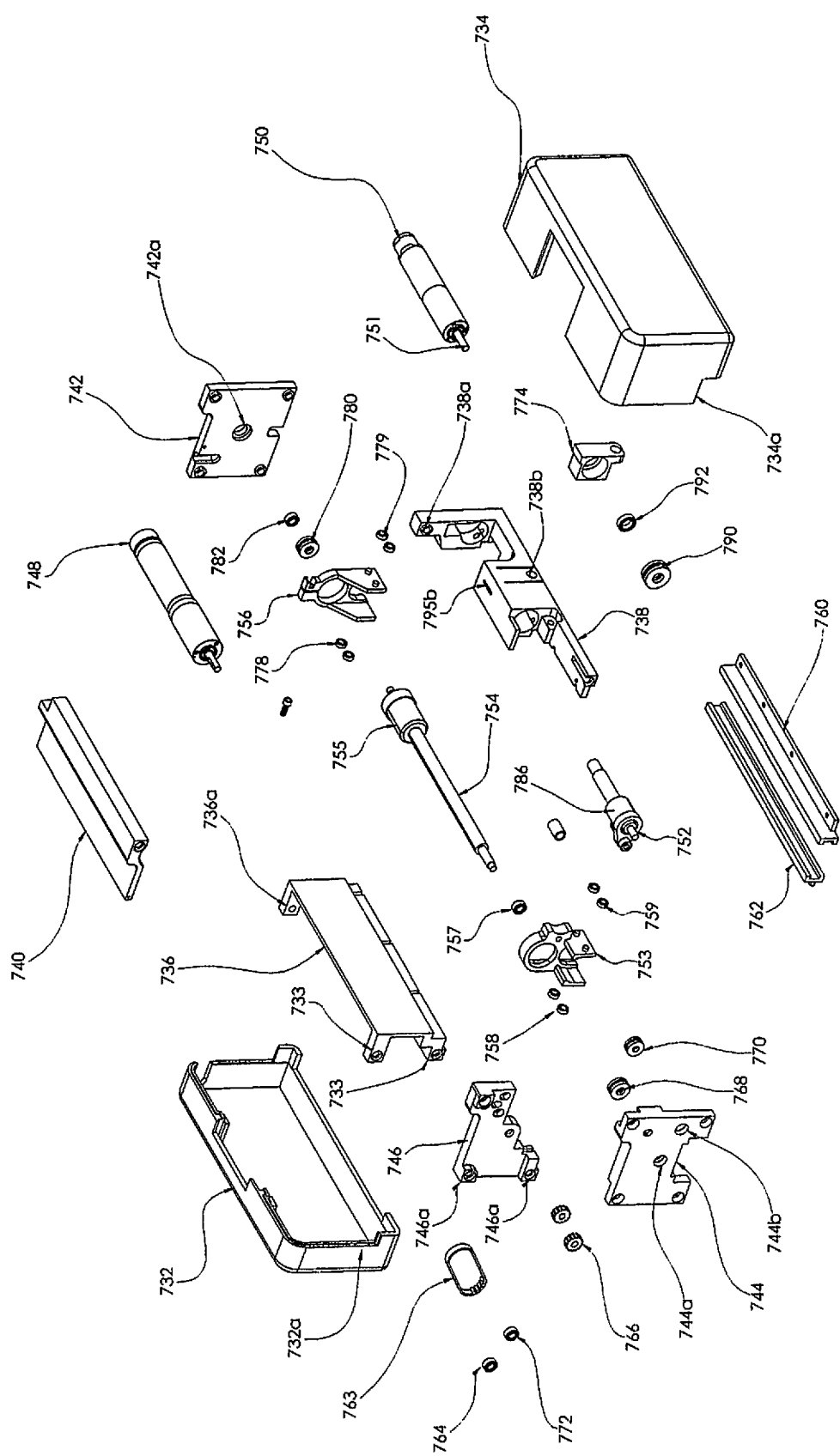

FIG. 48 is top view of the jaws of FIG. 38A in the closed position;

FIG. 49 is a cross-sectional view taken along line E-E of FIG. 48;

FIG. 50 is a close up view of the area of detail F of FIG. 49;

FIG. 51 is top view of the jaws of FIG. 38A in the closed position;

FIG. 52 is a cross-sectional view taken along line G-G of FIG. 48;

FIG. 53 is a close up view of the area of detail H of FIG. 52;

FIG. 54A is a perspective view of an alternate embodiment of the surgical stapler and power pack of the present invention;

FIG. 54B is a view similar to FIG. 54A showing the power pack of FIG. 58A being loaded into the surgical stapler;

FIG. 55 is a top view of the surgical stapler of FIG. 54;

FIG. 56 is a cross-sectional view taken along line A-A of FIG. 55;

FIG. 57A is a close up view of the area of detail C of FIG. 56;

FIG. 57B is a close up view of the area of detail D of FIG. 56;

FIG. 58A is a perspective view and FIG. 58B is an exploded view of an alternate embodiment of the power pack of the present invention;

FIGS. 59A, 59B, 59C and 59D illustrate the deployment screw assembly of the power pack of FIG. 58A for the staple firing mechanism wherein:

FIG. 59A is a perspective view of the deployment screw assembly;

FIG. 59B is a side view of the deployment screw assembly;

FIG. 59C is a top view of the deployment screw assembly; and

FIG. 59D is a rear view of the deployment screw assembly;

FIGS. 60A, 60B, 60C and 60D illustrate the articulation screw assembly of the power pack of FIG. 58A for the articulation mechanism wherein:

FIG. 60A is a perspective view of the articulation screw assembly;

FIG. 60B is a front view of the articulation screw assembly;

FIG. 60C is top view of the articulation screw assembly; and

Figure 63:
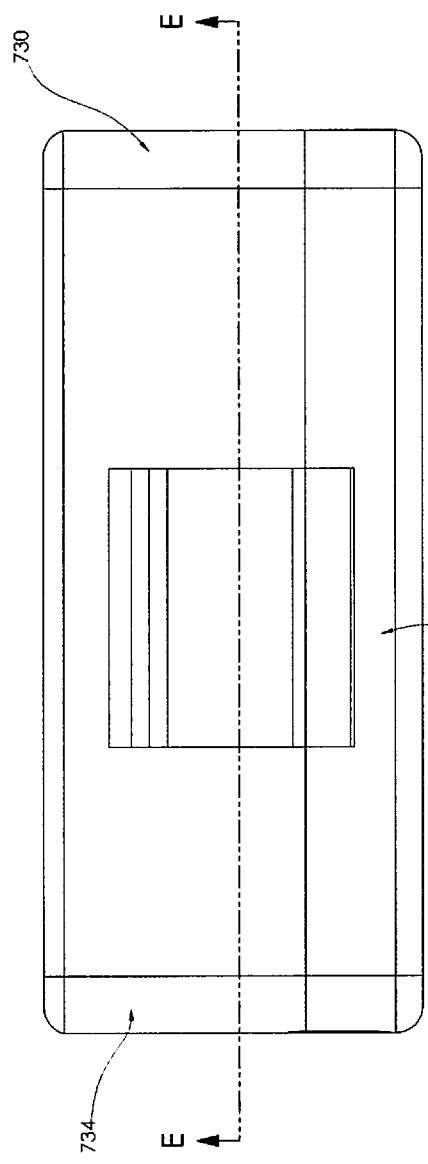
Figure 64:
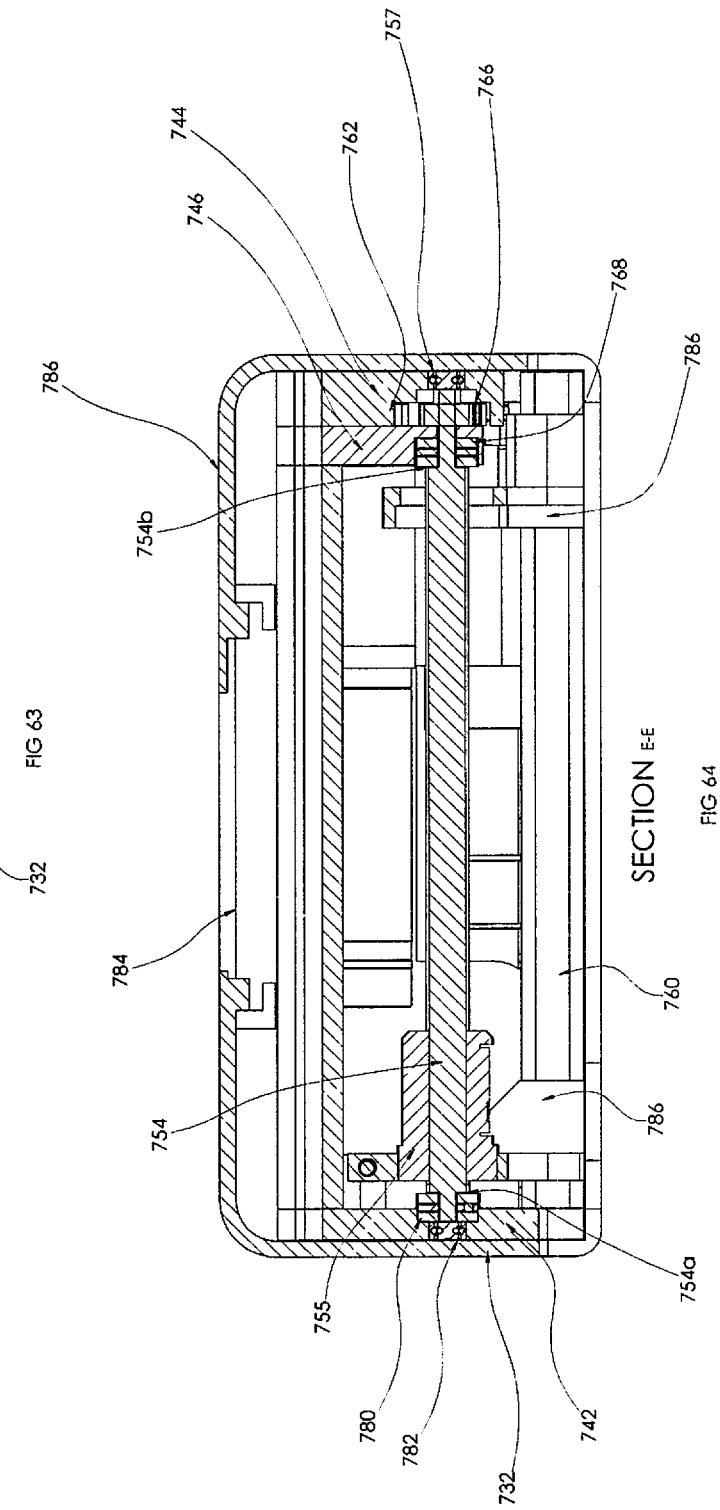
Figure 69:
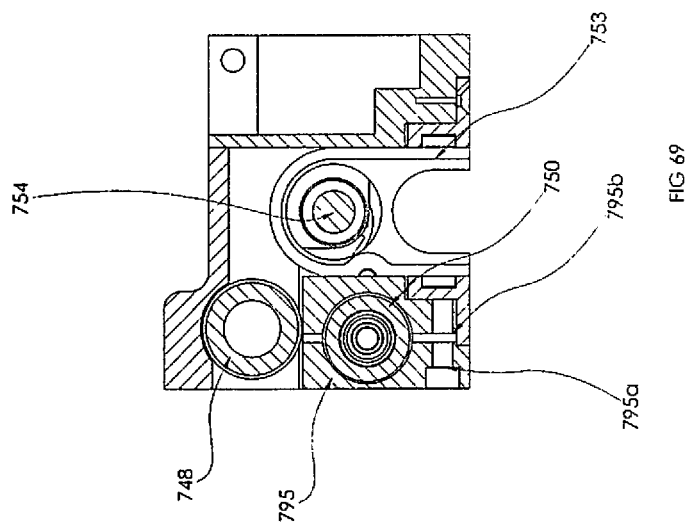
Figure 68A:
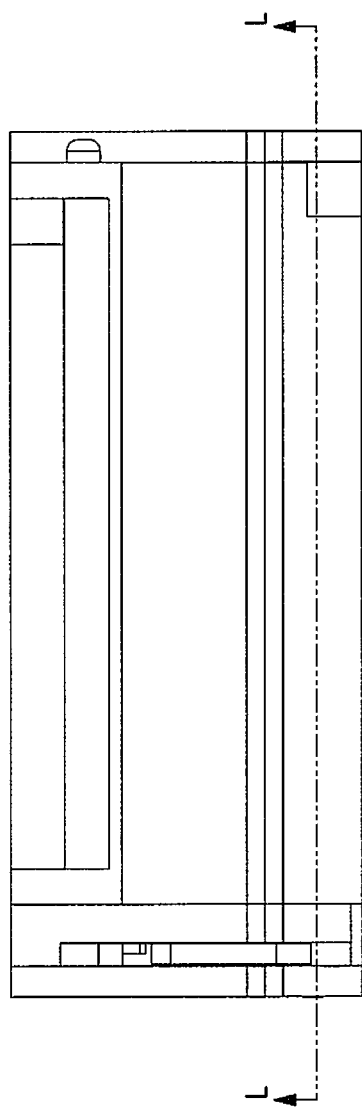
Figure 68B:
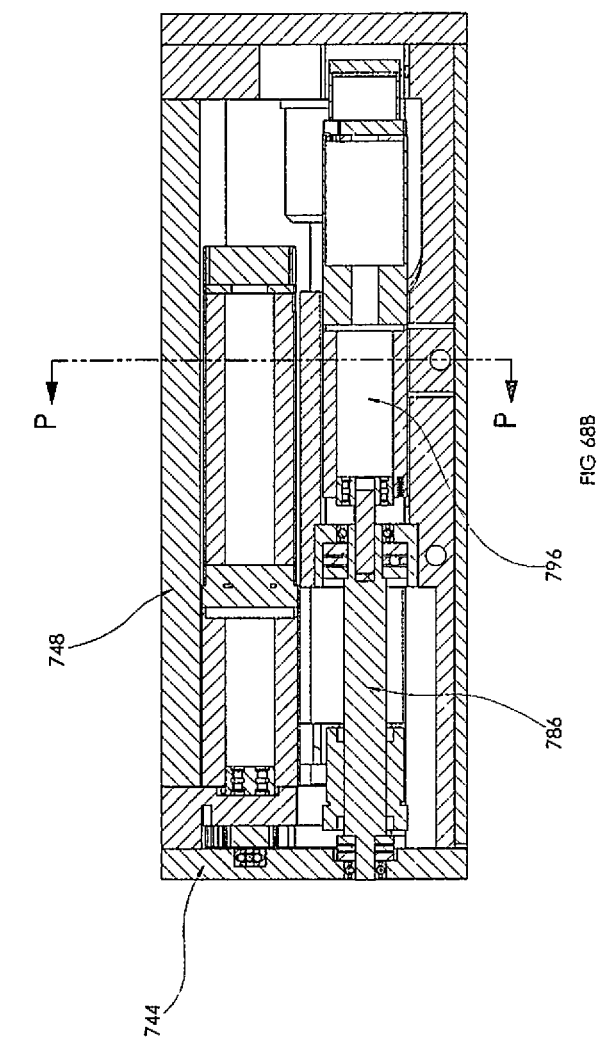
Figure 70:
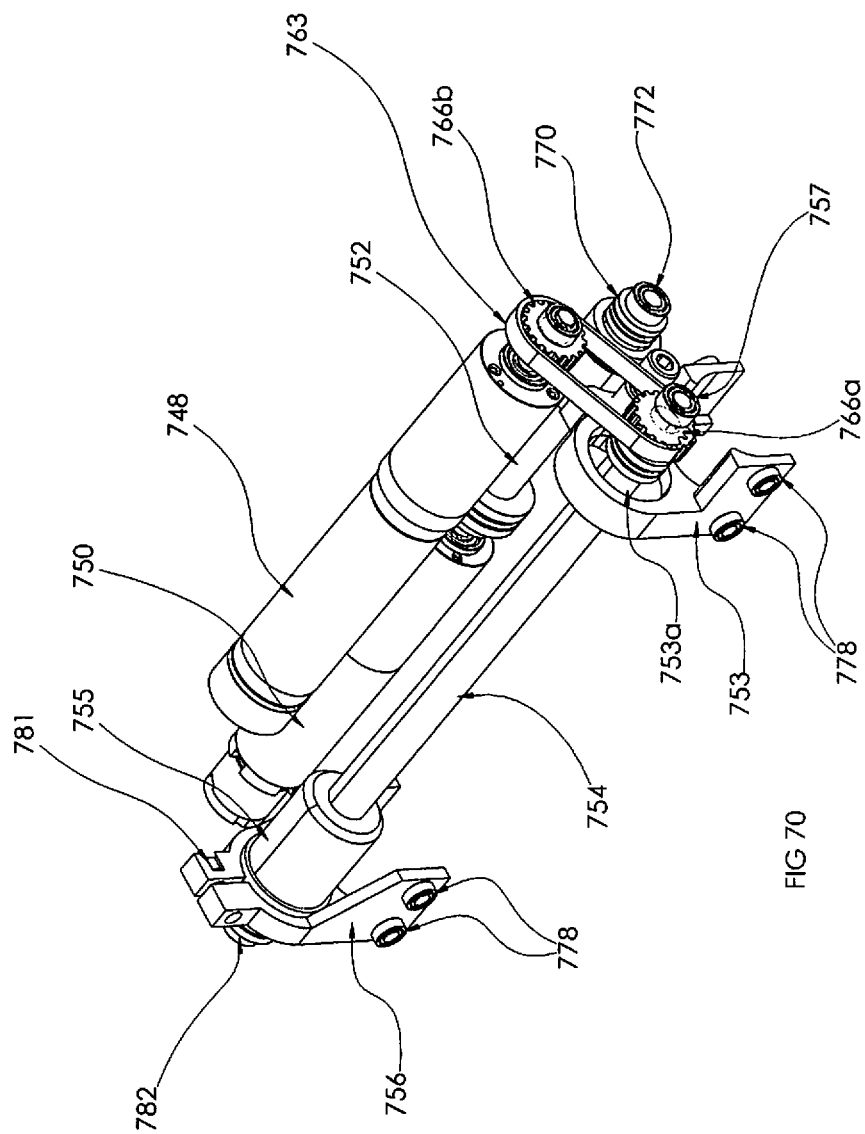
Figure 72:
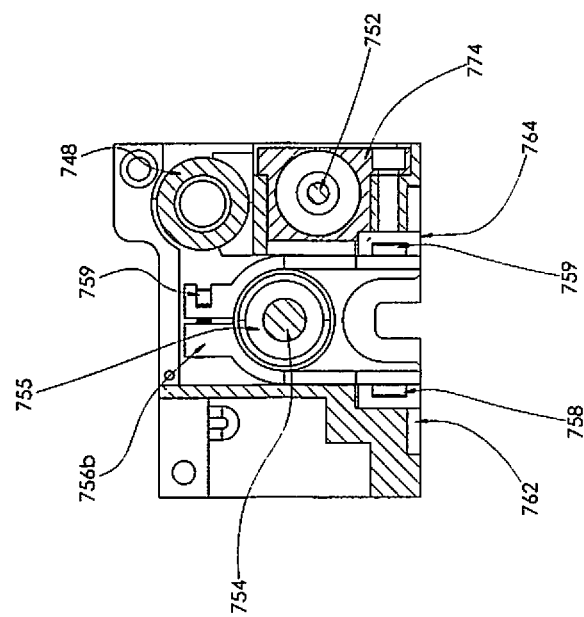
Figure 71:
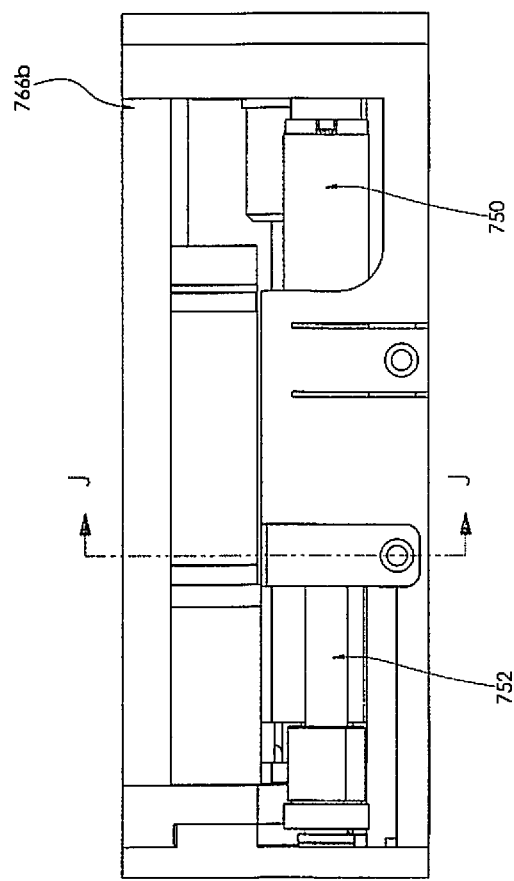

FIG. 60D is side view of the articulation screw assembly;

FIG. 61 is a side view of the power pack of FIG. 58A with portions removed to show internal components;

FIG. 62 is a front view of the deployment and articulation assemblies within the power pack;

FIG. 63 is a top view of the power pack of FIG. 58A;

FIG. 64 is a cross-sectional view taken along line E-E of FIG. 63;

FIG. 65 is a top view of the power pack of FIG. 58A with the covers removed;

FIG. 66 is a cross-sectional view taken along line L-L of FIG. 65;

FIG. 67A is a cross-sectional view taken along line M-M of FIG. 66;

FIG. 67B is a close up view of the area of detail designated in FIG. 67A;

FIG. 68A is identical to FIG. 65 provided for section line L-L and FIG. 68B is a cross-sectional view identical to FIG. 66 provided to show line P-P;

FIG. 69 is a cross-sectional view taken along line P-P of FIG. 68;

FIG. 70 is a perspective view of the deployment and articulation assemblies of the power pack of FIG. 58A;

FIG. 71 is a side view of the power pack of FIG. 58A with portions removed to show internal components;

FIG. 72 is a cross-sectional view taken along line J-J of FIG. 71; and

Figure 73:
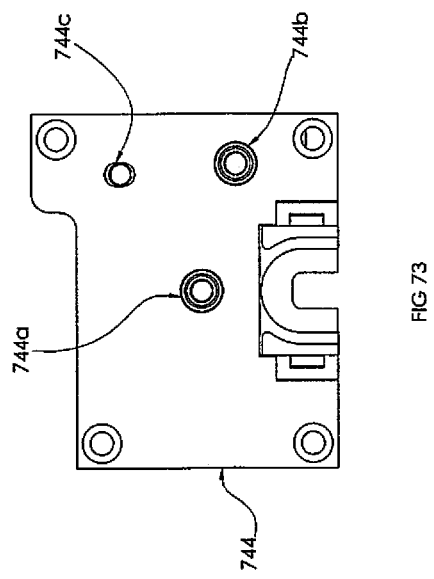

FIG. 73 is a front view of the distal plate of the chassis of the power pack of FIG. 58B.

DETAILED DESCRIPTION OF PREFERRED EMBODIMENTS

The present disclosure provides power packs, containing a battery and power train, which are loadable into a surgical stapler to power various functions of the surgical stapler to reduce the forces exerted by the clinician otherwise required if manual force was utilized. The present disclosure also provides surgical staplers designed to receive the power pack and to interact with the power pack to effect firing of the staplers. In some instances, the power pack can be used to effect articulation of the jaw assembly of the stapler to pivot the jaw assembly with respect to the longitudinal axis of the stapler. Each of these embodiments is discussed in detail below.

The power pack can also be utilized for powering endoscopic linear staplers, other types of staplers as well as other surgical instruments. Examples of these instruments are also discussed below.

The loadable power packs of the present disclosure are mountable into the handle housing of the surgical instrument, and are maintained in a sterile environment within the surgical instrument so they can be removed and reused. This enables the power pack to be removed from the stapler and reused in another procedure and/or instrument without the complexities, time, costs and risks of resterilization of the power pack. The sealed environment of the battery and power train within the housing also enables certain features/components to be used which might not otherwise be practical if sterilization of the internal power pack was required. Thus, by preventing contact between the power pack and the patient and/or bodily fluids and the external environment, resterilization is not required. The power pack can be used with surgical instruments discarded after use (fully disposable instruments), partially disposable surgical instruments or with fully reusable/sterilizable instruments with the advantage that the power pack need not be discarded or sterilized. Thus, the surgical stapler of the present disclosure advantageously reduces the time, resources and/or costs for preparing the surgical stapler for its next use.

The power packs are easily loadable in the surgical instrument, preferably the handle assembly or housing of the instrument, to easily and securely engage structure in the housing to effect movement of such structure in the instrument. The power packs are also easily disengageable from the structure for removal from the housing for subsequent reuse. The power packs can be configured so they can be loadable and engageable in various types of surgical instruments. The power pack is fully enclosed and sealed by the handle housing so there is no need to sterilize the power pack between uses. The power pack can include in some embodiments a replaceable battery pack so the battery can be changed during a surgical procedure.

Referring now to the drawings and particular embodiments of the present disclosure, wherein like reference numerals identify similar structural features of the devices disclosed herein, there are illustrated several embodiments of the surgical instruments and removable power pack of the present disclosure.

With reference to FIGS. 1-23B, the power pack is used with endoscopic linear staplers which are inserted through trocars and fire linear rows of surgical staples from a cartridge through tissue into contact with an anvil which forms the individual staples. The staplers include an openable compartment in the handle housing that enables easy loading of the power pack within the stapler. The staplers also provide a tight seal to protect the power pack from contaminants so that the power pack does not need to be sterilized for multiple uses.

The power pack is engageable with a staple drive (staple firing) mechanism of the surgical stapler so that once it is loaded in the stapler, actuation of the motor within the power pack effects firing of the staples through tissue. In some embodiments, the power pack is engageable with an articulation mechanism wherein actuation of the motor effects articulation of the stapler. The powered articulation can be in addition to the powered staple firing or alternatively the stapler could have powered articulation and manual staple firing. A specific embodiment of such powered articulation included with powered firing is shown in FIGS. 14A-23B and discussed in detail below.

The term "surgical fasteners" as used herein encompasses staples having legs which are deformed by an anvil, two part fasteners wherein a fastener or staple component with legs is received and retained in a second component (retainer), and other types of fasteners which are advanced through tissue of a patient in performing surgical procedures.

The term "proximal" as used herein denotes the region closer to the user and the term "distal" as used herein denotes the region further from the user. The terms "top" or "upper" and "bottom" or "lower" refer to the orientation of the instruments as shown in the orientation of the instrument in FIG. 2A, with the cover being on the top and the handle extending at the bottom.

Turning first to FIGS. 1-12, a first embodiment of the surgical stapler and removable power pack are illustrated. In this embodiment, the power pack, which contains a battery, motor, drive mechanism and stapler engagement structure, effects firing of the surgical fasteners (staples).

Figure 1:
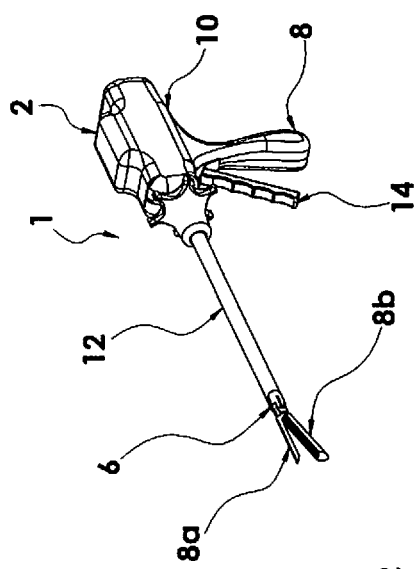
FIG. 1 is a perspective view of a first embodiment of the surgical stapler of the present disclosure having a removable power pack.
Figure 2A:
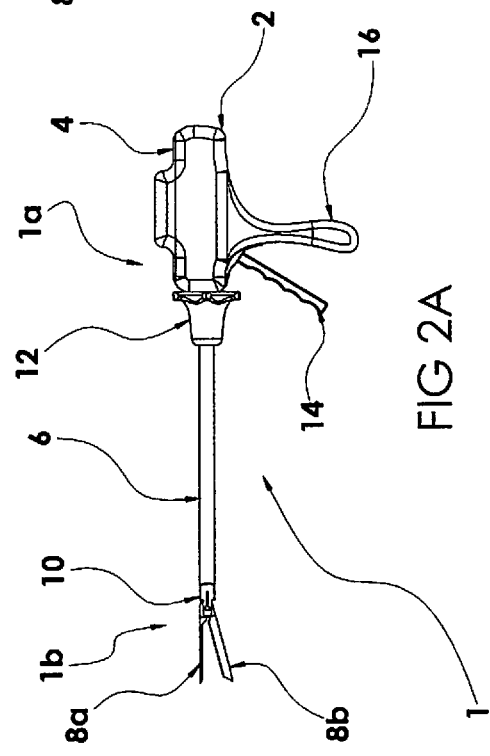
FIG. 2A is a side view of the surgical stapler of FIG. 1.
Figure 2B:
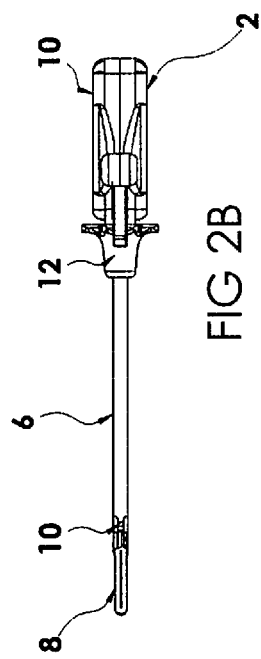
FIG. 2B is a bottom view of the surgical stapler of FIG. 1.
Figure 2C:
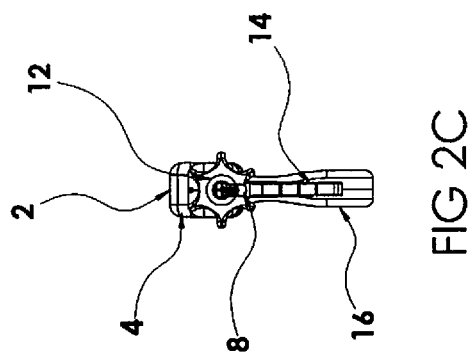
FIG. 2C is a front view of the surgical stapler of FIG. 1A.

The surgical stapler, also referred to herein as the surgical fastener applying instrument or surgical fastener applier, is designated generally by reference numeral 1 and includes a proximal portion 1a, a distal portion 1b and an elongated or endoscopic portion 6 (also referred to as an elongated tubular portion or shaft) extending between the proximal portion 1a and the distal portion 1b of the stapler. A handle assembly 2 with a housing 4 (also referred to herein as a handle housing) is positioned at the proximal portion 1a and is configured to house and protect internal mechanisms of the stapler 6 including the removable power pack when loaded (mounted) therein. At the distal portion 1b are opposing members, i.e., jaws, 8a, 8b, configured to clamp and constrain tissue during operation of the surgical stapler. At least one of the jaws is movable with respect to the other jaw from an open position to receive tissue between the jaws and a closed position to clamp tissue between the jaws. Thus, one of the jaws can be stationary and the other jaw movable with respect to the stationary jaw or alternatively both jaws can move, e.g., pivot, toward each other. In the embodiment of FIG. 1, jaw 8b, which contains at least one row of surgical fasteners (staples) is movable with respect to non-pivoting (stationary) jaw 8a which contains an anvil with staple forming pockets. Jaws 8a, 8b are collectively referred to herein as jaws 8. The fasteners are fired (advanced) from jaw 8b by linear movement of a firing mechanism which engages staple drivers within the jaw 8b which move transverse to the longitudinal axis, i.e., transverse to the direction of movement of the firing mechanism, to sequentially advance (from proximal to distal) the staples in the linear rows of staples from the jaw 8b and through tissue to engage the anvil pockets on jaws 8a for formation of the staples. Such firing of the staples is illustrated in FIG. 7C and discussed below.

The elongated tubular member 6 extends distally from the housing 4 and is configured to fit through a surgical port (trocar) used for laparoscopic surgery. The endoscopic portion 6 can be of varying dimensions and in some embodiments is configured to fit through a 10 mm trocar, although other dimensions for fitting through other size trocars are also contemplated such as trocars ranging from 5 mm to 15 mm. It is advantageous to minimize the diameter of the endoscopic portion to minimize the size of the patient's incision. With the jaws 8 in the clamped position, the outer diameter of the elongated member 6 is maintained as the cross-sectional dimension of the closed jaws 8 preferably does not exceed the cross-sectional dimension (i.e., diameter) of the tubular member 6.

The surgical stapler 1 can in some embodiments include a joint 10 that provides for the articulation of the opposing members 8, i.e., pivoting of the jaw assembly (jaws 8) to angular positions with respect to the longitudinal axis of elongated member 6. Articulation can be achieved by linear motion of elongated members extending through the endoscopic portion 6 which are slidable to angle the jaw assembly. A rotational member or knob 12 is configured to rotate, with respect to the handle assembly, the elongated member 6 and connected jaws 8 about the axis of the elongated member 6 to change the position of the jaws 8. Articulation is effected by manual manipulation of a lever adjacent the handle 2. A handle lever 14, linked to an axially movable clamping bar, is pivotable from a first position to a second position closer to stationary handle 16 to effect movement of the jaw 8b toward the jaw 8a from an open (unclamped) position to a clamping position, also referred to as a closed position of the jaws 8. Release of handle lever 14 returns the jaw 8b to its open position. Stationary handle 16 for grasping by the user is ergonomically designed for comfort of use. In summary, the surgical stapler operates by manual pivoting of the lever 14 toward stationary handle 16 to clamp the tissue between jaws 8, followed by powered firing of the staples from jaw 8b, through the clamped tissue and into contact with the staple forming pockets of the anvil of jaw 8b. Prior to firing, the jaws 8 can be rotated to a desired orientation by rotation of endoscopic portion 6 via knob 12 and/or articulated about joint 10, via movement of the elongated articulation members, to a desired angled position with respect to the longitudinal axis of endoscopic portion 6. In the embodiment of FIG. 1, articulation is performed by manual manipulation of a lever (not shown) which is operatively connected to an internal elongated member within tubular member 6 which extends to joint 10. A force applied to the internal elongated member pivots/articulates the jaws 8 about the joint 10. In later described embodiments (FIG. 14A), powered articulation is provided.

Figure 3D:
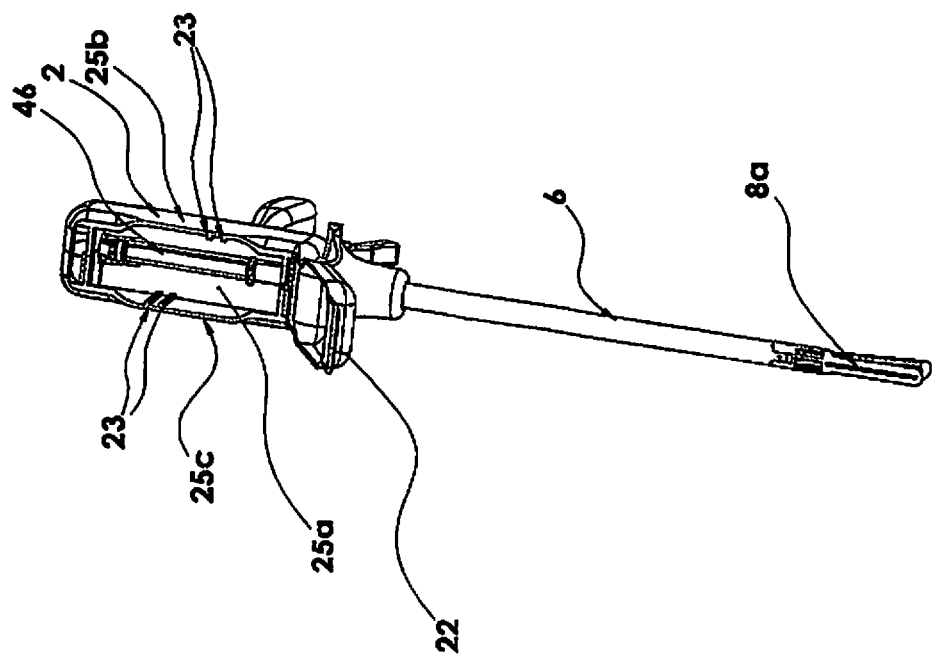
FIG. 3D is a top perspective view of the surgical stapler of FIG. 3A showing the compartment for receiving the power pack.

The housing 4 of the handle assembly 2 of the surgical stapler is configured to receive the loadable/removable power pack 18 in a receptacle (compartment) 20 as shown in FIGS. 3A and 3D. The receptacle includes a base 25a and side walls 25b and 25c having one or more guides 23 that cooperate with corresponding guiding structures 28 on the outer wall of the housing 19 of power pack 18 for proper alignment of the power pack 18 in the handle assembly 2 during insertion into the receptacle 20. In the embodiment of FIG. 3A, the guides 28 on power pack housing 19 are in the form of a pair of ribs or projections 28 extending transversely to a longitudinal axis of the power pack 18 for receipt within grooves formed between guides, e.g., ribs or projections, 23 of the compartment 20, also extending transversely with respect to a longitudinal axis of the stapler 1. In the illustrated embodiment, the ribs 23 are on opposing sides of the power pack 18 and are axially offset from each other, although in alternate embodiments they can be axially aligned. Additionally, a different number of ribs (axially or non-axially aligned) can be provided (with corresponding receiving structure in the compartment 20). It should be appreciated that alternatively, the grooves could be provided on the power pack 18 and the ribs provided in the compartment 20 to provide the guiding structure for the power pack 18. The guiding structure also helps to retain power pack 18 in position within the compartment 20. The power pack 18 has front and rear concave regions 19a, 19b to reduce its overall size.

The handle assembly 2 includes a cover 22 for opening and closing the receptacle 20. The compartment cover 22 is shown as being hingedly attached to the housing 4, but may alternatively be fully removable or attached in some other manner such as a slidable connection or the like. The cover 22 is shown pivotable mounted to a top portion of the housing 4 (in the orientation of FIG. 2A) for top loading of the power pack, although alternatively, side or bottom loading can be provided. The cover 22 is shown pivotable from a closed position of FIG. 2A to an open position of FIG. 3A to enable loading of power pack into the compartment 20 of the housing 4. In some embodiments, the cover 20 is spring loaded to an open position so it remains open for loading of the power pack 18. Once loaded, the cover 22 is pivoted about hinge 22a to its closed position. A latch can be provided to latch the cover 22 to the housing 4 in the closed position. When the cover 22 is in an open position, e.g., as shown in FIG. 3A, the power pack 18 may be removed from the receptacle 20 or inserted into the receptacle 20.

When the cover 22 is in a closed position, the seal of the cover 22 is in contact with the rim of the housing 2 such that the receptacle 20, and the power pack 18 when inserted into the receptacle 20, is sealed from the environment exterior to the surgical stapler. The top seal 24 can be attached to the cover 22 and in some embodiments can be in the form of an elastomer that is compressed by the housing, e.g., tightly fits slightly within the housing or is pressed on the rim of the housing 2. In other embodiments, the elastomer seal 24 can be on the housing 2, i.e., extending around the perimeter of the rim of the compartment 20, and is compressed by the cover 22 to seal between the cover 22 and housing 4. Other seals can also be provided within the surgical stapler to seal/protect the power pack 18 from contaminants, e.g., body fluids. These seals are discussed in more detail below.

Turning now to the power pack of the present disclosure, and with reference to FIGS. 4A-4I, the power pack 18 includes a motor assembly, battery and electronics contained within housing 19. More specifically, as shown in FIGS. 4A-4E, the power pack 18 includes a powering assembly including a motor 32 connected to a planetary gear box 34 configured to gear down the output of the motor 32 for proper drive speeds for firing staples from jaw 8b through the tissue into contact with the anvil of jaw 8a. The planetary gear box 34 drives a lead screw 36 through one or more gears operatively connected to the motor shaft. More specifically, upon rotation of the motor shaft by motor 32 in a first direction, gear 38 is rotated in the same first direction, causing rotation of the gear 30 in a second opposite direction due to the intermeshed teeth of gears 30 and 38. Lead screw 36 is operatively connected to gear 30 so that rotation of gear 30 causes rotation of lead screw 30 in the same direction. The power pack 18 includes a battery 33 which can be rechargeable outside the stapler when the power pack 18 is removed. The power pack 18 in some embodiments can include a power switch which is activated, i.e., turned on, by the clinician to start the motor and effect staple firing. In other embodiments, the motor can automatically turn on when the power pack is fully loaded or upon actuation of another control on the stapler housing 4. In some embodiments, the motor can automatically turn off when the power pack is removed from the stapler housing.

Connected to the end of lead screw 36 (the end opposite the connection to the gear 30) is a drive mechanism 40. The drive mechanism 40 is configured to move in a linear motion (in an axial direction) along the lead screw 36 in response to rotation of the lead screw 36. For example, the drive mechanism 40 may include internal threads that engage external threads of the lead screw 36 and may include slides engaged in a track that prevent the drive mechanism 40 from rotating and therefore cause the drive mechanism 40 to move linearly (axially) in response to rotation of the lead screw 36. As depicted in FIGS. 4A-4G, the power pack 18 has a compact configuration as the lead screw 36 extends alongside, slightly spaced from, the motor 32 and gear box 34, i.e., both the motor 32/gear box 34 and lead screw 36 extending longitudinally with the lead screw 36 parallel to the motor 32. The drive mechanism 40 is connected to a proximal end of lead screw 36 and extends proximally of the proximal end of the motor 32 in the illustrated embodiment.

The power pack 18 can have features/structure to constrain the motor 32. In the embodiment of FIG. 4F, such feature is in the form of proximal rails 27a and distal rails 27b spaced apart axially within the housing 19. Motor 32 is seated within proximal rails 27a and gear box 34 is seated within rails 27b, the rails 27a, 27b retaining the motor and preventing axial and rotational movement within the housing 19. Bearing or bushings 27c and 27d can also be provided to constrain the lead screw 36 at opposing ends, while allowing rotation thereof, thereby also constraining the motor. Other features can additionally or alternatively be provided to restrain the motor from axial movement while allowing rotation of the lead screw.

The drive mechanism 40 includes a first output flag or yoke 42, which is discussed in more detail below, configured to engage a staple firing mechanism, e.g., firing rod 46, extending longitudinally within the handle 4. The staple firing rod 46 is operatively connected to a firing rod in the endoscopic portion 6 which is operatively engageable with a series of staple drivers in jaw 8b to advance the fasteners (staples) from the fastener jaw 8b. Alternatively, the firing rod 46 can extend through the endoscopic portion 6 and itself engage the stapler drivers as shown in FIG. 7C. Thus, as the motor 32 generates rotational motion of the lead screw 36 through the planetary gear box 34 and the gears 38, 30, the drive mechanism 40 moves in linear motion along the lead screw 36. Such linear motion effects linear movement of the firing rod 46 (due to the engagement by the flag 42) which advances the staple driving mechanism to advance (fire) the staples out from jaw 8b through tissue and into contact with the anvil in jaw 8a. As noted above, the firing rod 46 can be a single element extending through the endoscopic portion 6 (see e.g., FIG. 7C) and terminating adjacent jaws 8 or alternatively can be attached to one or more components intermediate the firing rod 46 and jaws 8. In FIG. 7C, camming surface 46a of firing rod 46 engages staple drivers 47 to sequentially fire staples 51 as the firing rod 46 is advanced.

The power pack 18 can also include in some embodiments one or more sensors to indicate the position of the firing rod 46 to indicate to the clinician the status of staple firing. The embodiment of FIG. 4F illustrates an example of such sensors if they are provided. The power pack 18 has within the housing a proximal sensor 39a and a distal sensor 39b to sense the position of yoke 42 of the drive mechanism 40. Thus, sensor 39a senses the initial position of the yoke 42 (and thus the initial position of the firing rod 46) and at the end of the firing stroke, sensor 39b would indicate the end (final) position of the yoke 42 (and thus the final positon of the firing rod 46) which would indicate completed firing of the fasteners. The power pack 18 could also include an audible or visual indicator (viewable though the power pack housing 19 and instrument handle housing 4) actuated by the sensor to indicate to the clinician the position of the flag 42 and thus the completion or status of the firing stroke to fire the fasteners. The power pack 19 can also include sensors to detect the position of the articulation flag in the embodiments discussed below which have powered articulation. The sensor can include a potentiometer to determine the location during the firing stroke. It can also include an encoder to detect the position along the stroke. Alternatively, the stroke can also be identified by motor count. The power pack 18 in all other respects is identical to power pack 18 of FIG. 3A.

It is also contemplated that in alternate embodiments, the sensor(s) can be carried by the handle housing rather than (or in addition to) the power pack and utilized to detect the positioning of the flag 42 and/or firing rod 46 and/or detect the position of the articulation flag and/or articulation rod in the embodiments discussed below which have powered articulation.

It is also contemplated that a sensor(s) can be provided to detect the position of the clamping rod for clamping the jaws. The sensor can be provided in (or supported by) the power pack or alternatively the sensor(s) can be carried by the handle housing rather than (or in addition to) the power pack and utilized to detect the positioning of the jaws by detecting the position of the flag engaging the jaw clamping rod and/or detecting the position of the jaw clamping rod in the embodiments which have powered clamping.

Note the sensor can be provided in some embodiments; in other embodiments, no sensor(s) is provided.

The power pack in some embodiments has a battery pack that is removably mounted in or on the power pack. This is discussed in more detail in conjunction with FIGS. 35-37C.

Figure 6D:
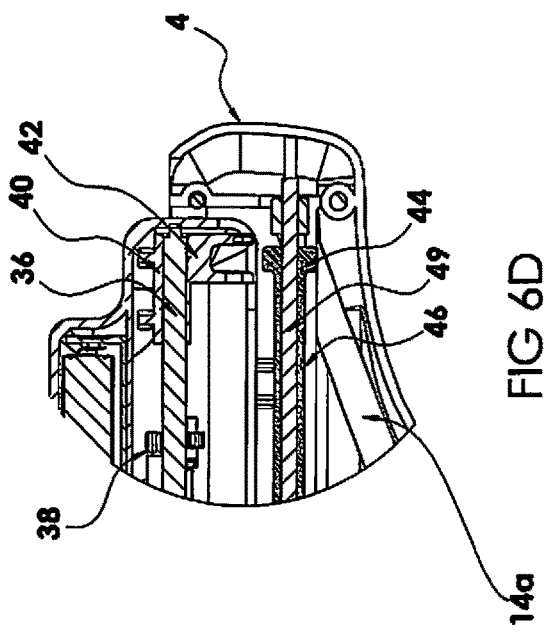
FIG. 6D is a close up view of the area of detail AR of FIG. 6C.
Figure 6A:
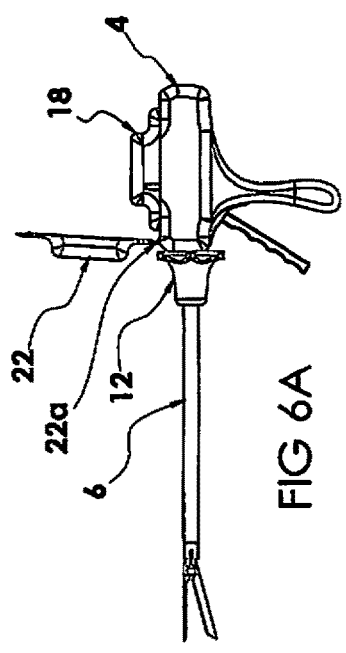
FIG. 6A is a side view of the surgical stapler of FIG. 1 showing the handle compartment cover in the open position and further showing the power pack in the process of being inserted in the compartment of the handle.
Figure 6B:
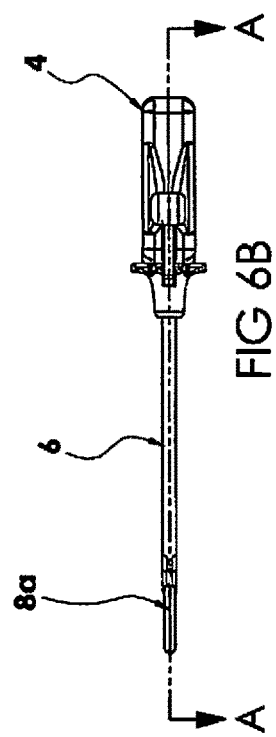
FIG. 6B is a bottom view of the surgical stapler of FIG. 6A.
Figure 6C:
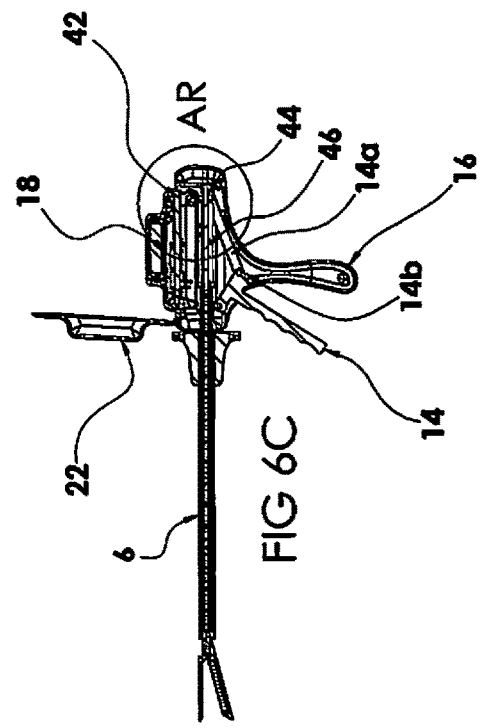
FIG. 6C is a cross-sectional view taken along line A-A of FIG. 6B.
Figure 16D:
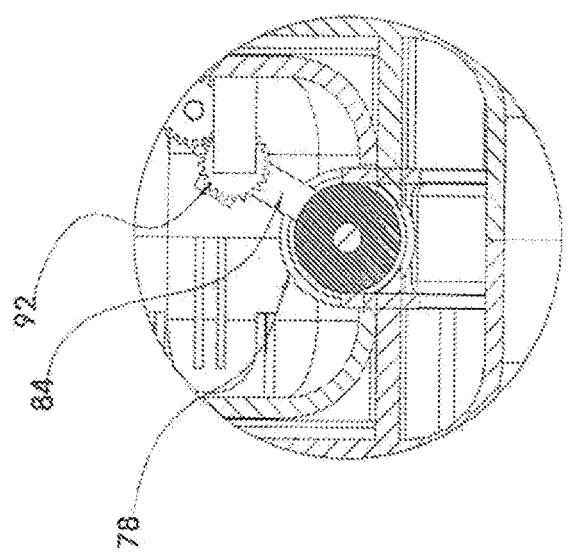
FIG. 16D is a close up view of the area of detail H of FIG. 16C.
Figure 16C:
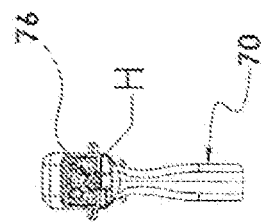
FIG. 16C is a cross-sectional view taken along line F-F of FIG. 15C.
Figure 16A:
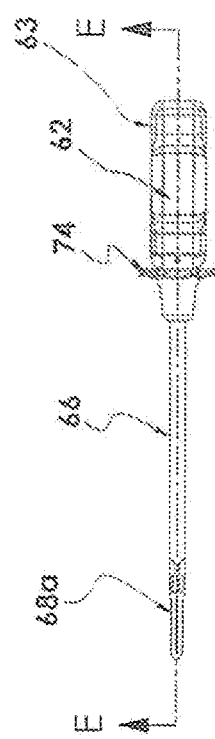
FIG. 16A is a top view of the surgical stapler of FIG. 14A, the view being the same as FIG. 14B but having section line E-E.
Figure 16B:
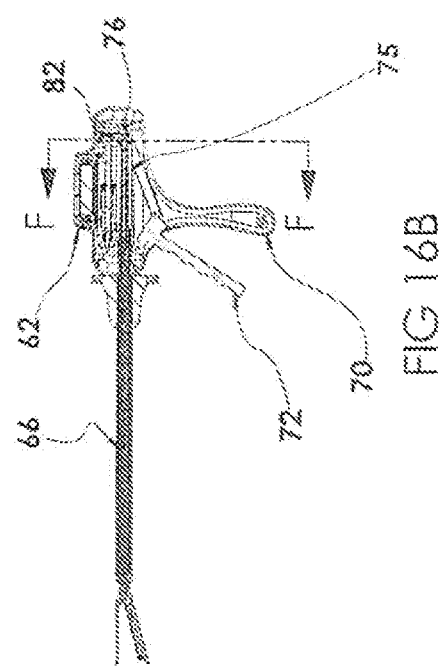
FIG. 16B is a side view of the surgical stapler of FIG. 14A, the view being the same as FIG. 14C but having section line F-F and identified area of detail G.
Figure 18B:
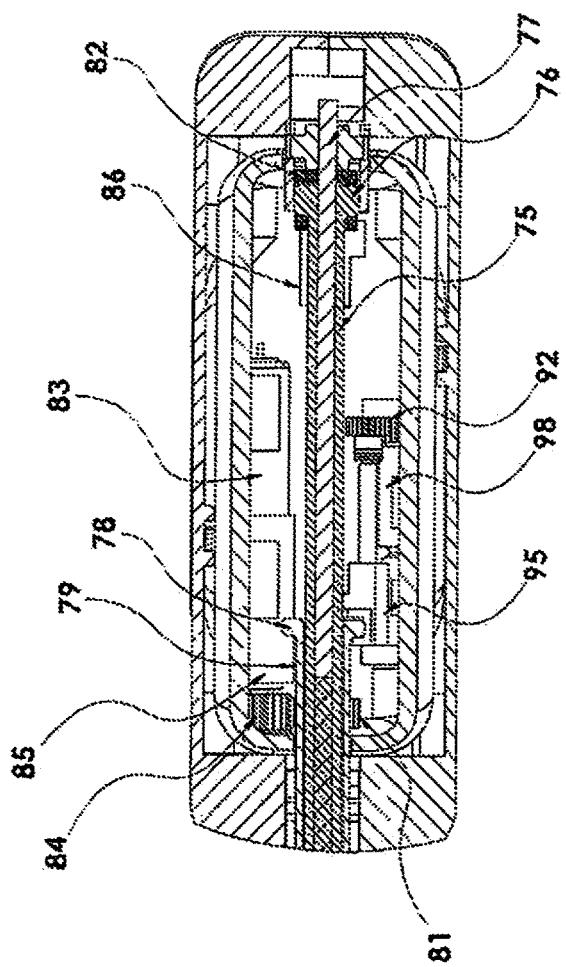
FIG. 18B is a close up view of the area of detail BA of FIG. 18A.
Figure 17:
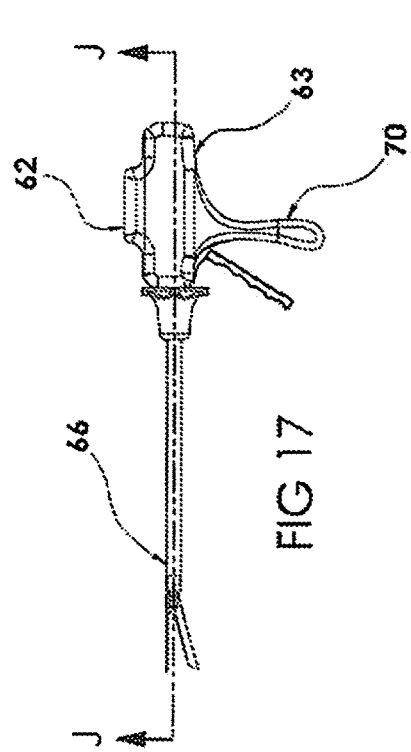
FIG. 17 is a side view of the surgical stapler of FIG. 14A, the view being the same as FIG. 14A but having section line J-J.
Figure 18A:
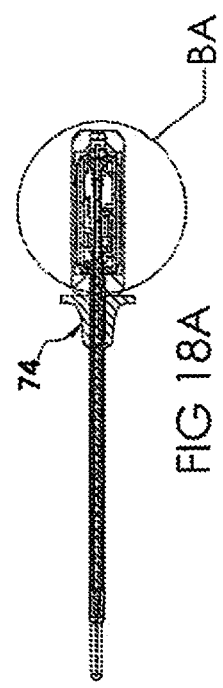
FIG. 18A is a cross-sectional view taken along line J-J of FIG. 17.
Figure 19C:
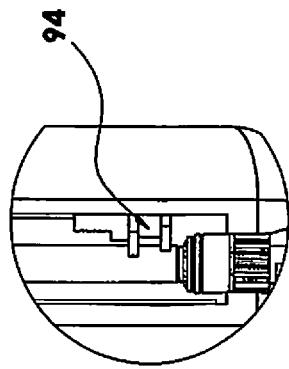
FIG. 19C is an enlarged view of the area of detail AL of FIG. 19A.
Figure 19B:
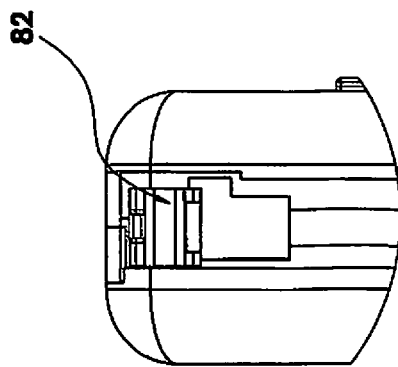
FIG. 19B is an enlarged view of the area of detail AK of FIG. 19A.
Figure 19A:
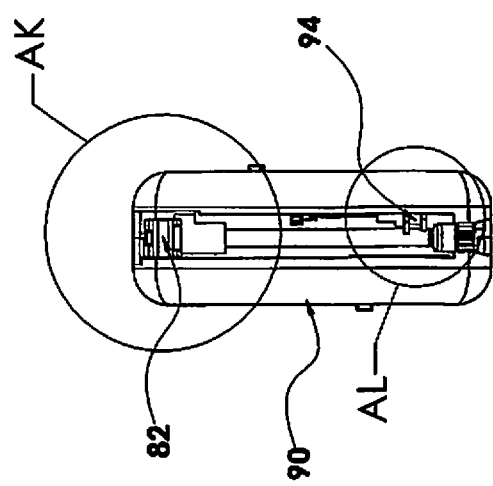
FIG. 19A is a top cutaway view of the power pack of FIG. 14A.
Figure 23B:
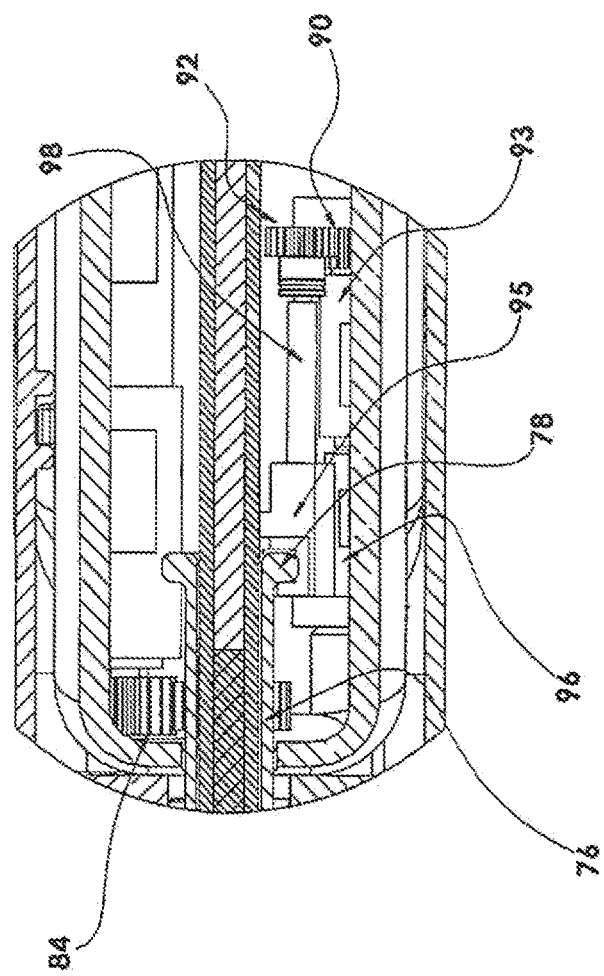
FIG. 23B is an enlarged view of the area of detail AU of FIG. 23A.
Figure 23A:
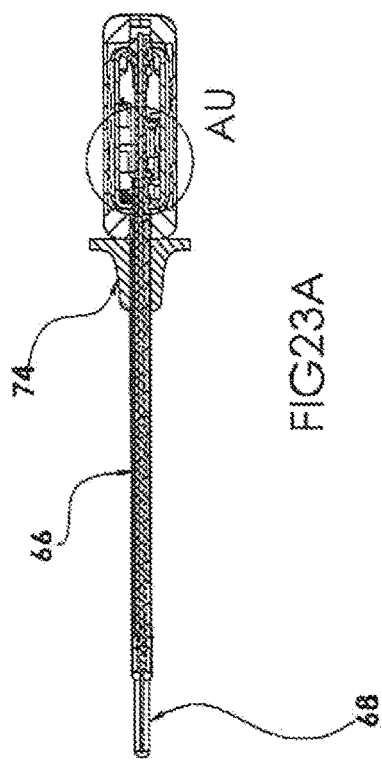
FIG. 23A is a cross-sectional side view of the surgical stapler of FIG. 14A, the view being the same as FIG. 18A but having and identified area of detail AU.
Figure 26C:
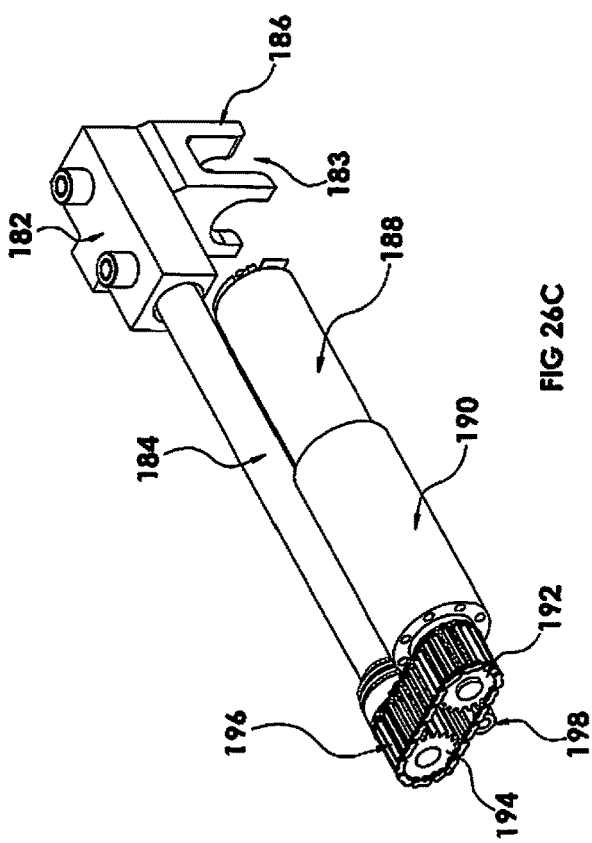
FIG. 26C is a perspective view of the motor and drive mechanism of FIG. 26A.
Figure 26D:
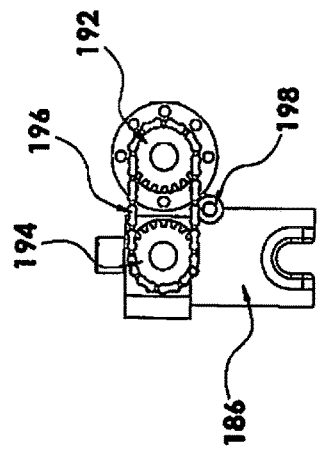
FIG. 26D is a front view of the motor and drive mechanism of FIG. 26A.
Figure 26A:
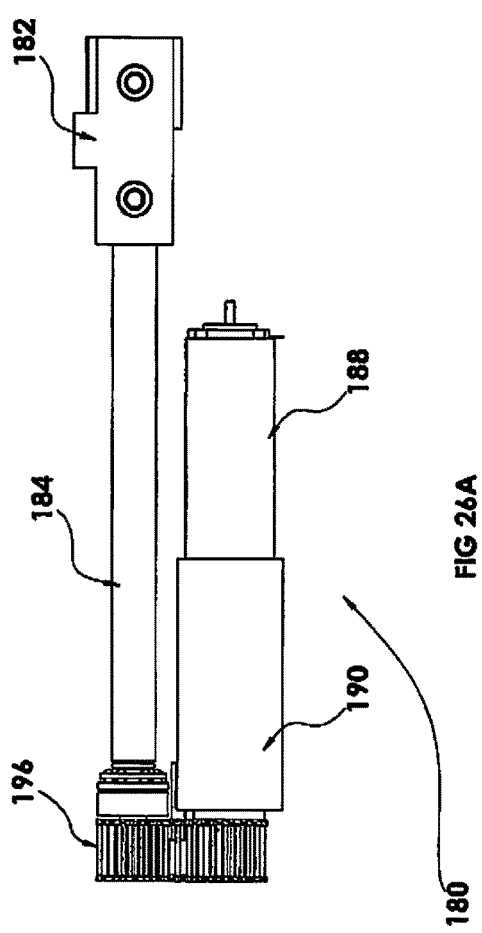
FIG. 26A is a top view of the motor and drive mechanism (assembly) of the power pack of another alternate embodiment having a belt drive.
Figure 26B:
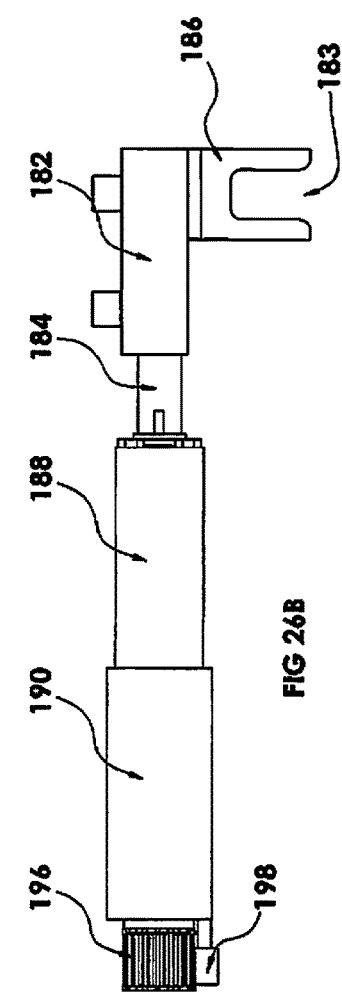
FIG. 26B is a side view of the motor and drive mechanism of FIG. 26A.
Figure 29C:
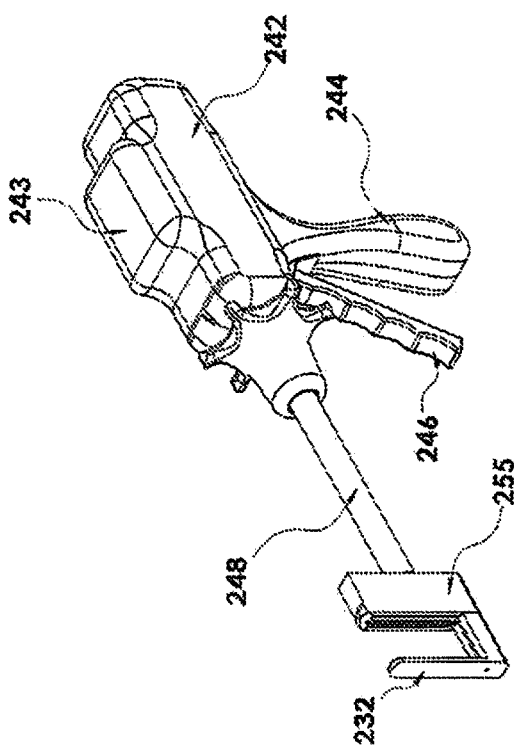
FIG. 29C is a perspective view of the linear stapler of FIG. 29A.
Figure 29D:
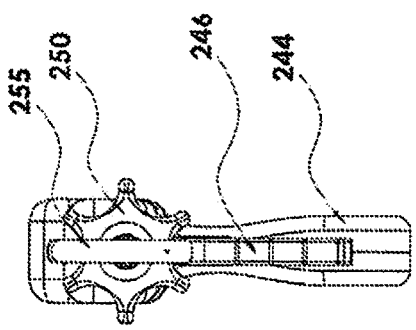
FIG. 29D is a front view of the linear stapler of FIG. 29A.
Figure 29A:
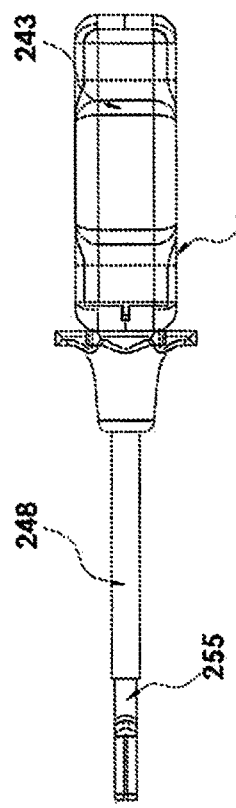
FIG. 29A is a top view of an alternate embodiment of the surgical instrument containing the power pack of FIG. 3A within the handle compartment, the surgical instrument being an open surgery linear stapler.
Figure 29B:
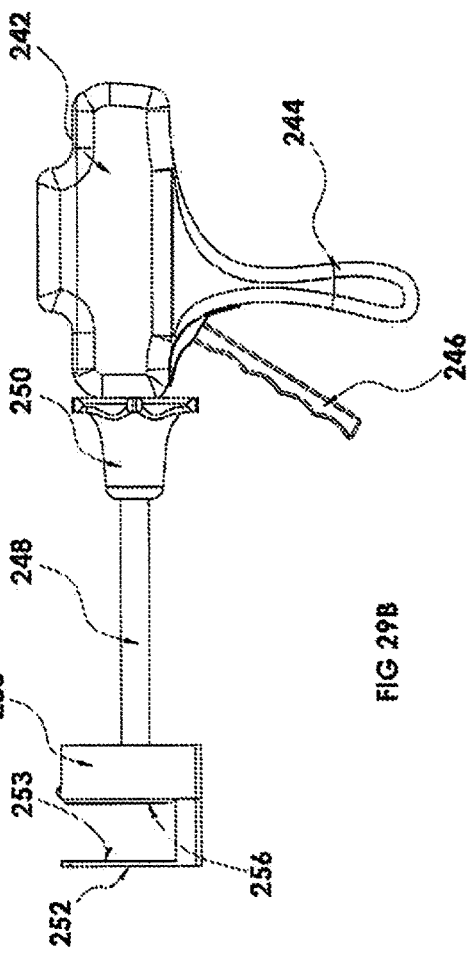
FIG. 29B is a side view of the linear stapler of FIG. 29A.

Turning now to the loading of the power pack 18 into the surgical stapler 1, as seen in FIGS. 6A-6D, the power pack 18 is in the process of being inserted into the receptacle 20 of housing 4. As shown, handle compartment cover 22 is open to provide access to compartment 20. The output flag 42 of the power pack 18 as noted above is driven by the motor assembly and is configured to engage and interact with structure within the handle assembly 2, e.g., firing rod 46, to control operation of the surgical stapler 1 when the power pack 18 is fully inserted into the receptacle 20. As can be appreciated in FIG. 6D, the output flag 42 is not fully engaged with the flange 44 of the firing rod 46. Also shown in FIG. 6D is the clamp bar 49 which is positioned within and concentric with firing rod 46. The clamp bar 49 is operatively connected to the pivotable handle 14 of stapler 1 via linkage 14a (pin 14b connects one end of handle 14 to the distal end of clamp bar 49). In this manner, movement of pivotable handle 14 toward stationary handle 16 causes the operatively connected jaw clamping mechanism, e.g., clamp rod 49, to be advanced distally to pivot jaw 8b toward jaw 8a to clamp tissue between the two jaws 8. Note that for clamping, clamp bar 49 slides linearly within a lumen of firing rod 46; for staple firing, firing rod 46 moves linearly over clamp bar 49.

The output flag 42 of power pack 18 is configured to engage a bossed end 44 of the firing rod 46 when the power pack 18 is fully inserted into the receptacle 20 of the handle assembly 2. As shown, the output flag (yoke) 42 has a receiving or mounting feature or member (also referred to as the engagement feature (member) or firing rod engagement feature (member) in the form of two arms 43a and a slot 43b therebetween, configured to frictionally (and releasably) engage the bossed end 44, the feature aligning with the bossed end 44 during insertion. (The aforedescribed guiding structure on the power pack 18 and internal wall of the compartment 20 aid such alignment).

FIGS. 8A, 8B and 10 show the power pack 18 fully inserted into the compartment 20 of stapler 1. In this position, the output flag 42 is engaged with the bossed end 44 of the firing rod 46. Note the firing rod 46 is able to rotate when the first output flag 42 of the power pack 18 is engaged with the bossed end 44. When the power pack 18 is secured to the firing rod 46 by the first output flag 42, linear motion generated at the first output flag 42 by the motor actuated drive assembly is transferred to the firing rod 46, which moves linearly to actuate the staple firing mechanism. That is, rotation of the gear 30 effects axial rotational movement of the drive screw 36 which effects axial (linear) movement of the connected drive mechanism 40 to effect axial (linear) movement of the associated drive mechanism (rod) engaging member (i.e., flag 42). It should be appreciated that flag 42 provides one example of the releasable attachment (engagement member) of the motor assembly to the firing rod 46, it being understood that other mounting (engagement) members or features are also contemplated to engage the firing rod to advance it axially.

In use, the cover 22 of stapler 1 is opened and the power pack 18 is inserted into receptacle 20 of sterile handle assembly 2 (of sterile stapler 1), with the output flag 42 of the power pack 18 engaging a corresponding feature, e.g., boss 44 of elongated drive rod 46, in the handle assembly 2 as discussed above. Then, the cover 22 is closed to seal the power pack 18 within the receptacle 20 from the external environment and the surgical stapler 1 may be actuated, i.e., manually clamped, articulated and/or rotated if desired, and the motor actuated to effect staple firing. After applications of fasteners and release (unclamping of the jaws from tissue), the cover 22 can be opened and the power pack 18 removed and charged while the stapler and handle assembly are resterilized if the stapler is a reusable instrument or the stapler and handle assembly are disposed of if the stapler is a single use disposable instrument. The power pack 18, due to its sealed configuration discussed above, can be reused without requiring sterilization by insertion into the receptacle 20 of a resterilized handle assembly or a sterile handle assembly of an unused disposable handle assembly. Thus, as can be appreciated, the removable power pack 18 does not need to be subjected to the sterilization process and, therefore, contact between the harsh temperatures and/or chemicals of the sterilization process is advantageously avoided. Also, by being able to reuse the power pack without sterilization, significant cost savings are achieved compared to if the power pack is not resterilizable, is disposed of along with the disposable stapler.

Note that in the embodiment of FIGS. 1-12 (and FIGS. 14-23B discussed below), rotational motion caused by the motor is translated into linear motion. This is shown schematically in FIG. 5A wherein the drive rod in the handle housing is engaged by the motor driven drive assembly of the power pack 18 (or power pack 90 which is discussed below) moves linearly (axially) to effect linear (axial) movement of the drive member in the stapler, e.g., extending through the endoscopic portion, which effects staple firing. Alternatively, or in addition, a drive assembly of the power pack engages a drive rod in the housing which moves linearly to effect linear movement of a drive rod to effect clamping of the jaws and/or a drive assembly of the power pack engages a drive rod in the housing which moves linearly to effect linear movement of a drive member to effect articulation of the jaw assembly. Alternatively, the intermediate drive member could be omitted and the drive rods directly effect respective clamping and articulation.

Figure 5A:
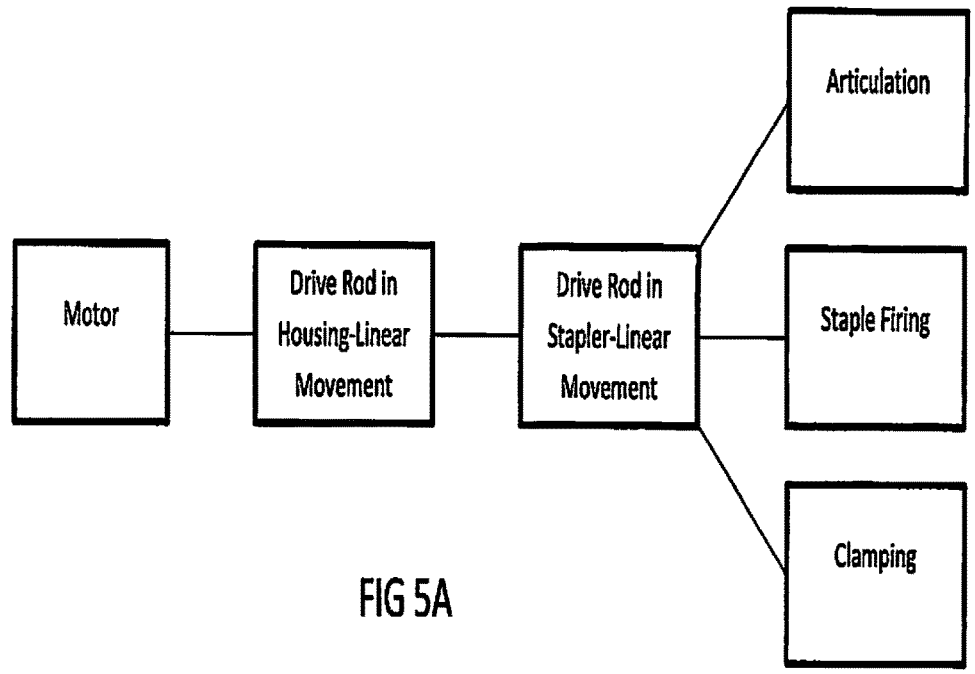
FIG. 5A is a schematic view illustrating transition from rotational movement to linear movement to effect a function of the surgical stapler.
Figure 5B:
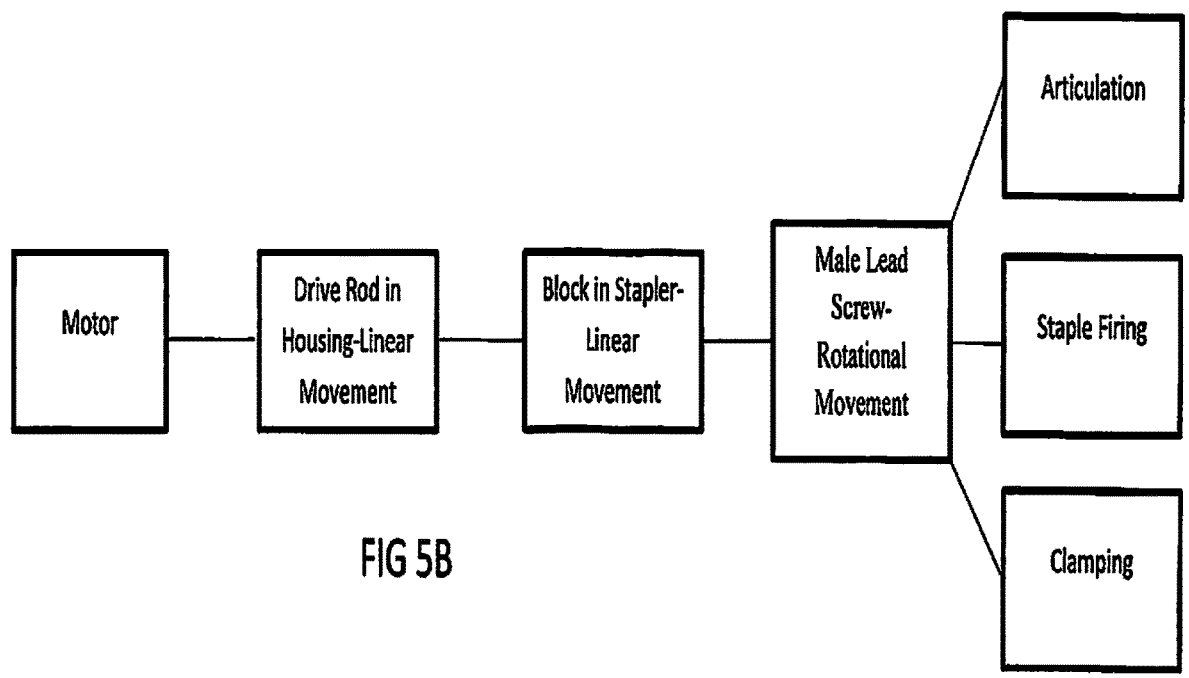
FIG. 5B is a schematic view of an alternate embodiment illustrating transition from rotational movement to linear movement to rotational movement to effect a function of the surgical stapler.

In an alternate embodiment, shown schematically in FIG. 5B, linear motion is converted back to rotational movement. That is, the handle housing has a receptacle (compartment) to receive power pack 18 (or power pack 90) which has one or more engagement features to engage or couple to a firing rod for firing staples, a clamping rod for clamping the jaws about tissue and/or an articulation rod to articulate the jaws to angular positions with respect to the longitudinal axis. The drive rod is connected at its distal end to a block in the stapler having a female thread or a slotted guide engagement to prevent rotation of the block and enable linear movement. (The drive rod could alternatively be attached to other structure). The block is connected to a male lead screw which is engaged at its proximal end via threaded engagement to the distal end of the block. The lead screw is connected at its distal end to a component that requires rotation to effect operation of the stapler, such as effecting staple firing, clamping and/or articulation. A bearing can be provided to keep the lead screw on center and control axial motion. In use, actuation of the motor advances the drive assembly of the power pack linearly which is engaged with and advances the drive rod in the handle housing linearly (axially). Linear movement of the drive rod causes linear movement of the block positioned in the endoscopic portion (or alternatively positioned in the handle housing). Linear movement of the block causes rotation of the male lead screw to engage a staple firing component(s) to effect staple firing. Alternatively, or in addition, the drive assembly, or a separate drive assembly (assemblies), engages a drive rod in the housing which moves linearly to effect linear movement of a block to cause rotation of the lead screw to move a jaw clamping component(s) to effect clamping of the jaws and/or engages a drive rod in the housing which moves linearly to effect linear movement of a block to cause rotation of the lead screw to move an articulation component(s) to effect articulation of the jaws.

In the embodiment of FIGS. 1-12, the power pack 18 actuates the firing rod 46 to fire the staples while other steps are performed manually. In summary, in this embodiment, in use, the jaws 8a, 8b are moved to the closed (clamped) position manually by a hand actuated lever or control. Also, in this embodiment, the jaws 8 are articulated with respect to the longitudinal axis of the endoscopic portion manually by a hand actuated lever or control. Thus, the clinician would manually clamp the jaws, manually rotate the endoscopic portion and attached jaws 8, and manually articulate the jaws by manipulation of controls at the proximal end of the stapler 1, e.g., at the handle 4.

FIGS. 1-12 show one embodiment of an endoscopic linear stapler that can be used with the power pack 19 of the present disclosure. However, the power pack 18 is not limited to such endoscopic staplers. For example, FIGS. 13A and 13B illustrate another endoscopic linear stapler, designated by reference numeral 100, that can be powered by power pack 18. Stapler 100 has a handle 102 manually pivotable towards stationary handle 103 for clamping of the jaws 108a, 108b, an endoscopic portion 106 extending from the handle housing 101, a jaw assembly 104 containing jaws 108a, 108b and connector 107a extending proximally from shaft or tube 107 for attachment to the endoscopic portion 106 so that the jaw assembly 104 can be replaced multiple times in a single surgical procedure to provide additional rows of staples to tissue. The stapler 100 also includes a rotation knob 109 for rotation of the endoscopic portion 106, with respect to the handle housing, to rotate the attached jaws 108a, 108b. The stapler 100 can also include an articulation knob to articulate the jaws. Power pack 18 is shown in FIG. 13A prior to loading within the handle housing 101 and shown in FIG. 13B fully loaded (inserted) within the handle housing 101. A cover (not shown) can be provided to seal the power pack 18 from the external environment. As in the embodiment of FIGS. 1-12, the flag 42 extending from lead screw 36 engages a firing rod within the handle housing 101 to effect movement of a firing rod to fire the staples when the motor of the power pack 18 is actuated. Power pack 90 having articulation described below can also be utilized with stapler 100.

FIGS. 13C and 13D illustrate another endoscopic linear stapler that can receive the power pack 18. Endoscopic linear stapler 110 has a handle 112 manually pivotable toward stationary handle 113 for clamping of the jaws 118a, 118b, an endoscopic portion 116 extending from the handle housing 111, and a jaw assembly at the distal end of the endoscopic portion 116. The stapler 110 also includes a rotation knob 119 for rotation of the endoscopic portion 116 to rotate the jaws 118a, 118b. The stapler 110 can also include an articulation knob to articulate the jaws 118a, 118b. Power pack 18 is shown in FIG. 13C prior to loading within the handle housing 112 and shown in FIG. 13D fully loaded (inserted) within the handle housing 112. A cover (not shown) can be provided to seal the power pack 18 from the external environment. As in the embodiment of FIGS. 1-12, the flag 42 extending from lead screw 36 engages a firing rod within the handle housing 111 to effect movement of a firing rod to fire the staples when the motor of the power pack 18 is actuated. Power pack 90 having articulation described below can also be utilized with stapler 110.

FIGS. 30A-30D illustrate another type of endoscopic linear stapler that can receive and be powered by the power pack 18. Stapler 260 has a handle 266 manually pivotable towards stationary handle 264 for clamping of the jaws, an endoscopic portion 268 extending from the handle housing 267, and a jaw assembly containing jaws 272a, 272b. The endoscopic portion 268 is flexible which enables use in various endoscopic procedures. The stapler 260 also includes a rotation knob 270 for rotation of the endoscopic portion 268 to rotate the jaws 272a, 272b. Power pack 18 is shown fully loaded (inserted) within the handle housing 262 and cover 263 closed to seal the power pack 18 from the external environment. As in the embodiment of FIGS. 1-12, the flag 42 extending from lead screw 36 engages a firing rod within the handle housing 262 to effect movement of a flexible firing rod extending through flexible endoscopic portion 268 to fire the staples when the motor of the power pack 18 is actuated. Power pack 90 having articulation described below can also be utilized with stapler 260.

The power pack 18 is also not limited to use with endoscopic linear staplers, nor is it limited to use with staplers. FIGS. 28A-29D illustrate two examples of different staplers. As in the endoscopic linear staplers discussed herein, these staplers can also have a knife bar to cut tissue between the rows of staples applied to the tissue.

By way of example, the power pack 18 can be used with a circular stapler that applies circular arrays of staples such as shown in FIGS. 28A-28D. Surgical stapling instrument 220 can receive and be powered by the power pack 18 of the present disclosure. Stapler 220 has a handle 226 manually pivotable towards stationary handle 264 for clamping of the jaws, an elongated tubular portion 228 extending from the handle housing 222, and a jaw assembly having an anvil (jaw) 232 and a cartridge (jaw) 235 containing circular arrays of fasteners (staples). The anvil 232 has a proximal clamping surface 233 and is movable by anvil rod 234 toward the cartridge 235 to clamp tissue between the anvil clamping surface 233 and distal clamping surface 236 of cartridge 235 by manual movement of handle 226 toward stationary handle 224. The stapler 220 also includes a rotation knob 230 for rotation of the elongated portion (shaft) 228 to rotate the jaws 232, 235. Power pack 18 is shown fully loaded (inserted) within the handle housing 222 and cover 223 is shown closed to seal the power pack 18 from the external environment. As in the embodiment of FIGS. 1-12, the flag 42 extending from lead screw 36 engages a firing rod within the handle housing 222 to effect movement of a firing rod extending through elongated portion 228 to fire the circular arrays of staples when the motor of the power pack 18 is actuated. Power pack 90 having articulation described below can also be utilized with stapler 220.

By way of another example, the power pack can be used with a linear stapler that applies transverse rows of staples in a linear direction, i.e., parallel to the longitudinal axis of the stapler, such as shown in FIGS. 29A-29D. Surgical stapling instrument 240 can receive and be powered by the power pack 18 of the present disclosure. Stapler 240 has a handle 246 manually pivotable towards stationary handle 244 for clamping of the jaws, an elongated tubular portion 248 extending from the handle housing 242, and a jaw assembly containing an anvil (jaw) 252 and a cartridge (jaw) 255 containing linear rows of fasteners (staples) arranged perpendicular to the longitudinal axis of the stapler 240. The proximal anvil clamping surface 253 of anvil 252 and distal clamping surface 256 of cartridge 255 are brought into approximation by manual movement of handle 246 toward stationary handle 244 which advances cartridge 255 toward anvil 252. (Alternatively the anvil could be retracted toward the cartridge). The stapler 240 also includes a rotation knob 250 for rotation of the elongated portion (shaft) 248 to rotate the elongated portion 248 and jaws 252, 255. Power pack 18 is shown fully loaded (inserted) within the handle housing 242 and cover 243 is shown closed to seal the power pack 18 from the external environment. As in the embodiment of FIGS. 1-12, the flag 42 extending from lead screw 36 engages a firing rod within the handle housing 242 to effect movement of a firing rod extending through elongated portion 248 to fire the staples from cartridge 255 when the motor of the power pack 18 is actuated. Power pack 90 having articulation described below can also be utilized with stapler 240.

The power pack 18 can also be used with single firing instruments that fire a single staple, clip, tack, etc. into body tissue. Two examples of such instruments are illustrated in FIGS. 31A-31D and FIGS. 34A-34D. Turning first to the instrument 280 of FIGS. 31A-31D, by way of example, surgical clip applying instrument 280 can receive and be powered by the power pack 18 of the present disclosure. Stapler 280 has a handle 286 manually pivotable towards stationary handle 284 for loading a clip into the jaws, an elongated tubular portion 288 extending from the handle housing 282, and a pair of pivotable jaws 292 which support a clip therebetween. Closing of the jaws 292 crimps the clip about tissue. The clip applier 280 also includes a rotation knob 290 for rotation of the elongated portion (shaft) 288 to rotate the jaws 292. Power pack 18 is shown fully loaded (inserted) within the handle housing 282 and cover 283 is shown closed to seal the power pack 18 from the external environment. As in the embodiment of FIGS. 1-12, the flag 42 extending from lead screw 36 engages a rod within the handle housing 282 operably connected to a clip closing mechanism to effect movement of the clip closing mechanism to close the jaws to apply to tissue a surgical clip supported by the jaws 292. The power pack 18 can also have a motor powered drive assembly for advancing the clip into the jaws 292, the drive assembly engageable with a clip feed mechanism.

Another example of a single firing instrument is illustrated in FIGS. 34A-34D and designated generally by reference numeral 340. Instrument 340 can receive and be powered by the power pack 18 of the present disclosure. Instrument 340 has a handle 346 manually pivotable towards stationary handle 344 for angling the surgical tack and an elongated tubular portion 348 extending from the handle housing 342. Tacker support 345 is pivotable relative to the longitudinal axis by movement of handle 346 which is operably connected to an elongated member which pivots support 345. The instrument 340 also includes a rotation knob 350 for rotation of the elongated portion (shaft) 348. Power pack 18 is shown fully loaded (inserted) within the handle housing 342 and cover 343 is shown closed to seal the power pack 18 from the external environment. As in the embodiment of FIGS. 1-12, the flag 42 extending from lead screw 36 engages a rod within the handle housing 342 operably connected to a tack firing mechanism to effect advancement of the tack 347 into tissue. The power pack 18 can also be provided with a motor powered drive assembly to pivot support 345.

In the embodiments of FIGS. 1-12, a gear mechanism is driven by the motor to rotate the lead screw to advance the drive mechanism to effect firing of the staples. In the alternate embodiments of FIGS. 24A-27D, a belt drive mechanism is used to effect firing. The belt drive mechanism is contained in the power pack 18 in the same manner as the gear mechanism of the foregoing embodiments, and thus the power pack for the belt drive would include the housing 19 of the configuration of FIG. 1 and loaded in the stapler 1 in the same manner as power pack 18 described above. The belt drives of FIGS. 24A-27D are described below for use with stapler 1 of FIG. 1A but can be used in the other surgical staplers and instruments disclosed wherein which are designed to receive power pack 18 or power pack 90 for powered actuation.

Turning first to the embodiment of FIGS. 24A-24D, the belt drive assembly (mechanism) includes a motor 148 connected to a planetary gear box 150 configured to gear down the output of the motor 148 for proper drive speeds for firing staples from jaw 8a through the tissue into contact with the anvil of jaw 8b. The planetary gear box 150 drives a lead screw 144 via the drive belt operatively connected to the motor shaft. More specifically, upon rotation of the motor shaft by motor 148, first rotatable disc 152 (also referred to as the first wheel or pulley) is rotated in a first direction, causing movement of belt 156 and rotation of second rotatable disc 154 (also referred to as the second wheel or pulley). Note the two discs 152, 15 are spaced apart and not in contact. Lead screw 144 is operatively connected to disc 154 so that rotation of disc 154 causes rotation of lead screw 144 in the same direction. The power pack 18 includes a battery which can be rechargeable outside the stapler when the power pack 18 is removed. The motor 148 is actuated in the various ways described above with regard to power pack 18 of FIG. 3A. A tensioner can be provided such as tensioner 158, illustratively in the form of a tension disc or wheel, to apply a force against the belt 156. In the orientation of FIGS. 24C and 24D, the tensioner 158 is positioned underneath the drive belt 156 and applies an upward tensioning force against the belt 156 in a direction toward discs 152, 154. Other types of mechanisms to apply a tensioning force to the belt are also contemplated for use in the embodiments of FIGS. 24A-27D if such tensioning of the drive belt 156 is desired.

Connected to the end of lead screw 144 (the end opposite of the connection to the disc 154) is a drive mechanism 142. The drive mechanism 142, like drive mechanism 40 of FIG. 3A, is configured to move in a linear motion (in an axial direction) along the lead screw 144 in response to rotation of the lead screw 144. For example, as in the drive mechanism 40, drive mechanism 142 may include internal threads that engage external threads of the lead screw 144 and may include slides engaged in a track that prevent the drive mechanism 142 from rotating and therefore cause the drive mechanism 142 to move linearly in response to rotation of the lead screw 144. As shown, the lead screw 144 extends alongside, slightly spaced from, the motor 148 and gear box 150, i.e., both the motor 148/gear box 150 and lead screw 144 extending longitudinally with the lead screw 144 parallel to the motor 148. The drive mechanism 142 extends proximally of the proximal end of the motor 148 in the illustrated embodiment.

The drive mechanism 142, like drive mechanism 140 of FIG. 3A, includes a first output flag or yoke 146 with slot 143 configured to engage a staple firing rod 46 extending longitudinally within the handle 4. The flag 146 is the same as flag 42 of FIG. 4A and engages the staple firing rod 46 in the same manner as flag 42. Therefore, for brevity, further discussion of flag 146 and it engagement with firing rod 46 is not provided as the structure and function of flag 42, and alternative firing rod engagement features, are fully applicable to flag 146 of FIGS. 24A-24D. In brief, as the motor 148 generates rotational motion of the lead screw 144 through the drive belt, the drive mechanism 144 moves in linear motion along the lead screw 144 to effect linear movement of the firing rod 46 which advances the staple driving mechanism to advance (fire) the staples out from jaw 8b through tissue and into contact with the anvil in jaw 8a.

FIGS. 25A-25D illustrate an alternate embodiment of a belt drive mechanism. Belt drive mechanism (assembly) 160 is identical to belt drive 140 except for the different sized discs (wheels). That is, assembly 160 has a motor 168 connected to a planetary gear box 170 configured to gear down the output of the motor 168. The planetary gear box 170 drives a lead screw 164 through the belt drive operatively connected to the motor shaft. Upon rotation of the motor shaft by motor 168, first disc 172 is rotated in a first direction, causing movement of belt 176 and rotation of second disc 174 in the same direction. Lead screw 164 is operatively connected to disc 174 so that rotation of disc 174 causes rotation of lead screw 164 in the same direction. A tensioner 178 like tensioner 158 can be provided to apply tension to the belt 176. The drive mechanism 162, like drive mechanism 40 of FIG. 3A, includes a first output flag or yoke 166 with slot 163 configured to engage a staple firing rod 46 in the same manner as flag 42. Rotation of the motor shaft generates rotational motion of the lead screw 164 through the drive belt, causing the drive mechanism 162 to move in linear motion along the lead screw 164 to effect linear movement of the firing rod 46 which advances the staple driving mechanism to advance (fire) the staples out from jaw 8b through tissue and into contact with the anvil in jaw 8a.

The belt drive 160 differs from belt drive 140 of FIG. 24A in that second disc 174 which is operatively connected to lead screw 164 is larger in diameter than first disc 172. Consequently, instead of providing a one to one ratio of the discs as in discs 154 and 152 of FIG. 24A, a greater ratio of disc 174 to disc 172 is provided which varies the output of motor 168. That is, the rotational output of lead screw 164 is less than the rotational output of the motor shaft due to the differing degree of rotation of discs 174, 178 due to the varying sizes. In all other respects, mechanism 160 is identical to mechanism 140.

FIGS. 26A-26D illustrate an alternate embodiment of a belt drive mechanism. Belt drive mechanism (assembly) 180 is identical to belt drive 140 of FIG. 24A except for the configuration of the drive belt and discs. That is, assembly 180 has a motor 188 connected to a planetary gear box 190 configured to gear down the output of the motor 188. The planetary gear box 190 drives a lead screw 184 through the belt drive operatively connected to the motor shaft. Upon rotation of the motor shaft by motor 188, first disc (wheel or pulley) 192 is rotated in a first direction, causing movement of belt 196 and rotation of second disc (wheel or pulley) 194. Lead screw 184 is operatively connected to disc 194 so that rotation of disc 194 causes rotation of lead screw 184 in the same direction. A tensioner 198 like tensioner 158 can be provided to apply tension to the belt 196. The drive mechanism 182, like drive mechanism 140 of FIG. 3A, includes a first output flag or yoke 186 with slot 183 configured to engage a staple firing rod 46 in the same manner as flag 42. Rotation of the motor shaft generates rotational motion of the lead screw 184 through the drive belt, causing the drive mechanism 182 to move in linear motion along the lead screw 184 to effect linear movement of the firing rod 46 which advances the staple driving mechanism to advance (fire) the staples out from jaw 8b through tissue and into contact with the anvil in jaw 8a.

The belt drive 180 differs from belt drive 140 of FIG. 24A in that discs 192, 194 have teeth to engage ribs or treads on belt 196. As shown, the toothed discs 192, 194 are spaced apart so their teeth/projections do not intermesh—the teeth of disc 192 engage belt 196 and the teeth of disc 194 engage belt 196. Rotation of disc 192 moves drive belt 194 in the same direction due to its engagement with the teeth, which causes rotation of toothed disc 194 in the same direction due to engagement with its teeth to rotate lead screw 184. In all other respects, mechanism 180 is identical to mechanism 140.

FIGS. 27A-27E illustrate an alternate embodiment of a belt drive mechanism. Belt drive mechanism (assembly) 200 is identical to belt drive 180 except for the different sized discs. That is, assembly 200 has a motor 208 connected to a planetary gear box 210 configured to gear down the output of the motor 208. The planetary gear box 210 drives a lead screw 204 through the belt drive operatively connected to the motor shaft. Upon rotation of the motor shaft by motor 208, first disc (wheel or pulley) 212 is rotated in a first direction, causing movement of belt 216 and rotation of second disc (wheel or pulley) 214. Lead screw 204 is operatively connected to disc 214 so that rotation of disc 214 causes rotation of lead screw 204 in the same direction. A tensioner 218 like tensioner 198 can be provided to apply tension to the belt 216. The drive mechanism 202, like drive mechanism 140 of FIG. 3A, includes a first output flag or yoke 206 with slot 203 configured to engage a staple firing rod 46 in the same manner as flag 42. Rotation of the motor shaft generates rotational motion of the lead screw 204 through the drive belt, causing the drive mechanism 202 to move in linear motion along the lead screw 204 to effect linear movement of the firing rod 46 which advances the staple driving mechanism to advance (fire) the staples out from jaw 8b through tissue and into contact with the anvil in jaw 8a.

The belt drive 200 differs from belt drive 180 of FIG. 24A in that second toothed disc 214 which is operatively connected to lead screw 204 is larger in diameter than first toothed disc 172. Consequently, instead of providing a one to one ratio of the discs as in discs 194 and 192, a greater ratio of disc 214 to disc 212 is provided which varies the output of motor 208. That is, the rotational output of lead screw 204 is less than the rotational output of the motor shaft due to the differing degree of rotation of discs 214, 212 due to the varying sizes. In all other respects, mechanism 200 is identical to mechanism 180.

It should be appreciated that the foregoing belt drive mechanisms can be used as an alternative to the gear mechanism in power pack 18 as well as an alternative to one or both of the gear mechanisms of power pack 90 discussed below.

In the foregoing embodiments, the power pack 18 was described for powering staple firing. In an alternate embodiment, the power pack can include a drive mechanism for effecting articulation. This motor powered articulation can be in addition to the motor powered staple firing, or alternatively, the power pack can be used solely for powered articulation. The embodiment of FIGS. 14A-23B illustrate a surgical stapler and power pack which powers both staple firing and articulation. If only for articulation, the power pack described below (power pack 90) would not include the gear mechanism engageable with the firing rod 46 for staple firing.

With initial reference to FIGS. 14A-14C, surgical stapler 61 is identical to surgical stapler 1 of FIG. 1A except for the power pack mounted in the stapler 61 and the articulation rod in the stapler 61 which is engaged by the power pack. Thus, like stapler 1, stapler 61 has a handle assembly 63, an endoscopic portion 66 extending distally therefrom and a pair of jaws 68a, 68b, (collectively "jaws 68") with at least one of the jaws movable relative to the other jaw, e.g., jaw 68b containing the staples (fasteners) movable toward stationary jaw 68a containing the anvil pockets. Handle 72 like handle 14 of stapler 1 is pivotable toward stationary handle 70 to approximate jaws 68a, 68b to clamp tissue between the closed jaws 68a, 68b. Handle assembly 63 includes a housing 64 and cover 62 which is identical to cover 22 of stapler 1, i.e., pivotably mounted to the housing 64 to move from a closed to an open position for top loading (or alternatively other directional loading) a power pack into the compartment within the housing 64. The compartment, like compartment 25 described above, retains the power pack and can include guiding structure for alignment of the power pack similar to guiding structure 23 described above to receive guides 90a, 90b of power pack 90. Stapler 61 also includes a rotation knob 74 which functions in the same manner as rotation knob 12 of stapler 1 described above to rotate tubular portion (shaft) 66. The jaw assembly, i.e., jaws 68a, 68b, articulate about joint 69 to move the jaws 68a, 68b to angular positions with respect to the longitudinal axis of stapler 61.

The power pack in the embodiment of FIGS. 14A-23B is designated by reference numeral 90 and has a motor assembly and drive mechanism for firing staples which is identical to that of the power pack 18 of FIG. 3A. However, power pack 90 differs from power pack 18 in that it additionally has a motor assembly and drive mechanism for articulating the jaws. The addition of the articulation assembly can be appreciated by a comparison of the cross-sectional view of FIG. 4H, which only effects firing of the fasteners (staplers), and the cross-sectional view of FIG. 15F which effects firing of fasteners and articulation of the jaw assembly.

More specifically, with reference to FIGS. 15A-15F and 18B, the powered staple firing assembly like the firing assembly of power pack 18 of FIG. 4H, includes a motor 83 connected to a planetary gear box 85 configured to gear down the output of the motor in the same manner as motor 32 and gear box 34 of power pack 18. The planetary gear box 85 drives a lead screw 86 through one or more gears operatively connected to the motor shaft. More specifically, upon rotation of the motor shaft by the motor 83 in a first direction, gear 81 is rotated in the same first direction, causing rotation of the gear 84 in a second opposite direction due to the intermeshed teeth of gears 81 and 84. Lead screw 86 is operatively connected to gear 84 so that rotation of gear 84 causes rotation of lead screw 86 in the same direction. The power pack 18 includes a battery 33 which can be rechargeable outside the stapler when the power pack 18 is removed. The power pack 90 in some embodiments can include a power switch which is activated, i.e., turned on, by the clinician to start the motor and effect staple firing. In other embodiments, the motor can automatically turn on when fully loaded or upon actuation of another control on the stapler housing 4.

Connected to the end of lead screw 86 (the end opposite the connection to the gear 84) is a drive mechanism 80 which is configured to move in a linear motion (in an axial direction) along the lead screw 86 in response to rotation of the lead screw 86. Drive mechanism 80 includes a flag or yoke 82 identical to yoke 42 of power pack 18 discussed above, which engages flange or boss 76 of firing rod 75 within housing 64 of stapler 61. The connection of the flag 82 to the firing rod 75, the motor and gear mechanism, and the drive mechanism 80 of power pack 90 are the same as the power pack 18 and therefore the aforedescribed functions and features/components of power pack 18 for staple firing are fully applicable to the function and features/components of power pack 90 for staple firing so for brevity are not fully repeated herein. It should also be appreciated that the alternative mechanisms for motor powered stapled firing, such as the various belt drive mechanisms discussed above and/or illustrated in the Figures, can also be used in the power pack 90 to effect staple firing. Additionally, the various sensors discussed above with regard to sensing the firing stroke can also be provided in power pack 90 for the same uses.

Power pack 90 also has an articulation assembly, shown in detail in FIGS. 22A-22D. The articulation assembly includes a powering assembly including a motor 96 connected to a planetary gear box 93 configured to gear down the output of the motor 96. The planetary gear box 93 drives a lead screw 98 through gears 91, 92 operatively connected to the motor shaft. More specifically, upon rotation of the motor shaft by motor 96 in a first direction, gear 91 is rotated in the same first direction, causing rotation of the gear 92 in a second opposite direction due to the intermeshed teeth of gears 92 and 91. Lead screw 98 is operatively connected to gear 92 so that rotation of gear 92 causes rotation of lead screw 98 in the same direction. The power pack 90 in some embodiments can include a power switch which is activated, i.e., turned on, by the clinician to start the motor and effect articulation.

Connected to the end of lead screw 98 (the end opposite the connection to the gear 92) is a drive mechanism 95 configured to move in a linear motion (in an axial direction) along the lead screw 98 in response to rotation of the lead screw 98. For example, the drive mechanism 95, like drive mechanisms 40 and 80 described above, may include internal threads that engage external threads of the lead screw 98 and may include slides engaged in a track that prevent the drive mechanism 95 from rotating and therefore cause the drive mechanism 95 to move linearly (axially) in response to rotation of the lead screw 98. As depicted, the power pack 90 has a compact configuration as the lead screw 98 extends alongside, slightly spaced from, the motor 96 and gear box 93, i.e., both the motor 96/gear box 93 and lead screw 98 extending longitudinally with the lead screw 98 parallel to the motor 96. The drive mechanism 95 is connected to a proximal end of lead screw 98. The drive mechanism 95 has an articulation rod engagement feature in the form of a flange or yoke 94 extending therefrom having legs 99a and a recess 99b to engage an articulation rod 79 within the housing 63. In the illustrated embodiment (see e.g., FIGS. 15B and 22C), the articulation rod 79 includes a flange 78 which is engageable by the flag 94. The output flag 94 can engage the bossed end 78 of the articulation tube 79 in substantially the same manner as the output flag 42 engages the bossed end 44 of the firing rod 46 as discussed above.

The articulation assembly of the power pack 90 is oriented in the opposite direction from the staple firing assembly to minimize the space required in the power pack 90, thereby providing the power pack with a compact configuration. As can be appreciated by reference to FIGS. 15A and 15F, the drive assembly 80 and associated flag 82 are at a proximal end of the assembly for firing staples with the lead screw 86 extending distally toward the gears 81, 84. The driving assembly 95 with associated flag 94 of the assembly for articulation are at a distal end with the lead screw 98 extending proximally toward gears 91, 92. Also as can be appreciated by reference to the orientation of FIGS. 15A and 15F, the articulation assembly is above (closer to the cover 22) than the firing assembly, and the articulation assembly in the illustrated embodiment is positioned axially proximal of gears 81, 84 and axially distal of drive mechanism 80, radially spaced from lead screw 86.

The power pack 90, like power pack 18 can have features/structure to constrain the motors 84 and 96. In the embodiment of FIG. 15D, such feature is in the form of proximal rails 97a and distal rails 97b spaced apart axially within the housing of the power pack 90. Gear box 93 is seated within proximal rails 97a and motor 96 is seated within distal rails 97b, the rails 97a, 97b retaining the motor and preventing axial and rotational movement within the housing of power pack 90. Bearing or bushings 98a, 98b can also be provided to constrain the lead screw 98 at opposing ends, while allowing rotation thereof, thereby also constraining the motor. Other features can additionally or alternatively be provided to restrain the motor from axial movement while allowing rotation of the lead screw.

The power pack 90 can include guides, e.g., projections 90*a*, 90*b*, either axially aligned or axially offset, similar to guides 28 of power pack 18 for alignment with guiding structure in the compartment of stapler 61.

In use, with the cover 62 of stapler 61 in the open position, power pack 90 is loaded into the compartment of the handle housing 63. The cover 62 is closed to seal the power pack 90 from contaminants in same manner as cover 22 of stapler 1. Upon loading of the power pack 90, flag 82 of the drive mechanism 80 of the staple firing assembly engages flange 76 of firing rod 75 and flag 94 of drive mechanism 95 of the articulation assembly engages flange or bossed end 78 of articulation rod 79. Actuation of the motor 96 effects linear motion of the flag 94 which moves the articulation rod 79 linearly (axially). The articulation rod 79 is either directly coupled to the joint 69, or coupled to another member or multiple members which are coupled to the joint 69. When moved linearly, the articulation rod 79 effects movement of the jaws 68A, 68*b* of the stapler 61 to angular positions with respect to the longitudinal axis of the stapler 61. Note the articulation drive assembly operates in a similar manner as the firing drive assembly of power pack 18 in that when the power pack 90 is secured to the tube 79 by the second output flag 94, linear motion generated at the second output flag 94 is transferred to linear motion of the tube 79.

Actuation of the motor 83 effects linear motion of the flag 82 which moves the firing rod 75 linearly (axially). The firing rod 75 either extends through the elongated portion 66 for engagement of the firing mechanism in the jaw 68*b* or is coupled to another elongated component(s) extending through the endoscopic portion 66 to engage the firing mechanism in the jaw 68*b*. Note that the articulation rod or tube 79 can be configured to receive the firing rod 75 so that the firing rod 75 can move within the tube 79 to effect firing and the articulation rod 79 can slide linearly over the firing rod to effect articulation.

After use, the cover 62 can be opened and the power pack 90 removed and charged while the handle assembly 63 (and stapler 61) is sterilized or disposed of if the stapler is a disposable instrument. The power pack 90, like power pack 18 described above, may be reused without requiring sterilization by being inserted into the receptacle of the now-sterilized handle assembly 63 or a different sterile handle assembly. Thus, the removable power pack 90, like power pack 18, does not need to be subjected to the sterilization process and, therefore, contact between the harsh temperatures and/or chemicals of the sterilization process is advantageously avoided.

One or more seals are utilized for sealing power pack 18 and power pack 90 within the handle assembly 2 or 63 so that the power pack remains sterile and is not exposed to bodily fluids during surgical procedures. For example, as discussed above, in the stapler 1 of FIG. 1, the top seal 24 is positioned at the interface between the cover 22 and the housing 4 of the handle assembly 2 where the cover 22 closes for sealing the opening into the receptacle 20 and, therefore, power pack 18 from the environment when positioned therein. Similarly, in the stapler 61 of FIG. 14A, the top seal is positioned at the interface between the cover 62 and the housing 64 of the handle assembly 63 wherein the cover 62 closes for sealing the opening into the receptacle 20 and, therefore, power pack 90 from the environment when positioned therein. As shown in FIGS. 21A-21C, further seals can be provided to further seal the receptacle and thus the power pack. An O-ring 56 is placed around the articulation rod 79 to seal the space around the rod 79. A flexible trigger seal 58 surrounds the lever 72 for sealing the internal components of the handle assembly 63 throughout the range of positions of the movable lever 72. Thus, all of the openings into the receptacle of the handle assembly 63 are sealed from the external environment. The O-ring seal 56 and trigger seal 58 can also be used in stapler 1 so the openings into the receptacle 20 of handle assembly 2 are sealed from the external environment. Elastomeric seal 59*a* seals cover 62 from U-channel 59 within the handle which supports the power pack 90. Additional seals can be provided to prevent flow of body fluid through the endoscopic portion 66 (and endoscopic portion 6). Other types of seals and seals in different locations are also contemplated.

FIGS. 54A-73 illustrate an alternate embodiment of the power pack. The power pack is shown loaded into surgical stapler 700. Surgical stapler 700 differs from the surgical stapler 1 of FIG. 1A in the power pack mounted in the stapler and the components interacting with the power pack for achieving powered fastener firing and powered articulation as described below. Like stapler 1, stapler 700 has a handle assembly 702, an endoscopic portion (tubular shaft) 704 extending distally therefrom and a pair of jaws 706, 708 with at least one of the jaws movable relative to the other jaw, e.g., jaw 708 containing the staples (fasteners) movable toward stationary jaw 706 containing the anvil pockets on fastener forming surface 706*a*. Handle 710 like handle 14 of stapler 1 is pivotable toward stationary handle 712 to approximate jaws 706, 708 to clamp tissue between the closed jaws 706, 708. Handle assembly 702 includes a housing 714 and cover 718 which like cover 22 of stapler 1 is pivotably mounted to the housing 714 to move from a closed position to an open position for top loading (or alternatively other directional loading) a power pack into the compartment 716 within the housing 714 and sealing the compartment 716. The compartment 716, like compartment 25 described above, retains the power pack and can include guiding structure for alignment of the power pack similar to guiding structure 23 described above to receive guides of the power pack. A latch 721 releasably secures the cover 718 in a closed position. Stapler 700 also includes a rotation knob 720 which functions in the same manner as rotation knob 12 of stapler 1 described above to rotate tubular portion (shaft) 704 about its longitudinal axis. The jaw assembly, i.e., jaws 706, 708, articulate about joint 704*a* to move the jaws 706, 708 to angular positions with respect to the longitudinal axis of stapler 700.

The power pack in the embodiment of FIGS. 54A-73 is designated by reference numeral 730 and has a motor assembly and drive mechanism for firing staples and a motor assembly and drive mechanism for articulation of the jaw assembly. The power pack 730 can have a non-removable battery pack or alternatively a removable battery pack in accordance with the alternate embodiments disclosed herein.

The power pack 730, as shown in FIGS. 58A and 58B has a left side cover 734 with inwardly extending tabs 734*a* and a right side cover 732 with notches 732*a* to receive tabs 734*a* to connect the two covers 734, 732 in forming a sealed enclosure of the power pack 730. Note the terms "left" and "right" used herein refer to the sides as viewed from the proximal end of the instrument looking toward the distal end. The terms "upper" and "lower" refer to the orientation of the instrument in FIG. 54A.

The housing 730 further includes a proximal plate 742 and a distal plate 744 positioned respectively at the proximal and distal regions of housing 730. Right chassis 736 has openings in arms 733 to receive screws for mounting to distal plate 744. Left chassis 738 has a recess to receive bearing trap 774 as described below.

The three bosses on the proximal face of distal plate 744 fit in counterbores 746a on the distal face of the distal right chassis 746. The bosses on the distal face of proximal plate 742 fit into a) the opening 738a in left chassis 738; and b) the two openings 736a (top and bottom) in right chassis 736. The boss on the bottom right distal side of plate 744 mates with the opening in the distal end of left chassis 738. The control board base 740, which adds rigidity and can provide a support for the PC board (not shown), has a boss received in a bore in distal right chassis 746 and at the other end a boss received in opening 738a of left chassis 738. Left chassis 738 includes a motor pincher for constraining the articulation motor as described below. A screen 784 (FIG. 64) can provide indicators for various conditions of the firing, articulation and/or clamping of the instrument.

The power pack 730 includes a battery which can be rechargeable outside the stapler when the power pack is removed. The battery can be interchangeable as described herein. The power pack 730 in some embodiments can include a power switch which is activated, i.e., turned on, by the clinician to start the motor and effect staple firing. In other embodiments, the motor can automatically turn on when fully loaded or upon actuation of another control on the stapler housing.

Turning now to the deployment mechanism for staple firing and the articulation mechanism for jaw articulation within the power pack 730, the present invention provides a system to keep these mechanisms on center. As explained in more detail below, the collars deliver force directly on center, pushing articulation and deployment (firing) on axis. The moment arm is eliminated which reduces friction for less resistance. Note the reactive forces are also on axis. Thus, the mechanisms are mounted/supported within the power pack 730 to prevent off axis movement, i.e., prevent distortion along the axis. This increases the efficiency of the system. That is, the reduced friction via the supports, alignments and mounts discussed herein, less power (motor and battery) can be utilized along with a smaller powertrain/power pack.

Turning first to the deployment mechanism for staple firing, and with reference to FIGS. 59A-59D and 70, the powered staple firing assembly like the firing assembly of power pack 18 of FIG. 4H, includes a motor 748 connected to a planetary gear box configured to gear down the output of the motor in the same manner as motor 32 and gear box 34 of power pack 18. The motor drives a ball screw 754 through a pulley system. Lead screw 754 extends from nut 755. Collar 756 of the drive mechanism has an opening to receive the nut 755 for attachment thereto. The opening in the collar 756 has a female thread engageable with the male thread of the deployment nut 755. The collar 756 is threaded over the nut 755 and screwed tight thereto. Set screw 781, extending through pinch slot 759 (FIG. 72), constrains collar 756 to nut 755 (about its circumference) when compressed.

Thrust (axial) bearings and radial bearings on opposing ends of the screw 754 provide centering and axial alignment of the screw 754 during use. Thrust bearing 768 is mounted on the distal end of screw 754 and thrust bearing 780 is mounted at the proximal end of the screw 755, proximal of collar 756, to resist any axial force applied to the rotating screw 755 and maintain its axial position. Radial bearings 757, 782 are provided to resist radial loads (forces that are perpendicular to the direction of the screw) and are located on the respective distal and proximal ends of the screw 755 with radial bearing 757 distal of thrust bearing 768 and radial bearing 782 proximal of thrust bearing 780. The thrust bearings 768 and 780 are slip fit over the outer diameter of the deployment screw 754 (FIG. 64), at distal and proximal ends, respectively, and thus float relative to the screw 754. They are sandwiched together with the chassis. The radial bearings 757 and 782 are press fit into openings 744a and 742a of distal plate 744 and proximal plate 742, respectively (see FIGS. 58B and 64). The radial bearing 764 for the deployment motor 748 is press fit into opening 744b in the distal plate 744. The deployment screw 754 has a reduced diameter portion at the proximal and distal ends to form a shoulder 754a and 754b at the larger dimeter portions which abut, i.e., contact, thrust bearings 780, 768. Thus, the thrust bearings 768, 780 can rotate freely within the housing, but are constrained by the steps (shoulders) of the ball screw 754 so they cannot move along the axis of the screw.

Collar 756 has mounted thereto a pair of left track bearings 779 and a pair of right track bearings 778 which travel along tracks 760, 762, thereby preventing rotation out of the track as forces are translated linearly along shaft as the nut 755 translates forward and backward. The tracks 760, 762 can be attached to or integrated (monolithic) with the chassis. Collar 756 includes a blade/tab 756b extending inwardly from wall 756a which engages a circumferential recess (groove) in the deployment disk 726 of the stapler which is attached to (or extends from) the firing rod of the stapler. In this manner, axial movement of collar 756 (via ball screw 754 when actuated by the motor) moves the deployment disk 726 axially, the collar traveling along the respective left and right tracks (runners) 760, 762 via respective left and right bearings 779, 778 trapped within the C-channels of the tracks 760, 762.

Upon rotation of the motor shaft by the deployment motor 748 in a first direction, belt drive and pulley 766a and 766b (collectively pulleys 766) cause rotation of ball screw 754. This can be appreciated by reference to FIGS. 62 and 70. Pulley 766a is attached to the motor shaft of firing (deployment) motor 748 and pulley 766b is attached to the ball screw 754. As shown in FIG. 62, the deployment screw 754 can be notched or have another type of irregular surface to mate with the pulley 766a. As shown, three screws 783 mount the deployment motor 748. The screws 783 are mounted within slots to adjust the position of the deployment motor 748 to adjust the tension on the belt 763. In the position shown, i.e., at the bottom of the slots, the belt tension is less. During manufacture, if it is desired to increase the tension on belt 763, the screws 783 are positioned 748 further up in the slots to move the motor further up, thus lengthening the belt 763 and increasing the tension on the belt 763. When the motor shaft rotates, the belt 763 effects rotation of the other pulley 766a to cause rotation of the ball screw 754 to move the nut 755 and deployment (firing) collar 756 axially. As shown in FIG. 70, the ball screw 754 and motor 748 are radially displaced to conserve space.

The collar 756 is connected to the end of ball screw 754 and is configured to move in a linear motion (in an axial direction) in response to rotation of the ball screw 754. The collar 756 forms part of the drive mechanism 80 and includes a flag or yoke similar to yoke 42 of power pack 18 discussed above, however, it is different in that it has a tab or blade 756b which engages a recess in a deployment disk 726 of firing rod 722 of stapler 700. Blade 756b can extend around 180 degrees as shown for example in FIG. 59D. A pinch slot 759 (FIG. 72) constrains the collar 756 to the deployment nut 755. The firing rod 722 extends proximally within housing 714 of stapler 700 for receiving the drive (deployment) mechanism, i.e., blade 754*b* of collar 754, of the power pack 730. It should also be appreciated that the alternative mechanisms for motor powered stapled firing, discussed herein and/or illustrated in the Figures, can also be used in the power pack 730 to effect staple firing. Additionally, the various sensors discussed herein with regard to sensing the firing stroke can also be provided in power pack 730 for the same uses.

As depicted, the power pack 730 has a compact configuration as the ball screw 754 extends alongside, slightly spaced from, the motor 748, i.e., both the motor 748 and ball screw 754 extending longitudinally with the ball screw 754 parallel to the motor 748.

Turning now to the articulation assembly of the power pack 730, and with reference to FIGS. 60A-60D and 70, the powered articulation assembly includes a motor 750 connected to a planetary gear box configured to gear down the output of the motor 750. The motor 750 drives an articulation ball screw 752 operatively connected to the motor output shaft 751. As shown, the articulation screw 752 and motor 750 are axially aligned, e.g., the screw 752 extends distally from the motor 750 and motor shaft 751. The output shaft 751 of motor 750 fits into cavity (slot) 752*a* bored into the proximal end of screw 752 to capture the shaft 751 as shown in FIG. 66. Rotation of the motor shaft 751 by motor 750 in a first direction, causes rotation of ball screw 752 in the same direction. The motor shaft 751 can have a flat 751*a* (FIG. 67B) keyed within the D-slot of screw 752 for engaging and rotating the articulation screw 752. Motor pincher 795 (FIG. 69), encircling the articulation motor 750, has a slot 795*b* to allow the pincher 795 to compress about the circumference of the articulation motor 750 as set screw 795*a* is tightened within opening 738*b* (FIG. 58B) to constrain the articulation motor 750. Note the screw 795*a* extends through the opening in the bearing trap 774 which is seated within left chassis 738. (The bearing trap 774 is constrained to the left chassis 738 and bearing race 760, 762 by the screw 795*a*). The power pack 730 in some embodiments can include a power switch which is activated, i.e., turned on, by the clinician to start the motor and effect articulation. In alternate embodiments, instead of pincher, the motor can be restrained by a face mount via a set of screws in a similar manner to the mounting of the deployment motor 748 by screws 783.

With reference to FIGS. 60A, 60B, and 70, connected to the end of articulation screw 752 (the end opposite the connection to the motor 750) is a collar 753 of the drive mechanism configured to move in a linear motion (in an axial direction) in response to rotation of the articulation ball screw 752. The shoulder screw 794 extending through opening 794*a* constrains the collar 753 on the ball screw nut 786. The collar 753 is radially offset from the screw 752. Spacer 791 is positioned between the nut 786 and collar 753. The collar 753 forms part of the articulation drive mechanism, is connected to a proximal end of ball screw 752, and has an articulation rod engagement feature in the form of a flag or yoke (as in the foregoing embodiments) having an articulation blade 753*b* or tab engaging a recess in the articulation disk 725 of articulation rod 723. Blade 753*b* can extend around 180 degrees as shown for example in FIG. 60B. The articulation rod 723 can be pinned to the articulation disk or attached in other ways. The articulation rod 723 is attached at a distal end to the jaw assembly (jaws 706, 708) to effect articulation as it translates (in the manner to effect articulation as described in the embodiments above).

The articulation assembly of the power pack 730 is oriented in the opposite direction from the staple firing assembly to minimize the space required in the power pack 730, thereby providing the power pack with a compact configuration. As can be appreciated by reference to FIG. 70, the collar (blade) 756 of the staple drive assembly engageable with the staple firing rod is at a proximal end of the assembly for firing staples with the screw 754 extending distally and the pulley system at the distal end. The collar 753 of the articulation drive assembly for engagement with the articulation rod for articulation is at a distal end with the ball screw 752 extending proximally with respect to collar 753. Also as can be appreciated by reference to the orientation of FIG. 70, the articulation collar 753 and deployment collar 756 are longitudinally spaced and axially aligned. Collar 753 has an opening 753*a* for passage of articulation screw 754 to conserve space.

Thrust (axial) bearings and radial bearings on opposing ends of the screw 786 provide centering of the screw 752 during use. With reference to FIGS. 60A-60D, thrust bearing 770 is mounted on the distal end of articulation screw 752 and thrust bearing 790 is mounted at the proximal end of the articulation screw 752, proximal of collar 753, to resist any axial force applied to the rotating screw 752 and maintain its position. Radial bearings 772, 792 to resist radial loads (forces that are perpendicular to the direction of the screw) are provided on the respective distal and proximal ends of the screw 752 with radial bearing 772 distal of thrust bearing 770 and radial bearing 792 proximal of thrust bearing 790. Bearings 790 and 792 are seated within bearing trap 774 which is positioned in left chassis 738 as described above. The radial bearings 792 are press fit in the bearing trap 774. The thrust bearing 770 is slip fit over the screw 752 and is also seated within bearing trap 774 (see FIG. 66). At the other end, thrust bearing 770 is slip fit over articulation screw 752 and radial bearing 772 is press fit within opening 744*b* in distal plate 744 (FIGS. 58B and 66). The screw 752 floats relative to the assembly and is kept in place by the retention shoulders 799*a*, 799*b* at proximal and distal ends formed by the reduced diameter portion at the proximal and distal ends to form an abutting (mating), i.e., contacting, surface with the larger diameter thrust bearing 790, 770, respectively. Thus, the thrust bearings 770, 772 can rotate freely within the housing, but are constrained by the steps (shoulders) of the articulation screw 752 so they cannot move along the axis of the shaft.

Collar 753 has mounted thereto a pair of left track bearings 759 and a pair of right track bearings 758 which travel along tracks 760, 762, thereby preventing rotation out of track as forces are translated linearly along shaft as the nut 786 translates forward and backward. As noted above, the tracks 760, 762 can be attached to or integrated (monolithic) with the chassis. Collar 753 includes a blade/tab extending inwardly from wall 756*a* which engages a circumferential recess (groove) in the disk 725 of the articulation rod 723. In this manner, axial movement of collar 753 moves the articulation disk 725 axially, the collar 753 traveling along left and right tracks (runners) 760, 762 via bearings 759, 758 as the collar 753 is moved axially.

Use of the stapler will now be described in conjunction with stapler 61, however, stapler 700 would be used in a similar manner. In use, with the cover 62 of stapler 61 in the open position, power pack 90 is loaded into the compartment of the handle housing 63. The cover 62 is closed to seal the power pack 90 from contaminants in same manner as cover 22 of stapler 1. Upon loading of the power pack 90, flag 82 of the drive mechanism 80 of the staple firing assembly engages flange 76 of firing rod 75 and flag 94 of drive mechanism 95 of the articulation assembly engages flange or bossed end 78 of articulation rod 79. Actuation of the motor 96 effects linear motion of the flag 94 which moves the articulation rod 79 linearly (axially). The articulation rod 79 is either directly coupled to the joint 69, or coupled to another member or multiple members which are coupled to the joint 69. When moved linearly, the articulation rod 79 effects movement of the jaws 68A, 68b of the stapler 61 to angular positions with respect to the longitudinal axis of the stapler 61. Note the articulation drive assembly operates in a similar manner as the firing drive assembly of power pack 18 in that when the power pack 90 is secured to the tube 79 by the second output flag 94, linear motion generated at the second output flag 94 is transferred to linear motion of the tube 79.

Actuation of the motor 83 effects linear motion of the flag 82 which moves the firing rod 75 linearly (axially). The firing rod 75 either extends through the elongated portion 66 for engagement of the firing mechanism in the jaw 68b or is coupled to another elongated component(s) extending through the endoscopic portion 66 to engage the firing mechanism in the jaw 68b. Note that the articulation rod or tube 79 can be configured to receive the firing rod 75 so that the firing rod 75 can move within the tube 79 to effect firing and the articulation rod 79 can slide linearly over the firing rod to effect articulation.

After use, the cover 62 can be opened and the power pack 90 removed and charged while the handle assembly 63 (and stapler 61) is sterilized or disposed of if the stapler is a disposable instrument. The power pack 90, like power pack 18 described above, may be reused without requiring sterilization by being inserted into the receptacle of the now-sterilized handle assembly 63 or a different sterile handle assembly. Thus, the removable power pack 90, like power pack 18, does not need to be subjected to the sterilization process and, therefore, contact between the harsh temperatures and/or chemicals of the sterilization process is advantageously avoided.

FIGS. 38A-53 illustrate an embodiment of the jaw clamping mechanism which can be used with any of the stapler embodiments disclosed herein. The jaw clamping mechanism includes a clamp pin 516 and cam pin slot 512. The clamp pin 516 extends completely through the width (diameter) of the instrument, i.e., from one side to the other, to add stability. Cartridge jaw 506, which contains a plurality of fasteners such as staples, pivots about pivot pin 514 between open and closed positions. Jaw assembly containing jaws 504 and 506 are articulatable (pivotable) with respect to outer tube 502 as the jaws 504, 506 pivot about articulation pin 510.

The cartridge jaw 506 is shown in the open position in FIGS. 38A-45, spaced from anvil 504, i.e., the cartridge received in cartridge receiving channel 508 is spaced from anvil forming surface 505 of anvil 504. The anvil forming surface 505 deforms the staples fired from the cartridge jaw 506. In the open (unclamped) position, the clamp pin 516 is at a distal end of clamp pin slot 512 as shown in FIG. 39. In this position shown in FIG. 42, the clamp rod 526 and the clamp laminates 528 are shown in the distal position. Clamp laminates 528 connect clamp rod 526 to the clamp adapter 530 via hook engagement of hook 528a at the distal end of clamp laminates 528 and hook 534 at the proximal end of the clamp adapter 530. The clamp laminates 528 can be fixedly attached to the clamp rod 526 and clamp adapter 530 or alternatively floatably attached to these components. The flexibility of the clamp laminates 528 allows for articulation of the jaws 504, 506.

Upon manual camping of the handle to effect closure of the cartridge jaw 506, the clamp rod 526, which is operatively connected to the handle, is pulled proximally, thereby pulling the attached clamp adapter 530 proximally. This moves the through pin 516, which is attached to clamp adapter 530, proximally within the cam slot 512 to the position of FIGS. 47 and 50 to move the cartridge jaw 506 toward the anvil jaw 504 to a clamped (closed) position as the cartridge jaw pivots 506 about pivot pin 514. The clamp pin 516 translates in the slot relative to the location of the clamp rod position. The cartridge jaw 506 rotates around the pivot pin 514 relative to the location of the clamp pin 516 in the cam slot 512.

The deployment laminates 522, 524 are connected at respective distal regions 522a, 522b to the I-beam 536 which is advanced for staple firing. The I-beam 536 and deployment laminates 522, 524 remain stationary during clamping of the jaws 504, 506.

FIGS. 35-37C illustrate alternate embodiments of the power pack having a removable battery pack. Each of the power packs (power trains) 406, 420 and 430 in the embodiments of FIGS. 35-37C can have a motor assembly and drive mechanism for firing staples which is identical to that of the power pack 18 of FIG. 3A or alternatively can have a motor and drive mechanism for firing staples and additionally a motor assembly and drive mechanism for articulating the jaws as in power pack 90 of FIG. 14A or power pack 730 of FIG. 54B described above. The surgical staplers for receiving power packs 406, 420, 430 are the same as the surgical stapler 1 (except for the compartment and cover) so that it has been labeled with like reference numerals. The power packs 406, 420 and 430 could also be used with the other surgical staplers described herein or with other surgical instruments such as those described herein. Therefore, further discussion of the surgical staplers is not provided herein as the description of the stapler 1 components (e.g., shaft 6, jaws 8a, 8b, handle 12, etc.) and its functions, as well the description of other staplers, are fully applicable to the stapler receiving power packs 406, 420 or 430.

Figure 35:
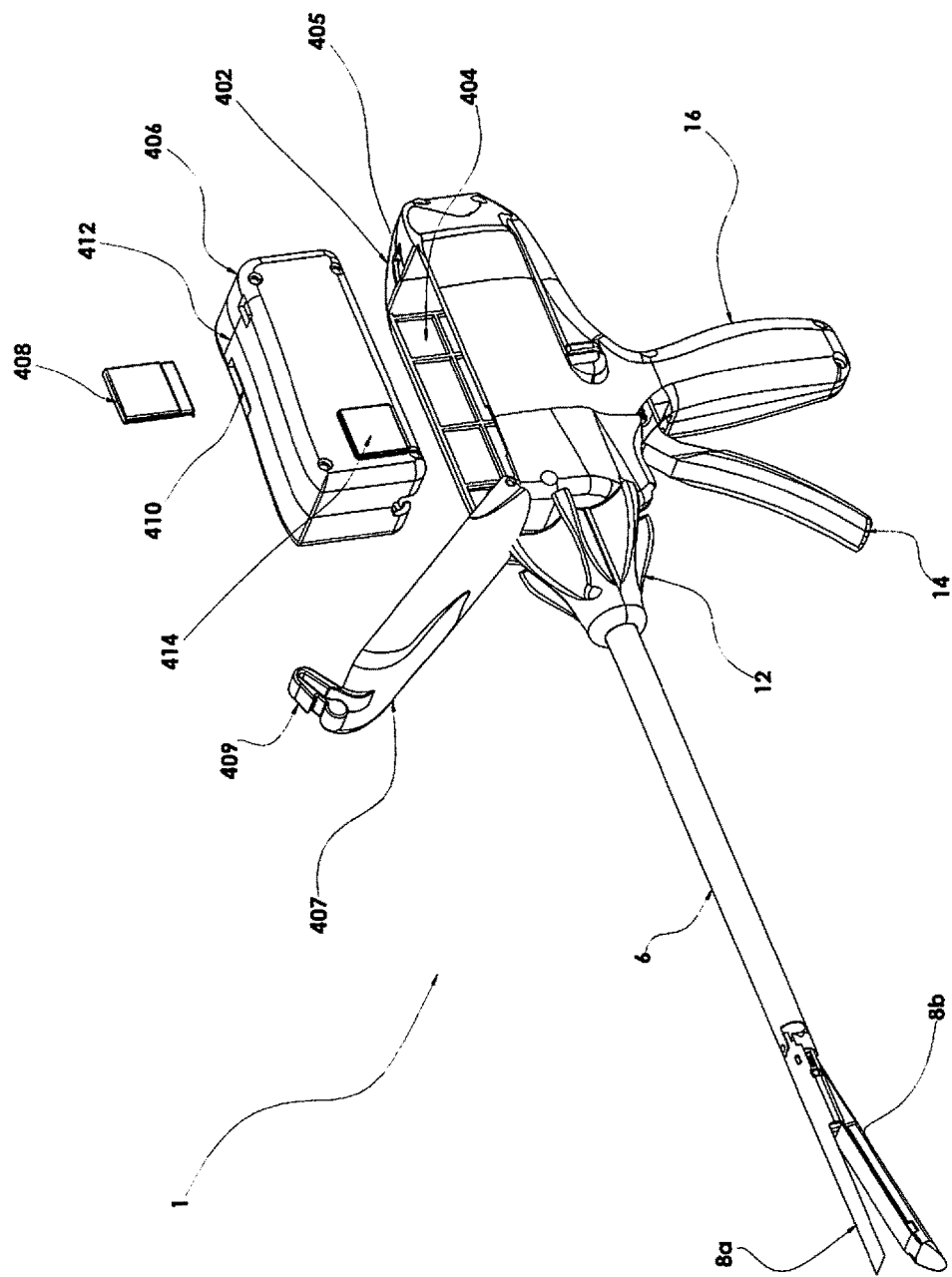
FIG. 35 is a perspective view of an alternate embodiment of the surgical instrument of the present invention having a replaceable battery pack.

Turning first to the embodiment of FIG. 35, the power pack 406 has an upper surface 412 having a cavity 410 to slidably receive card-like battery pack 408. Battery pack 408 is slid into the cavity and engages a contact within the housing to enable actuation of the motor to power the drive mechanism within the power pack 406 to effect staple firing and/or jaw articulation in the same manner as described above (via engagement by the flag or yoke). Power pack 406 is placed into the cavity 404 of housing 402 in a similar manner as described above, e.g., top loaded into the compartment, and the hinged cover 407 is closed to seal the power pack 406 from the external environment. Cover 407 differs from cover 22 in that it includes a spring loaded latch 409 received in latch cavity 405 of housing 402 to retain the cover 407 in the closed position. The latch 409 is released by pressing latch 409 to disengage the latch 409 so the cover 407 can be opened to access the power pack 406. Raised surface (tab) 414 on one or both sides of the power pack 406 aligns with a recess in the compartment 404 for alignment of the power pack 406 during insertion.

In use, the battery pack 408 can be aseptically preloaded in the power pack 406, either by a user or packaged with the battery pack 408 preloaded, and the power pack 406 is aseptically preloaded into the surgical instrument. During a surgical procedure, in the event of a battery failure, the cover 407 can be opened and the power pack 406 can be removed intraoperatively from compartment 404, the battery pack 408 removed from cavity 410, a new (second) charged battery (battery pack) aseptically placed in cavity 410 and the power pack 406 with the replacement battery pack reloaded into compartment 404. In an alternative use, during a surgical procedure, in the event of a battery failure, the cover 407 can be opened and with the power pack 406 remaining in compartment 404, the battery pack 408 is removed from cavity 410 of the power pack 406 and a new (second) charged replacement battery (battery pack) aseptically placed in cavity 410 while the power pack 406 remains loaded (positioned) within the compartment 404 of the surgical instrument.

Figure 36:
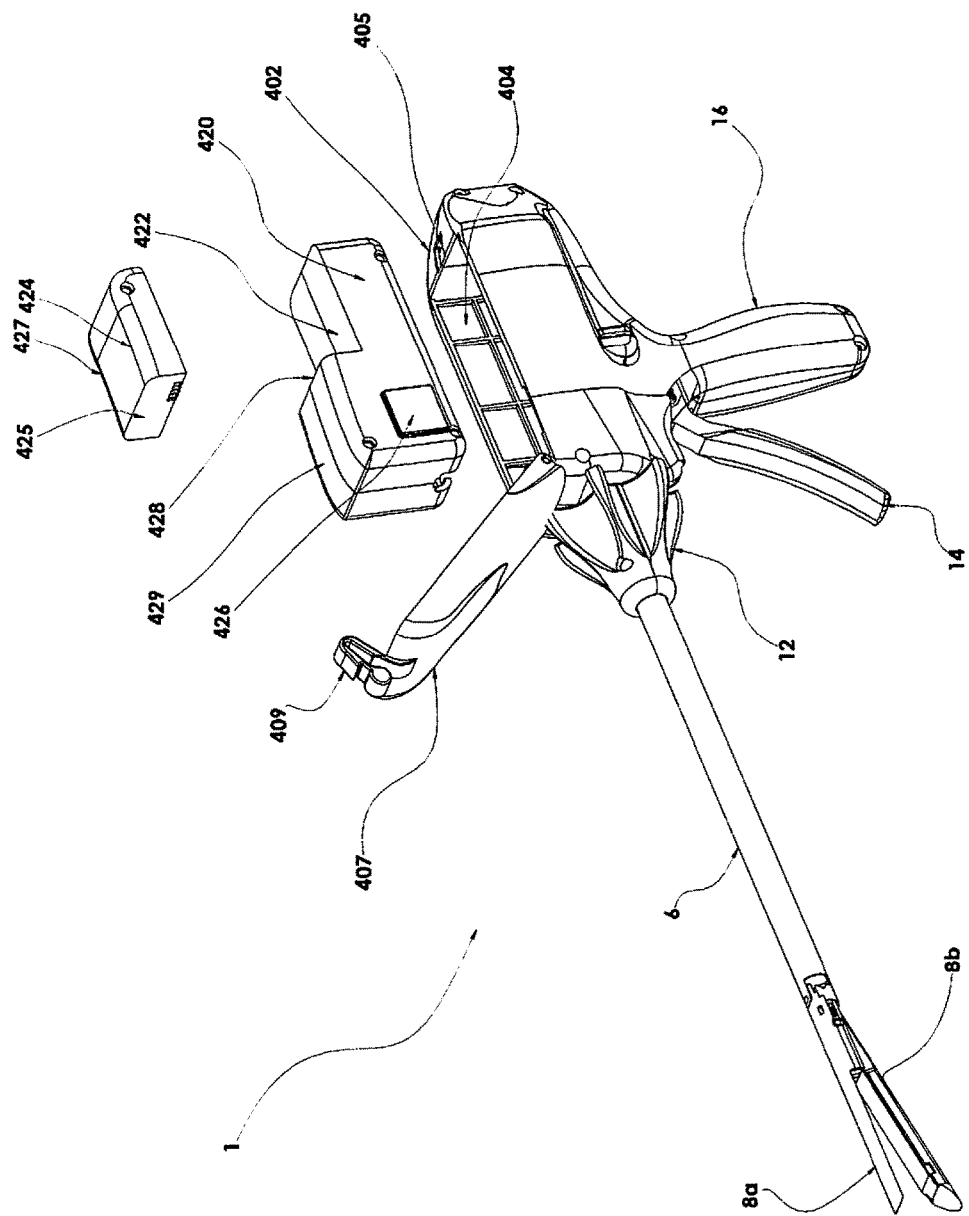
FIG. 36 is a perspective view similar to FIG. 35 illustrating an alternate embodiment of the replaceable battery pack of the present invention.

In the alternate embodiment of FIG. 36, the stapler 1 is the same as in FIG. 35, the difference being the power pack and battery pack. More specifically, power pack 420 has an outer upper surface 422 extending proximally from wall 428, on which the battery pack 424 is mounted. Wall 425 of battery pack 424 can be placed in abutment with wall 428, and the power pack 420 and battery pack 424 can be dimensioned so that the battery pack 424 becomes part of the outer contour of the power pack 420, e.g., the upper surface 427 of the power pack can be substantially flush with the upper surface 429 of the power pack 420, although in alternate embodiments the upper surface can be below or above the upper surface 429. Power pack 420 can have an alignment tab 426 on one or both sides to aid insertion/alignment. The battery pack can include an engagement feature interacting with the power pack/to secure the battery pack 424 on the power pack 420.

In use, as with power pack 406 described above, the battery pack 424 can be preloaded, i.e., pre-mounted, onto the power pack 420 (by the user or prepackaged) and can be removed and replaced with another (second) charged battery (battery pack) during a surgical procedure by first removing the power pack 420 from the compartment 404 of stapler 1 or alternatively the battery pack 424 can be removed from the power pack 420 and replaced by another charged battery pack while the power pack 420 remains in the compartment 404.

Figure 37A:
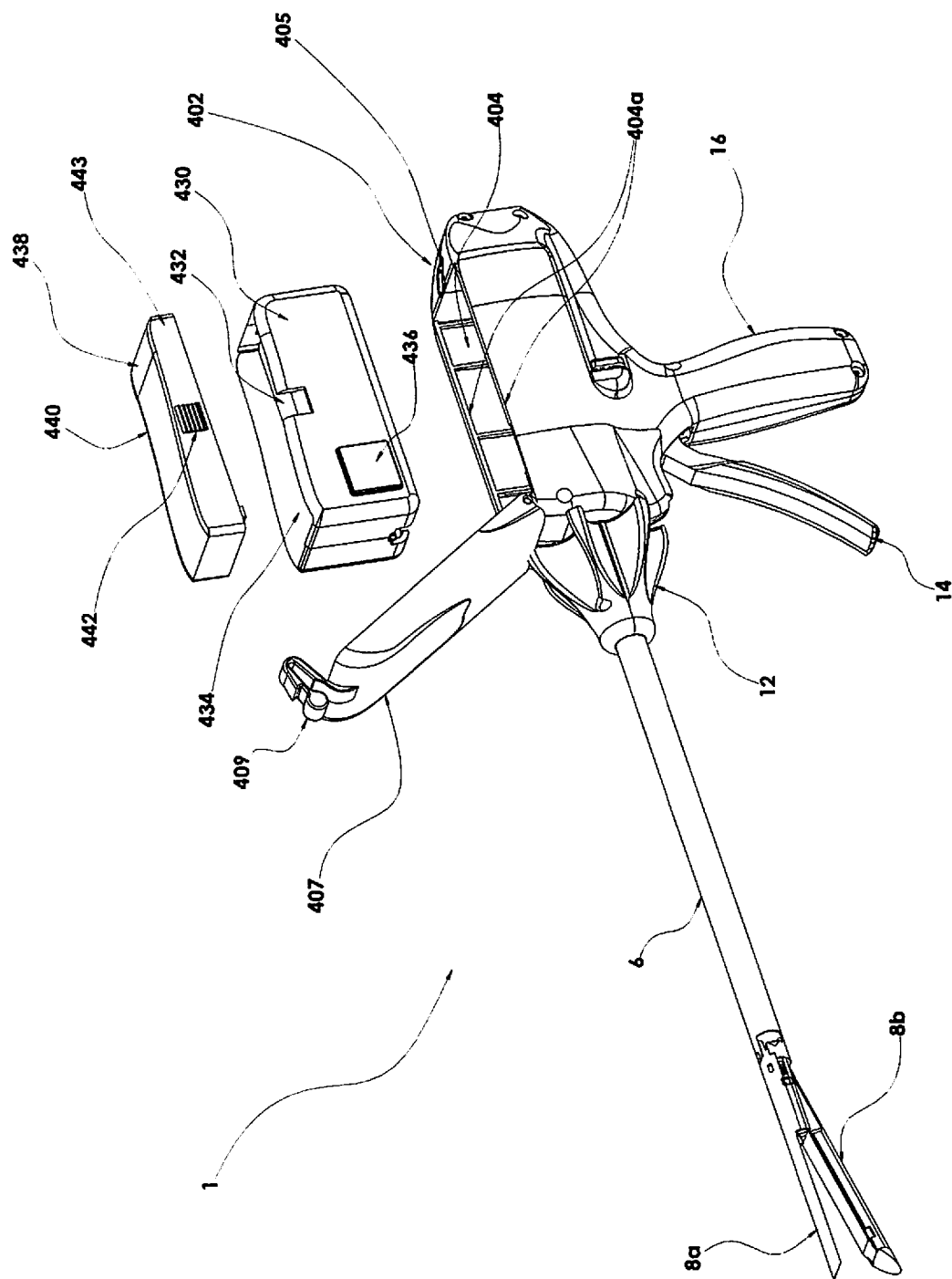
FIG. 37A is a perspective view similar to FIG. 35 illustrating an alternate embodiment of the replaceable battery pack of the present invention.
Figure 37B:
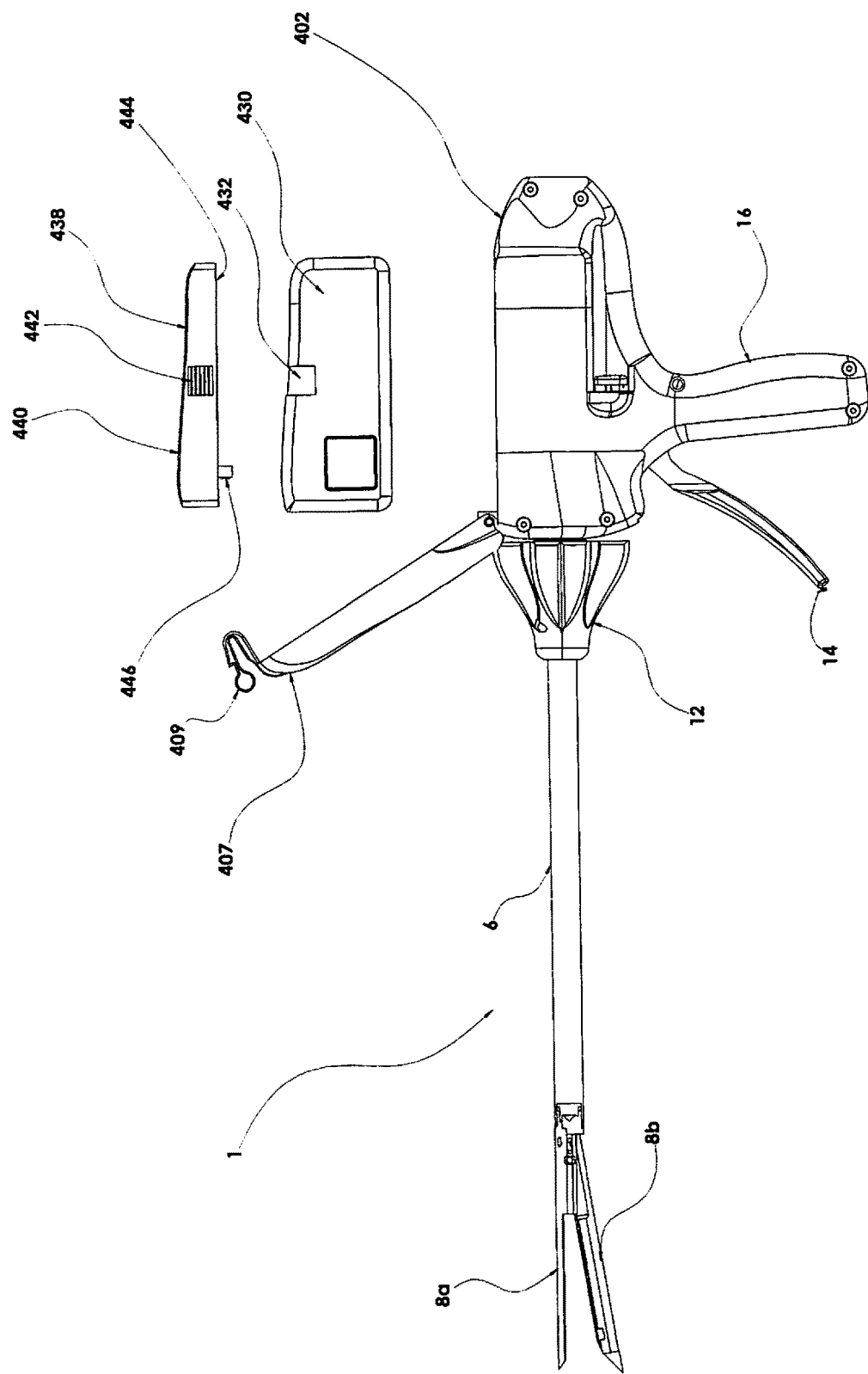
Figure 37C:
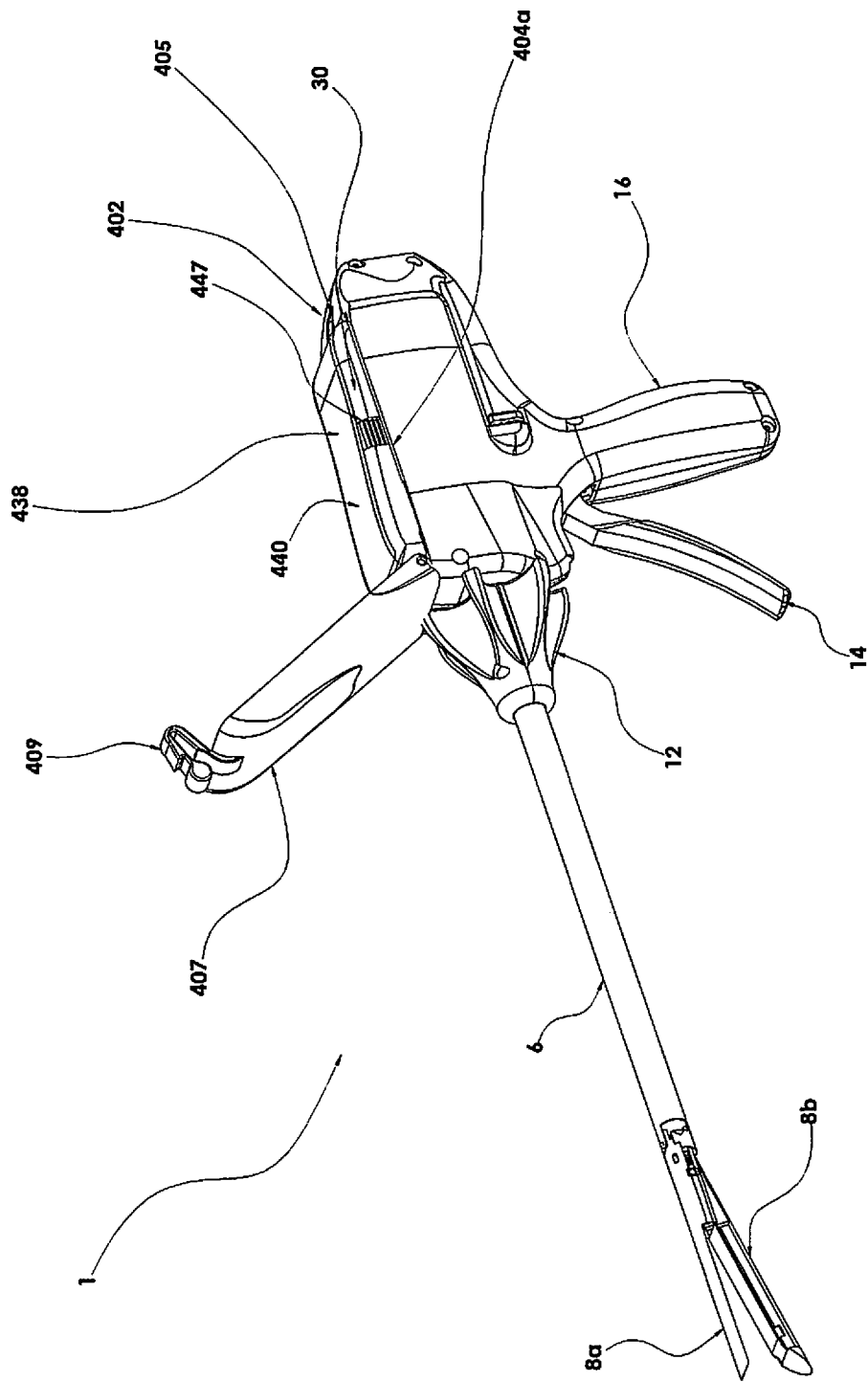

In the alternate embodiment of FIGS. 37A-37C, the battery pack 440 is mounted into a cavity (receptacle) in the power pack 430. Note the stapler 1 of FIGS. 37A-37C is the same as in FIG. 35, the difference being the power pack and battery pack. Power pack 430 has a cavity 432 extending along its length dimensioned to receive battery pack 440. The power pack 430 and battery pack 440 can be dimensioned so that the battery pack 440 becomes part of the outer contour of the power pack 430. Irregular gripping surface or tab 442 on side wall 443 of battery pack 440 is received in cutout 432 in the side wall of power pack 430. The gripping surface can be grasped by the user to facilitate removal as the battery pack 440 is removed from the power pack 430. In some embodiments, a gripping surface or tab like surface 442 can also be provided on the opposing side wall (received in another cavity like cavity 432 positioned on the opposing side) for facilitating grasping both sides of the battery pack 440 for removal from the power pack.

In the loaded position, the battery pack 440 can protrude slightly above the plane of the top edges 404a of the compartment 402 as shown in FIG. 37C or alternatively can be flush or below the plane of the compartment edges 404a. In any case, the power pack 430 and mounted battery pack 440 are placed sufficiently within the compartment 404 so that the cover 407 can be completely closed to seal the power pack 430 and battery pack 440 from the external environment.

In use, the battery pack 440 can be preloaded in the power pack 430, either by a user or packaged with the battery pack 440 preloaded. During a surgical procedure, in the event of a battery failure, the cover 407 can be opened, power pack 430 removed from compartment 404, the battery pack 440 removed from cavity 434, a new (second) charged battery (battery pack) aseptically placed in cavity 434 and the power pack 440 with a replacement battery pack reloaded into compartment 404. In an alternative use, during a surgical procedure, in the event of a battery failure, the cover 407 can be opened and with the power pack 430 remaining in compartment 404, the battery pack 440 is removed from cavity 434 of the power pack 440 and a new (second) charged battery (battery pack) aseptically placed in cavity 434 while the power pack 430 remains loaded (positioned) within the compartment 404.

Note the battery packs disclosed herein can include custom cells or alternatively off the shelf batteries. The use of the term battery pack as used herein encompasses different types of batteries and different housings for the batteries which are mounted on or inserted either fully or partially into the power pack housing (which contains the powertrain therein) to operatively connect with the motor in the power pack.

The battery packs can be retained in or on the power pack housing in various ways such as a latch, spring loaded engagement, frictional engagement, interlocking tabs, etc., and such mountings can also include a release button for disengaging/removing the battery pack from the power pack.

As noted above, the power packs disclosed herein (e.g., power packs 90, 406, 420, 430, 700) can be used with the other staplers disclosed herein, e.g. circular staplers, linear staplers, as well as other instruments wherein two powered functions are desired. The first motor assembly can effect linear motion of a first elongated member to effect a first function of the stapler, e.g., clamping, articulation, firing, and the second motor assembly can effect linear motion of a second elongated member to effect a second different function of the stapler, e.g., clamping, articulation, firing. In the embodiment of FIG. 14A, one function is articulation and another function is staple firing. Note the power packs disclosed herein can also be used with surgical instruments other than surgical staplers such as those illustrated in FIGS. 33A and 34A.

In the foregoing embodiments, use of the power pack of the present disclosure to fire staples such as in endoscopic linear staplers, open surgery linear staplers, circular staplers, as well as firing single clips or tacks were disclosed as examples. It should be appreciated that the power packs of the present disclosure can also be used to power functions of other surgical instruments. FIGS. 33A-34D illustrate two examples of such instruments.

In FIGS. 32A-32D an endoscopic scissors, designated generally by reference numeral 300, can receive and be powered by the power pack 18 (or power pack 90) of the present disclosure. Scissors 300 has a handle 306 manually pivotable towards stationary handle 304 to effect closing of the jaws, an elongated tubular portion 308 extending from the handle housing 302, and a pair of pivotable jaws 312 with cutting edges. Closing of the jaws 312 severs tissue between the jaws. The scissors 300 include a rotation knob 310 for rotation of the elongated portion (shaft) 308 to rotate the jaws 312. Power pack 18 is shown fully loaded (inserted)

within the handle housing 302 and cover 303 is shown closed to seal the power pack 18 from the external environment. As in the embodiment of FIGS. 1-12, the flag 42 extending from lead screw 36 engages a rod within the handle housing 302 operably connected to a jaw closing mechanism to effect movement of jaws 312 toward each other to sever tissue between the jaws 312. Either one or both jaws 312 can be movable.

In FIGS. 33A-33D an endoscopic grasper, designated generally by reference numeral 320, can receive and be powered by the power pack 18 (or power pack 90, 700, etc.) of the present disclosure. Grasper 320 has a handle 326 manually pivotable towards stationary handle 324 to effect closing of the jaws 332, an elongated tubular portion 328 extending from the handle housing 322, and a pair of pivotable jaws 332 with grasping surfaces that can include teeth, roughened surfaces, ribs, etc. Closing of the jaws 332 grasps tissue between the grasping surfaces of jaws 332. Either one of the jaws can be movable, i.e., pivotable, or both jaws can be movable (pivotable) toward and away from each other, for movement between closed and open positions. The graspers 320 includes a rotation knob 330 for rotation of the elongated portion (shaft) 328 to rotate the jaws 332. Power pack 18 is shown fully loaded (inserted) within the handle housing 322 and cover 323 is shown closed to seal the power pack 18 from the external environment. As in the embodiment of FIGS. 1-12, the flag 42 extending from lead screw 36 engages a rod within the handle housing 322 operably connected to a jaw closing mechanism to effect movement of jaws 332 to close the jaws to grasp tissue between the jaws 332. It should be appreciated that the aforedescribed variations of the power packs can also be used with the surgical instruments of FIGS. 32A and 33A.

The power packs disclosed herein (e.g., power packs 18, 90, 404, 420, 430, 700) can be used in surgery where the clinician manually clamps the jaws and actuates the motor or motors to provide powered staple firing and/or powered jaw articulation. It is also contemplated that the power packs disclosed herein can be used with robotic driven surgical staplers wherein clamping, motor actuation and any other functions of the instrument are performed robotically, including remote robotic control.

The staplers disclosed herein, or certain components thereof, can be made of environmental friendly biodegradable materials. For example, the handle can be made of biodegradable material. Such material can include for example corn based lactic acid. The packaging for the surgical staplers and/or the packaging for the power packs and/or the battery packs can also be composed of biodegradable materials to minimize the carbon footprint.

In alternate embodiments, the drive feature for the stapler (in the stapler or power pack/power train) is selectively couplable to various power sources. For example, it could receive electrical power from a corded power source either instead of or in addition to receiving power from a battery. For example, the body (housing) could include a handpiece that has a socket configured to receive a battery or cable adapter. The body in some embodiments could removably receive various shaft assemblies to perform a variety of functions, and the shaft assemblies could include user interface features.

Although the apparatus and methods of the subject disclosure have been described with respect to preferred embodiments, those skilled in the art will readily appreciate that changes and modifications may be made thereto without departing from the spirit and scope of the present disclosure as defined by the appended claims.

What is claimed is:

1. A power pack removably loadable into a compartment of a surgical fastener applier having first and second jaws and a firing mechanism, the power pack comprising a housing having a first motor and a first engagement member removably engageable with the firing mechanism of the applier when the power pack is loaded into the compartment, the first engagement member movable axially within the power pack in response to rotation of a first screw operatively connected to the first motor, and at least one bearing within the removable power pack to limit one or both of radial movement and axial movement of the first screw, wherein linear movement of the first engagement member effects movement of the firing mechanism from a first position to the second position to fire fasteners clamped between the first and second jaws.

2. The power pack of claim 1, wherein the power pack includes a second motor and a second engagement member removably engageable with a second mechanism within the applier when the power pack is loaded into the compartment, the second engagement member movable axially in response to rotation of a second screw operatively connected to the second motor, and at least one bearing within the removable power pack to limit one or both of radial movement and axial movement of the second screw.

3. The power pack of claim 2, wherein linear movement of the second engagement member effects movement of the second mechanism to effect articulation of the first and second jaws.

4. The power pack of claim 1, wherein the first engagement member has a pair of bearings movable within a track as the first engagement member moves axially.

5. The power pack of claim 2, wherein the first and second engagement members are longitudinally spaced and axially aligned along a longitudinal axis.

6. The power pack of claim 1, wherein the first engagement member has a tab engageable with a recess in a disk of the firing mechanism.

7. The power pack of claim 1, wherein the first engagement member is radially offset from a longitudinal axis of the motor.

8. The power pack of claim 1, wherein the at least one bearing comprises a first thrust bearing and a second thrust bearing.

9. The power pack of claim 1, wherein the at least one bearing comprises a first radial bearing and a second radial bearing, wherein the first and second radial bearings engage opposite ends of the first screw.

10. The power pack of claim 1, wherein the at least one bearing comprises a first thrust bearing and a second thrust bearing, wherein the first and second thrust bearings engage opposite ends of the first screw.

11. The power pack of claim 8, wherein the first thrust bearing is slip fit over an outer diameter of the first screw and floats relative to the first screw.

12. The power pack of claim 1, wherein the first screw has a reduced diameter portion to form a shoulder at a larger diameter portion to contact the at least one bearing and the at least one bearing can rotate freely but is axially constrained by the shoulder.

13. The power pack of claim 1, wherein the first engagement member radially engages the firing mechanism when the power pack is loaded into the compartment.

14. A power pack removably loadable into a compartment of a surgical fastener applier having first and second jaws and a firing mechanism, the power pack comprising a housing having a first motor and a first engagement member removably engageable with the firing mechanism of the applier when the power pack is loaded into the compartment, the first engagement member movable axially within the power pack in response to rotation of a first screw operatively connected to the first motor, wherein linear movement of the first engagement member effects movement of the firing mechanism from a first position to the second position to fire fasteners clamped between the first and second jaws, and a second engagement member movable axially in response to rotation of a second screw operatively connected to a second motor, the second engagement member removably engageable with a second mechanism in the applier, the first engagement member radially engaging the firing mechanism and the second engagement member radially engaging the second mechanism when the power pack is loaded into the compartment.

15. The power pack of claim 14, wherein the first engagement member comprises a collar having a yoke to engage the first engagement member.

16. The power pack of claim 14, wherein the first motor is positioned parallel to the first screw and the second motor is axially aligned with the second screw.

17. The power pack of claim 14, wherein the first and second engagement members are axially spaced such that the first engagement member is at a first region of the housing and the second engagement member is at a second opposite region of the housing.

18. The power pack of claim 14, wherein the first and second engagement members are axially aligned along a longitudinal axis.

\* \* \* \* \*